(12) United States Patent
Lewis et al.

(10) Patent No.: US 8,646,446 B2
(45) Date of Patent: Feb. 11, 2014

(54) DRY POWDER INHALERS WITH ROTATING PIERCING MECHANISMS AND RELATED DEVICES AND METHODS

(75) Inventors: Scott Alexander Lewis, Cambbridge (GB); Andrew Murray Gow, Porirua (NZ); Jonathan David Tuckwell, Cambridge (GB); Greg Beard, Raleigh, NC (US); David Harris, Cambridge (GB)

(73) Assignee: Oriel Therapeutics, Inc., Durham, NC (US)

( * ) Notice: Subject to any disclaimer, the term of this patent is extended or adjusted under 35 U.S.C. 154(b) by 288 days.

(21) Appl. No.: 13/054,809

(22) PCT Filed: Sep. 25, 2009

(86) PCT No.: PCT/US2009/005338
§ 371 (c)(1),
(2), (4) Date: Apr. 15, 2011

(87) PCT Pub. No.: WO2010/039202
PCT Pub. Date: Apr. 8, 2010

(65) Prior Publication Data
US 2011/0186047 A1 Aug. 4, 2011

Related U.S. Application Data

(60) Provisional application No. 61/101,832, filed on Oct. 1, 2008.

(51) Int. Cl.
*A61M 16/00* (2006.01)
*A61M 15/00* (2006.01)

(52) U.S. Cl.
USPC .................. 128/203.21; 128/203.12; 222/144

(58) Field of Classification Search
USPC .......................... 128/200.14, 203.21, 203.22, 128/203.12–203.15; 222/3–6, 80, 81, 83, 222/144, 541.2
See application file for complete search history.

(56) References Cited

U.S. PATENT DOCUMENTS 2,828,005 A * 3/1958 Ricke ............................ 206/533
4,307,734 A 12/1981 Blankenship
(Continued)

FOREIGN PATENT DOCUMENTS

DE 195 00 764 A1 7/1996
DE 19500764 7/1996
(Continued)

OTHER PUBLICATIONS

Notification of Transmittal of the International Search Report and the Written Opinion of the International Searching Authority issued May 14, 2010 by the Korean Intellectual Property Office for PCT Application No. PCT/US2009/005338.

(Continued)

*Primary Examiner* — Justine Yu
*Assistant Examiner* — Michael Tsai
(74) *Attorney, Agent, or Firm* — Myers Bigel Sibley & Sajovec, P.A.

(57) ABSTRACT

Dry powder inhalers with rotatable piercing mechanisms facilitate the use of dose container assemblies having dose containers arranged in concentric rows. A piercing mechanism is operably associated with the dose container assembly and is configured to pierce sealants that seal a dose container. The piercing mechanism is rotatable such that it can serially alternate between the two rows of dose containers. The piercing mechanism includes a rotatable drum, an elongate piercing member, and a biasing member operably associated with the piercing member. The rotatable drum has an open end, an opposite closed end, and a cylindrical wall that extends from the closed end and terminates at the open end. The closed end includes an aperture formed therein in a location adjacent to the wall. The elongate piercing member is extended and retracted through the aperture to pierce the sealants of a dose container.

31 Claims, 48 Drawing Sheets

(56) References Cited

U.S. PATENT DOCUMENTS

| | | | |
|---|---|---|---|
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,138,138 A | 8/1992 | Theilacker et al. | |
| 5,327,883 A | 7/1994 | Williams et al. | |
| 5,337,740 A | 8/1994 | Armstrong et al. | |
| 5,388,572 A * | 2/1995 | Mulhauser et al. | 128/203.15 |
| 5,394,868 A | 3/1995 | Ambrosio et al. | |
| 5,529,059 A | 6/1996 | Armstrong et al. | |
| 5,533,502 A | 7/1996 | Piper | |
| 5,590,645 A | 1/1997 | Davies et al. | |
| 5,622,166 A | 4/1997 | Eisele et al. | |
| 5,634,900 A | 6/1997 | Makino et al. | |
| 5,715,810 A | 2/1998 | Armstrong et al. | |
| 5,727,607 A | 3/1998 | Ichikawa et al. | |
| 5,769,073 A | 6/1998 | Eason et al. | |
| 5,860,419 A | 1/1999 | Davies et al. | |
| 5,873,360 A | 2/1999 | Davies et al. | |
| 5,909,829 A | 6/1999 | Wegman et al. | |
| 5,921,237 A | 7/1999 | Eisele et al. | |
| 5,947,169 A | 9/1999 | Wegman et al. | |
| 6,029,663 A | 2/2000 | Eisele et al. | |
| 6,032,666 A | 3/2000 | Davies et al. | |
| 6,082,356 A | 7/2000 | Stradella | |
| 6,116,237 A | 9/2000 | Schultz et al. | |
| 6,116,238 A | 9/2000 | Jackson et al. | |
| 6,245,339 B1 | 6/2001 | Van Oort et al. | |
| 6,328,033 B1 | 12/2001 | Avrahami | |
| 6,367,473 B1 | 4/2002 | Käfer | |
| 6,378,519 B1 | 4/2002 | Davies et al. | |
| 6,445,941 B1 | 9/2002 | Hampton et al. | |
| 6,536,427 B2 | 3/2003 | Davies et al. | |
| 6,543,448 B1 | 4/2003 | Smith et al. | |
| 6,550,477 B1 * | 4/2003 | Casper et al. | 128/203.21 |
| 6,591,832 B1 | 7/2003 | DeJonge | |
| 6,655,381 B2 | 12/2003 | Keane et al. | |
| 6,668,827 B2 | 12/2003 | Schuler et al. | |
| 6,679,254 B1 * | 1/2004 | Rand et al. | 128/203.15 |
| 6,792,945 B2 | 9/2004 | Davies et al. | |
| 6,810,872 B1 | 11/2004 | Ohki et al. | |
| 6,871,647 B2 | 3/2005 | Allan et al. | |
| 6,880,555 B1 | 4/2005 | Brunnberg et al. | |
| 6,915,802 B1 | 7/2005 | Anderson et al. | |
| 6,923,178 B2 | 8/2005 | Snow | |
| 6,948,494 B1 | 9/2005 | Snow | |
| 7,089,935 B1 * | 8/2006 | Rand | 128/203.15 |
| 7,219,665 B1 * | 5/2007 | Braithwaite | 128/203.21 |
| 7,225,808 B2 | 6/2007 | Davies et al. | |
| 7,275,538 B2 | 10/2007 | Nakamura | |
| 7,318,436 B2 | 1/2008 | Snow | |
| 7,389,775 B2 | 6/2008 | Davies et al. | |
| 7,503,324 B2 | 3/2009 | Barney et al. | |
| 7,571,723 B2 | 8/2009 | Braithwaite | |
| 7,571,724 B2 | 8/2009 | Braithwaite | |
| 7,669,597 B2 | 3/2010 | Sullivan et al. | |
| 8,037,880 B2 * | 10/2011 | Zhu et al. | 128/203.12 |
| 2001/0007853 A1 | 7/2001 | Dimarchi et al. | |
| 2001/0053761 A1 | 12/2001 | Dimarchi et al. | |
| 2002/0040713 A1 | 4/2002 | Eisele et al. | |
| 2002/0170560 A1 | 11/2002 | Young et al. | |
| 2003/0178024 A1 | 9/2003 | Allan et al. | |
| 2004/0025877 A1 | 2/2004 | Crowder et al. | |
| 2005/0056281 A1 | 3/2005 | Snow | |
| 2005/0126568 A1 | 6/2005 | Davies et al. | |
| 2005/0154491 A1 | 7/2005 | Anderson et al. | |
| 2005/0161041 A1 | 7/2005 | Schuler et al. | |
| 2005/0172963 A1 | 8/2005 | Allan et al. | |
| 2006/0102511 A1 | 5/2006 | Pasbrig et al. | |
| 2006/0157053 A1 | 7/2006 | Barney et al. | |
| 2007/0062525 A1 | 3/2007 | Bonney et al. | |
| 2007/0137643 A1 | 6/2007 | Bonney et al. | |
| 2007/0137645 A1 | 6/2007 | Eason et al. | |
| 2007/0181123 A1 | 8/2007 | Houzego | |
| 2007/0181124 A1 | 8/2007 | Casper et al. | |
| 2007/0215149 A1 | 9/2007 | King et al. | |
| 2007/0221218 A1 * | 9/2007 | Warden et al. | 128/203.15 |
| 2007/0235029 A1 | 10/2007 | Zhu et al. | |
| 2008/0127971 A1 | 6/2008 | King et al. | |
| 2008/0223366 A1 | 9/2008 | Davies et al. | |
| 2009/0114220 A1 | 5/2009 | Wachtel et al. | |
| 2009/0139516 A1 | 6/2009 | Augustyn et al. | |
| 2010/0078022 A1 | 4/2010 | Striebig et al. | |
| 2011/0162648 A1 | 7/2011 | Ruckdeschel | |

FOREIGN PATENT DOCUMENTS

| | | |
|---|---|---|
| EP | 1106196 | 3/2001 |
| EP | 1 779 884 A1 | 5/2007 |
| EP | 1844805 | 10/2007 |
| GB | 873410 | 7/1961 |
| GB | 2 246 299 A | 1/1992 |
| GB | 2340758 | 3/2000 |
| JP | 2002-536080 | 10/2002 |
| JP | 2004-527271 A | 9/2004 |
| WO | WO 94/14490 | 7/1994 |
| WO | WO 94/20164 | 9/1994 |
| WO | WO 98/41265 | 9/1998 |
| WO | WO 99/36116 | 7/1999 |
| WO | WO 00/45879 | 8/2000 |
| WO | WO 01/17595 A1 | 3/2001 |
| WO | WO 01/28616 | 4/2001 |
| WO | WO 01/34234 | 5/2001 |
| WO | WO 02/053215 | 7/2002 |
| WO | WO 02/053215 A2 | 7/2002 |
| WO | WO 02/053216 | 7/2002 |
| WO | WO 03/011708 | 2/2003 |
| WO | WO 2004/045487 | 6/2004 |
| WO | WO 2004/045487 A2 | 6/2004 |
| WO | WO 2005/002654 | 1/2005 |
| WO | WO 2005/037353 | 4/2005 |
| WO | WO 2005/044173 | 5/2005 |
| WO | WO 2005/110519 | 11/2005 |
| WO | WO 2006/031775 | 3/2006 |
| WO | WO 2006/108877 | 10/2006 |
| WO | WO 2007/007110 | 1/2007 |
| WO | WO 2007/012871 | 2/2007 |
| WO | WO 2007/118648 A1 | 10/2007 |
| WO | WO 2008/039182 A1 | 4/2008 |
| WO | WO 2010/036355 A2 | 4/2010 |
| WO | WO 2010/036839 A2 | 4/2010 |

OTHER PUBLICATIONS

Australian Office Action Corresponding to Australian Application No. 2009296535; Date of Issue: Mar. 1, 2013; 3 Pages.

Japanese Office Action Corresponding to Japanese Patent Application No. 2011-529238; Dispatch Date: Mar. 1, 2013; 3 Pages (Foreign Text Only).

European Search Report Corresponding to European Application No. 09816585.5; Dated: Feb. 1, 2012; 8 pages.

European Search Report Corresponding to European Application No. 09818090.4; Dated: Mar. 21, 2012; 5 pages.

Australian Examination Report Corresponding to Australian Patent Application No. 2009296538; Date of Issue: Oct. 19, 2012; 4 Pages.

Hickey et al., A new millennium for inhaler technology, 21 Pharm. Tech., n. 6, pp. 116-125 (1997).

International Search Report and Written Opinion for corresponding PCT application No. PCT/US2009/058285, date of mailing Apr. 14, 2010.

Notification of Transmittal of the International Search Report and the Written Opinion of the International Searching Authority, or the Declaration issued by the European Patent Office on Jan. 7, 2010 for the corresponding International Application No. PCT/US2009/058281.

Notification of Transmittal of the International Search Report and the Written Opinion of the International Searching Authority issued May 4, 2010 by the Korean Intellectual Property Office for corresponding PCT Application No. PCT/US20098/005336.

PCT Invitation to Pay Additional Fees and Partial Search for corresponding PCT Application No. PCT/US2009/058285, Date of Mailing Dec. 30, 2009.

(56) References Cited

OTHER PUBLICATIONS

Prime et al., Review of Dry Powder Inhalers, 26 Adv. Drug Delivery Rev., pp. 51-58 (1997).
Wolff et al., Generation of Aerosolized Drugs, J. Aerosol. Med., pp. 88-106 (1994).

Chinese Office Action Corresponding to Chinese Patent Application No. 200980136939.8; Date of Notification: Nov. 20, 2012; 8 Pages.
Office Action, Mexican Patent Application No. MX/A/2011/003232, Aug. 27, 2013.

* cited by examiner

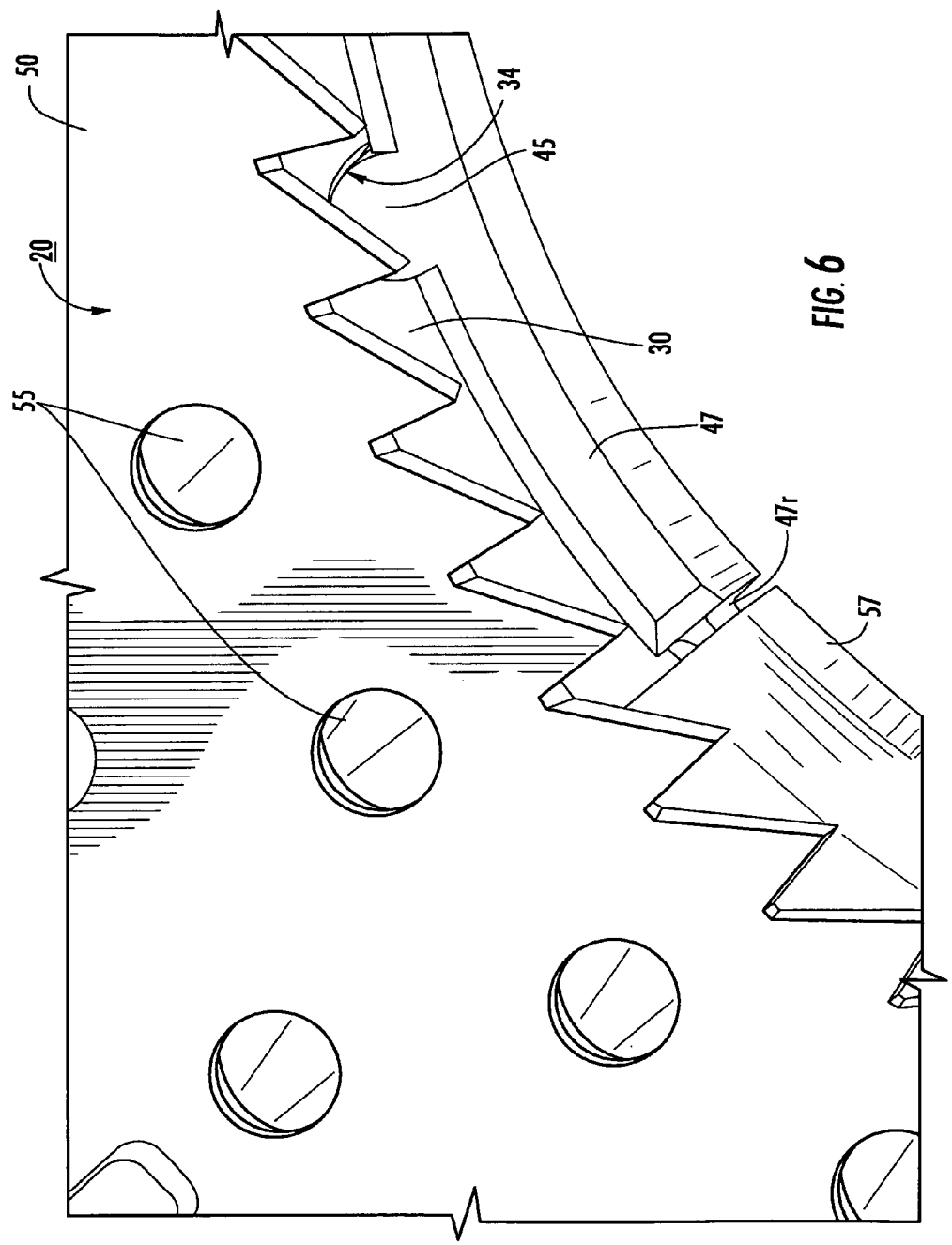

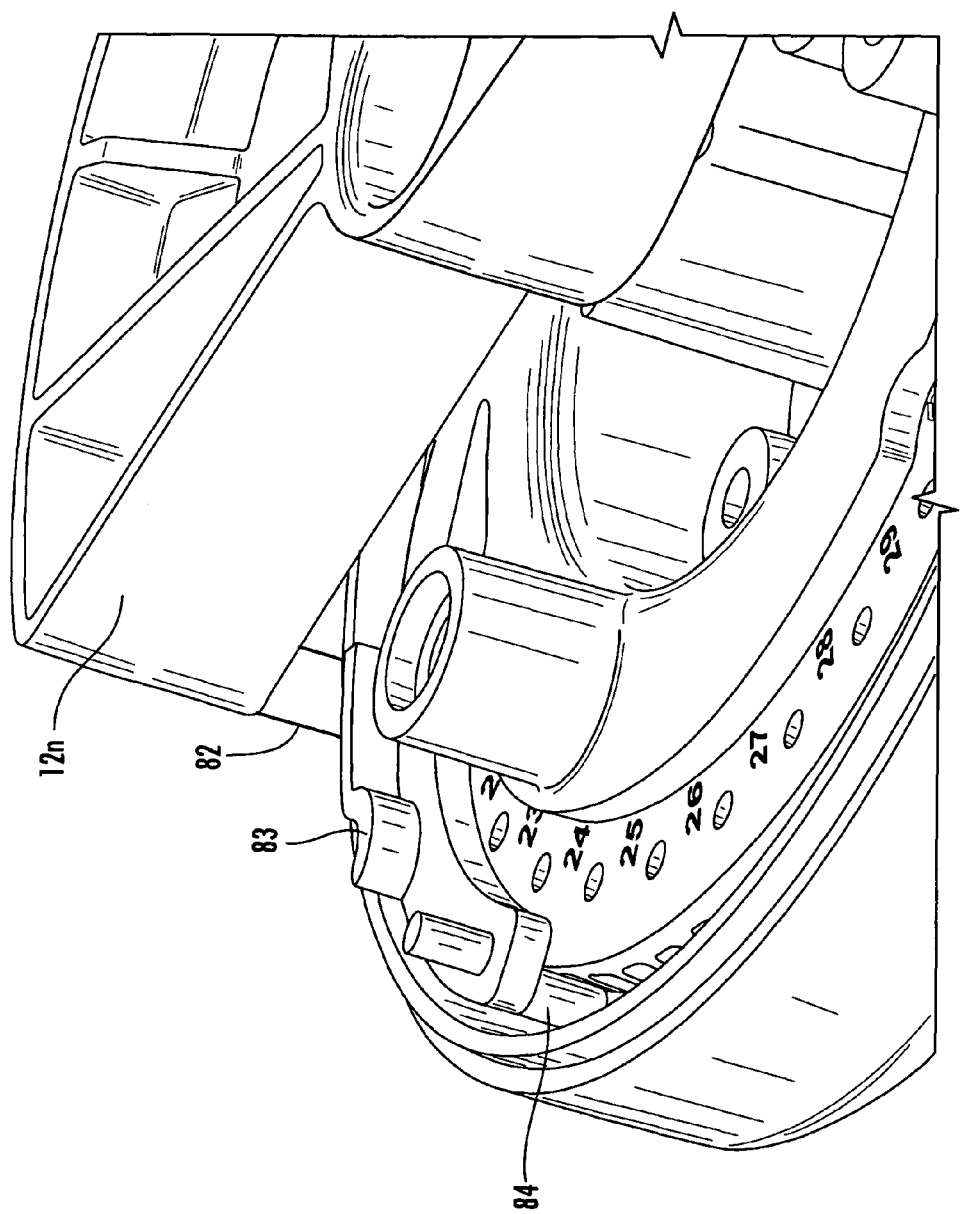

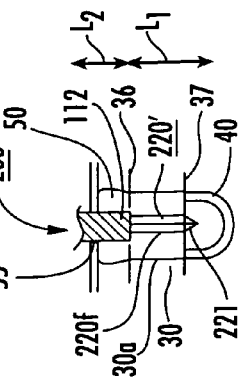
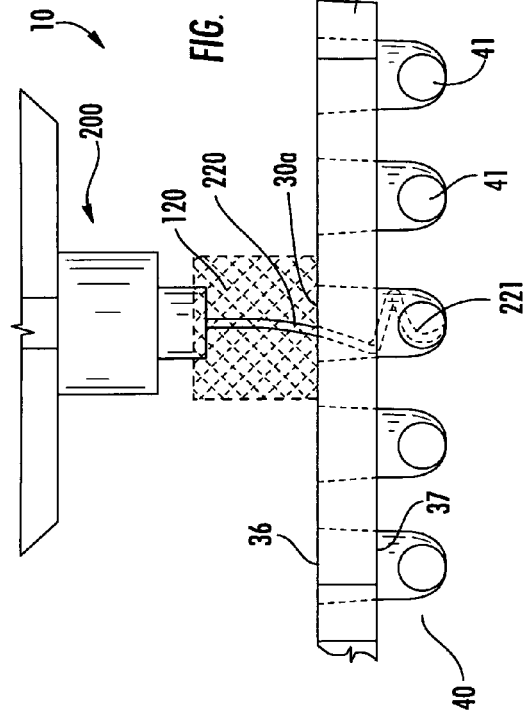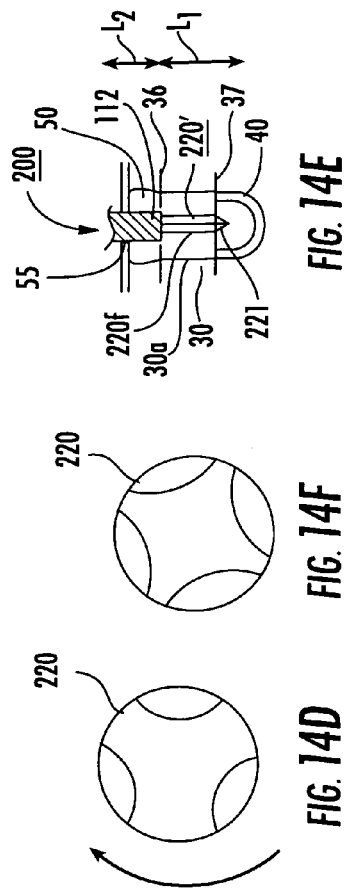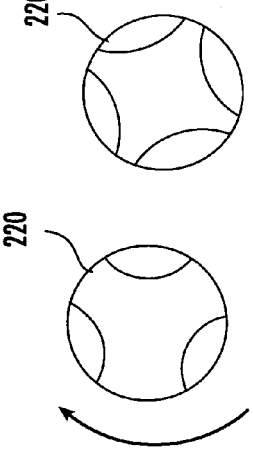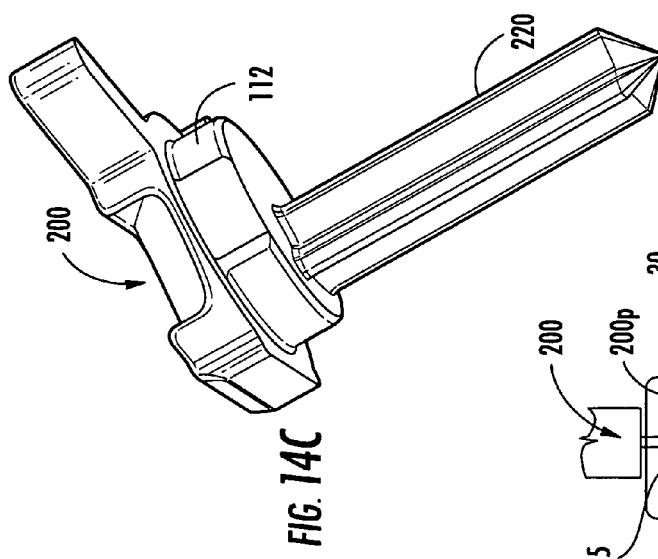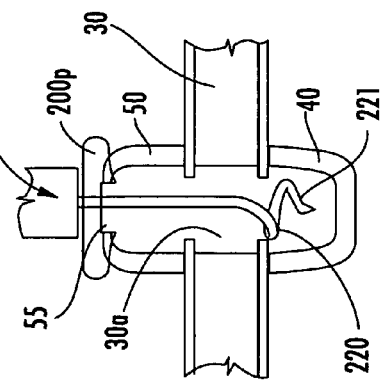

DRY POWDER INHALERS WITH ROTATING PIERCING MECHANISMS AND RELATED DEVICES AND METHODS

RELATED APPLICATIONS

This application is a 35 USC 371 national phase application of PCT/US2009/005338, filed Sep. 25, 2009, which claims the benefit of priority to U.S. Provisional Application Ser. No. 61/101,832, filed Oct. 1, 2008, the contents of which are hereby incorporated by reference as if recited in full herein.

FIELD OF THE INVENTION

The present invention relates to inhalers, and may be particularly suitable for dry powder inhalers.

BACKGROUND

Dry powder inhalers (DPIs) are an alternative to pMDI (pressurized metered dose inhaler) devices for delivering drug aerosols without using propellants. Typically, DPIs are configured to deliver a powdered drug or drug mixture that includes an excipient and/or other ingredients. Generally described, known single and multiple dose dry powder DPI devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose.

In operation, DPI devices strive to administer a uniform aerosol dispersion amount in a desired physical form of the dry powder (such as a particulate size or sizes) into a patient's airway and direct it to a desired internal deposit site(s).

There remains a need for alternative inhalers and/or dose containment devices that can be used to deliver medicaments.

SUMMARY

Embodiments of the present invention provide dry powder inhalers with rotatable piercing mechanisms that facilitate the use of dose rings or disks having dose containers arranged in concentric rows. According to some embodiments, a dose container assembly includes a dose container disk having opposing upper and lower primary surfaces, a first row of circumferentially spaced apart dose containers at a first radius and a second row of circumferentially spaced apart dose containers at a second radius so that the first and second rows are concentric with respect to a center of the disk. The dose containers have dry powder therein. A first flexible sealant resides over apertures in the upper surface, and a second flexible sealant resides over apertures in the lower surface to contain the powder within the dose containers.

A piercing mechanism is operably associated with the dose container assembly and is configured to pierce the first and second sealants that seal a dose container. The piercing mechanism is rotatable such that it can serially alternate between the two rows of dose containers in the dose container disk. The piercing mechanism includes a rotatable drum, an elongate piercing member, and a biasing member operably associated with the piercing member. The rotatable drum has an open end, an opposite closed end, and a cylindrical wall that extends from the closed end and terminates at the open end. The closed end includes an aperture formed therein in a location adjacent to the wall. The elongate piercing member is extended and retracted through the aperture to pierce the first and second sealants of a dose container. In some embodiments, gear teeth extend circumferentially around the wall adjacent the open end. However, the gear teeth may be positioned at other locations and may have other configurations. A support member extends outwardly from the closed end, and is configured to support the piercing member for reciprocal movement The elongate piercing member includes a distal piercing portion and a proximal head portion. In some embodiments, the distal piercing portion can be a solid piercer configured to pierce the sealants. In some embodiments, the distal piercing portion can be a corkscrew piercer configured to pierce the sealants with a straight vertical non-rotational movement. In some embodiments, the distal piercing portion can have a fluted piercer configured to pierce the sealants.

The elongate piercing member is movably associated with the support member in the drum so as to be capable of reciprocal movement between piercing and non-piercing positions. In the piercing position, the piercing member distal piercing portion extends through the drum aperture and through the first and second sealants of a dose container. In a retracted position, the distal piercing portion is retracted above a lower surface of the drum aperture, such that the drum is free to rotate. A biasing member is configured to urge the piercing member toward retracted positions.

A ring gear is rotatably secured within the inhaler housing, and includes multiple sets of teeth that are circumferentially spaced-apart from each other along a perimeter, thereof. The ring gear includes a plurality of spaced-apart steps. Each step is configured to be engaged by a pawl associated with an actuator of the inhaler. The piercing mechanism is positioned relative to the ring gear such that the drum gear teeth cooperate with the sets of teeth on the ring gear outer perimeter. Rotation of the ring gear by a predetermined amount, when a set of teeth are engaged with the drum gear teeth, causes the drum to rotate such that the piercing member moves from a position overlying a dose container in one row to a position overlying a dose container in the other row.

The dose container assembly includes gear teeth on an outer or inner perimeter thereof. Diametrically opposed teeth extend outwardly from the drum wall and are configured to engage the dose container assembly gear teeth. Rotation of the drum via the ring gear, in turn, causes rotation of the dose container assembly to move a fresh dose container into position beneath the piercing mechanism.

In some embodiments, the inhaler includes a user-accessible actuator that is movable between first and second positions. When moved from the first position to the second position, the actuator causes the piercing member to open a dose container in a row by piercing the first and second sealants associated therewith. When moved from the second position back to the first position, a pawl associated with the actuator engages a step on the inner perimeter of the ring gear, and causes rotation of the ring gear which causes rotation of the drum by an amount sufficient to position the piercing mechanism above a dose container in the other row on the disk. In addition, one of the diametrically opposed teeth extending from the drum engages a mating tooth on the dose container assembly and rotates the dose container assembly a predetermined amount such that a fresh dose container is positioned under the piercing member, and the inhaler is ready for another cycle.

In other embodiments, the actuator includes a pair of ramps positioned in adjacent, spaced-apart relationship, and the piercing mechanism includes a pair of arms extending outwardly therefrom in opposing relationship. Each ramp includes a first leg attached to an actuator surface and a second leg having a free end adjacent to the actuator surface. When moved from the first position to the second position, the actuator causes rotation of the ring gear by a predetermined amount. During a first stage of the rotation, a first set of ring gear teeth cooperates with the drum gear teeth and rotates the drum such that the piercing member overlies a dose container. During a second stage of the rotation, each arm is contacted by a respective ramp second leg to urge the piercing member to the piercing position. During the third stage of the rotation, each arm disengages from a respective ramp and the piercing member is urged to a partially retracted position by a biasing member. When the actuator is moved from the second position to the first position, the second leg of each ramp deflects such that a respective arm passes between the free end and the actuator surface.

According to some embodiments of the present invention, operations that can be used to operate an inhaler include providing a dose container disk having opposing upper and lower primary surfaces, a first row of circumferentially spaced apart dose containers at a first radius and a second row of circumferentially spaced apart dose containers at a second radius so that the first and second rows are concentric with respect to a center of the disk. The dose containers have dry powder therein, and each dose container terminates at a respective aperture in the upper surface and at a respective aperture in the lower surface. A first flexible sealant resides over the apertures in the upper surface, and a second flexible sealant resides over the apertures in the lower surface. A rotatable piercing mechanism is advanced to open both sealants and release dry powder from a dose container in one of the rows. The piercing mechanism is then retracted from the dose container and rotated to a position above a dose container in the other row.

In other embodiments, operations can be reversed. In other words, the rotatable piercing mechanism can be rotated into position above a dose container in a row first, followed by advancing the piercing mechanism to open both sealants and release dry powder from the dose container. As such, inhalers, according to some embodiments of the present invention, can have piercing mechanisms configured to "pierce then rotate and index" and, in other embodiments, piercing mechanisms configured to "rotate and index then pierce."

A dry powder inhaler, according to other embodiments of the present invention, includes a housing, a dose container assembly rotatably secured within the housing, and a piercing mechanism. The dose container assembly includes a dose container disk having opposing upper and lower primary surfaces, a first row of circumferentially spaced apart dose containers at a first radius and a second row of circumferentially spaced apart dose containers at a second radius so that the first and second rows are concentric with respect to a center of the disk. Each dose container terminates at a respective aperture in the upper surface and at a respective aperture in the lower surface. A first flexible sealant resides over the apertures in the upper surface, and a second flexible sealant resides over the apertures in the lower surface. The dose containers have dry powder therein.

The piercing mechanism is operably associated with the dose container assembly and is configured to pierce the first and second sealants residing over respective dose container apertures. The piercing mechanism is configured to serially alternate between rows to pierce the sealants over and under a dose container in a first row of dose container apertures, then pierce the sealants over and under a dose container in a second row of dose container apertures. In some embodiments, the piercing mechanism includes a rotatable drum having an open end, an opposite closed end, and a cylindrical wall extending from the closed end and terminating at the open end; an elongate piercing member capable of reciprocal movement between piercing and non-piercing positions; and a biasing member configured to urge the piercing member toward a retracted position. The drum closed end includes an aperture formed therein. Gear teeth extend circumferentially around the wall adjacent the drum open end. The piercing member includes a distal piercing portion and a proximal head portion. The distal piercing portion extends through the drum aperture and through the first and second sealants when the piercing member is in a piercing position. The distal piercing portion is retracted above a lower surface of the drum aperture when in a retracted position.

A ring gear is rotatably secured within the housing and includes a plurality of sets of teeth that are circumferentially spaced-apart from each other. An actuator that is movable by a user of the inhaler between first and second positions is configured to cause rotation of the ring gear by a predetermined amount. During a first stage of the ring gear rotation via the actuator, a first set of ring gear teeth cooperates with the drum gear teeth and rotates the drum such that the piercing member overlies a dose container. During a second stage of the ring gear rotation via the actuator, the piercing member is moved to the piercing position. During a third stage of the ring gear rotation via the actuator, the piercing member is moved to the retracted position. During a fourth stage of the ring gear rotation via the actuator, a second set of ring gear teeth cooperates with the drum gear teeth and rotates the drum such that the piercing member does not overlie a dose container.

In some embodiments, the actuator includes a ramp, and the piercing member includes an arm extending outwardly therefrom. During the second stage of the ring gear rotation, the arm is contacted by the ramp to urge the piercing member to the piercing position. During the third stage of the rotation, the arm disengages from the ramp and the piercing member is urged to the retracted position by the biasing member.

In some embodiments, a pair of arms extend outwardly from the piercing member in opposing relationship. The ramp includes spaced-apart first and second inclined portions. Each arm is configured to engage a respective inclined portion during the second stage of rotation of the ring gear. As such, during the second stage of the ring gear rotation, each arm is contacted by a respective inclined portion to urge the piercing member to the piercing position.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 6 is a greatly enlarged partial view of the dose container assembly shown in FIG. 2A according to embodiments of the present invention.

FIGS. 10B-10D are greatly enlarged partial cutaway side perspective views of an inhaler with a biasing mechanism according to embodiments of the present invention.

FIG. 14A is an enlarged partial section view of a piercing member according to some embodiments of the present invention.

FIG. 14B is an enlarged partial section view of a piercing member similar to that shown in FIG. 14A, according to some embodiments of the present invention.

FIG. 14C is a partial front schematic view of a piercing member with a fluted configuration, according to some embodiments of the present invention.

FIG. 14D is an end view of the device shown in FIG. 14C.

FIG. 14E is a partial front schematic view of another fluted piercer configuration according to some embodiments of the present invention.

FIG. 14F is an end view of an exemplary four lobe fluted piercer configuration, according to some embodiments of the present invention.

DETAILED DESCRIPTION

Figure 1A:
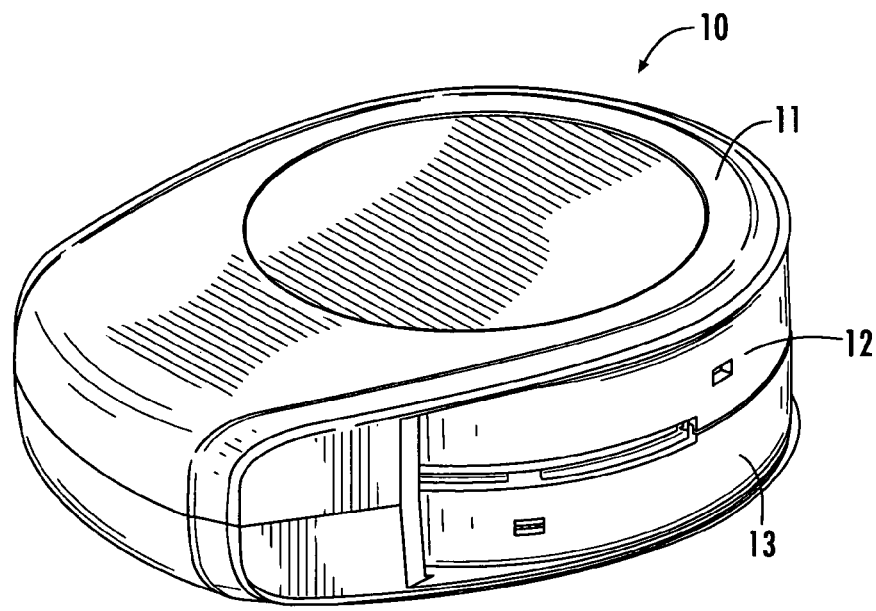
FIG. 1A is a front perspective view of an inhaler with a cover, according to some embodiments of the present invention, and where the cover is in a closed position.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment of figure although not specifically described or shown as such.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various regions, layers and/or sections, these regions, layers and/or sections should not be limited by these terms. These terms are only used to distinguish one region, layer or section from another region, layer or section. Thus, a first region, layer or section discussed below could be termed a second region, layer or section, and similarly, a second region, layer or section discussed below could be termed a first region, layer or section without departing from the teachings of the present invention. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

In the description of the present invention that follows, certain terms are employed to refer to the positional relationship of certain structures relative to other structures. As used herein, the term "front" or "forward" and derivatives thereof refer to the general or primary direction that the dry powder travels to be dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction. The term "deagglomeration" and its derivatives refer to processing dry powder in the inhaler airflow path to inhibit the dry powder from remaining or becoming agglomerated or cohesive during inspiration.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery, but are typically oral inhalers.

The terms "sealant", "sealant layer" and/or "sealant material" includes configurations that have at least one layer of at least one material and can be provided as a continuous layer that covers the entire upper surface and/or lower surface or may be provided as strips or pieces to cover portions of the device, e.g., to reside over at least a target one or more of the dose container apertures. Thus, terms "sealant" and "sealant layer" includes single and multiple layer materials, typically comprising at least one foil layer. The sealant or sealant layer can be a thin multi-layer laminated sealant material with elastomeric and foil materials. The sealant layer can be selected to provide drug stability as they may contact the dry powder in the respective dose containers.

The sealed dose containers can be configured to inhibit oxygen and moisture penetration to provide a sufficient shelf life.

The term "primary surface" refers to a surface that has a greater area than another surface and the primary surface can be substantially planar or may be otherwise configured. For example, a primary surface can include protrusions or recessions, such as where some blister configurations are used. Thus, a disk can have upper and lower primary surfaces and a minor surface (e.g., a wall with a thickness) that extends between and connects the two.

The dry powder substance may include one or more active pharmaceutical constituents as well as biocompatible additives that form the desired formulation or blend. As used herein, the term "dry powder" is used interchangeably with "dry powder formulation" and means that the dry powder can comprise one or a plurality of constituents or ingredients with one or a plurality of (average) particulate size ranges. The term "low-density" dry powder means dry powders having a density of about 0.8 g/cm$^3$ or less. In particular embodiments, the low-density powder may have a density of about 0.5 g/cm$^3$ or less. The dry powder may be a dry powder with cohesive or agglomeration tendencies.

The term "filling" means providing a bolus or sub-bolus metered amount of dry powder. Thus, the respective dose container is not required to be volumetrically full.

In any event, individual dispensable quantities of dry powder formulations can comprise a single ingredient or a plurality of ingredients, whether active or inactive. The inactive ingredients can include additives added to enhance flowability or to facilitate aerosolization delivery to the desired target. The dry powder drug formulations can include active particulate sizes that vary. The device may be particularly suitable for dry powder formulations having particulates which are in the range of between about 0.5-50 µm, typically in the range of between about 0.5 µm-20.0 µm, and more typically in the range of between about 0.5 µm-8.0 µm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 µm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, or composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroids, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally-acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhalers may vary depending on the patient size, the systemic target, and the particular drug(s). The dose amounts and type of drug held by a dose container system may vary per dose container or may be the same. In some embodiments, the dry powder dose amounts can be about 100 mg or less, typically less than 50 mg, and more typically between about 0.1 mg to about 30 mg.

In some embodiments, such as for pulmonary conditions (i.e., asthma or COPD), the dry powder can be provided as about 5 mg total weight (the dose amount may be blended to provide this weight). A conventional exemplary dry powder dose amount for an average adult is less than about 50 mg, typically between about 10-30 mg and for an average adolescent pediatric subject is typically from about 5-10 mg. A typical dose concentration may be between about 1-5%. Exemplary dry powder drugs include, but are not limited to, albuterol, fluticasone, beclamethasone, cromolyn, terbutaline, fenoterol, β-agonists (including long-acting β-agonists), salmeterol, formoterol, corticosteroids and glucocorticoids.

In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during inhalation, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In some embodiments, the unit dose amount of dry powder held in a respective drug compartment or dose container is less than about 10 mg, typically about 5 mg of blended drug and lactose or other additive (e.g., 5 mg LAC), for treating pulmonary conditions such as asthma. Insulin may be provided in quantities of about 4 mg or less, typically about 3.6 mg of pure insulin. The dry powder may be inserted into a dose container/drug compartment in a "compressed" or partially compressed manner or may be provided as free flowing particulates.

Some embodiments of the invention are directed to inhalers that can deliver multiple different drugs for combination delivery. Thus, for example, in some embodiments, some or all of the dose containers may include two different drugs or different dose containers may contain different drugs configured for dispensing substantially concurrently.

The inhalers can be configured to provide any suitable number of doses, typically between about 30-120 doses, and more typically between about 30-60 doses. The inhalers can deliver one drug or a combination of drugs. In some embodiments, the inhalers can provide between about 30-60 doses of two different drugs (in the same or different unit amounts), for a total of between about 60-120 individual unit doses, respectively. The inhaler can provide between a 30 day to a 60 day (or even greater) supply of medicine. In some embodiments, the inhalers can be configured to hold about 60 doses of the same drug or drug combination, in the same or different unit amounts, which can be a 30 day supply (for a twice per day dosing) or a 60 day supply for single daily treatments.

Certain embodiments may be particularly suitable for dispensing medication to respiratory patients, diabetic patients, cystic fibrosis patients, or for treating pain. The inhalers may also be used to dispense narcotics, hormones and/or infertility treatments.

The dose container assembly and inhaler may be particularly suitable for dispensing medicament for the treatment of respiratory disorders. Appropriate medicaments may be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person of skill in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Some particular embodiments of the dose container assembly and/or inhaler include medicaments that are selected from the group consisting of: albuterol, salmeterol, fluticasone propionate and beclometasone dipropionate and salts or solvates thereof, e.g., the sulphate of albuterol and the xinafoate of salmeterol. Medicaments can also be delivered in combinations. Examples of particular formulations containing combinations of active ingredients include those that contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

Important attributes of DPI devices can be: 1) the ability to protect the dry powder from moisture ingress; 2) the number of doses contained within the inhaler; and 3) the overall size of the inhaler. In addition, it may be advantageous to fit the largest practical number of doses within the smallest possible inhaler. However, it may be necessary for individual doses to be spaced apart from each other to allow sufficient seal area and material thickness for moisture protection of the powder. One solution may be to use a dose ring with dose containers spaced equidistant from each other at two different radii, also referred to as a "staggered concentric" arrangement of doses.

Unfortunately, a challenge with a staggered concentric dose ring can be how to access each dose container for opening and inhalation. If all of the outer dose containers are opened first, followed by all inner dose containers, this may require an indexing device that will index a "half step" in order to effect the transition from the outer to inner ring of dose containers, but index a "full step" for all other dose containers. This indexing functionality may be difficult to achieve in inhaler devices. An alternative may be to create dose rings with a special arrangement of dose containers on the dose ring. Unfortunately, this may complicate the automated handling and filling of the powder into the dose ring.

Turning now to the figures, FIGS. 1A-1C illustrate an example of a multi-dose inhaler 10 with a cover 11, inhalation port 10*p*, and upper and lower housing portions 12, 13. However, this inhaler configuration is shown merely for completeness and embodiments of the invention are not limited to this inhaler configuration as other form factors, covers and inhalation port configurations may be used. In FIG. 1A the cover 11 is in a closed position. In FIG. 1B the cover 11 has been moved to an open or operational position. FIG. 1C illustrates the user lever 260 of an actuator mechanism moved from a first position (FIG. 1B) to a second position, as will be described below.

FIG. 2A illustrates a dose container assembly 20 with a dose ring or disk 30 having a plurality of dose containers 30*c*. As shown in FIGS. 2B and 2E, in some embodiments, the dose ring or disk 30 can include a plurality of circumferentially spaced apart through apertures 30*a* that form a portion of the dose containers 30*c*. As shown in FIG. 2E, the dose containers 30*c* can be defined by dose container apertures 30*a* and upper and lower sealants 36, 37.

As shown, the dose container assembly 20 includes a lower airway disk 40 and an upper airway disk 50. In other embodiments, the dose container assembly 20 can include the dose container disk 30 and only one of the lower airway disk 40 or the upper airway disk 50. In such a configuration, another type of airway can be used for the other side of the disk 30, such as, but not limited to, a fixed or "global" upper or lower airway can be used with the individual airways provided by either an upper or lower airway disk 50, 40. Also, it is contemplated that the upper and lower airway disks 50, 40 described herein can be reversed for normal operation (or inadvertently for atypical operation) so that the lower airway disk is the upper airway disk and the upper airway disk is the lower airway disk.

As shown in FIGS. 2A and 2B, the lower and upper airway disks 40, 50, respectively, include a plurality of circumferentially spaced apart airway channels 41, 51, respectively. Typically, the disks 40, 50 include one channel 41, 51 for one dose container 30*c*. However, in other embodiments, as shown, for example, in FIG. 2C, a respective airway channel 51, 41 from one or both of the disks 50', 40' can be in communication with two different dose containers 30*c*. This configuration will allow for (simultaneous) combination delivery of dry powder from two containers in a respective airway channel pair (or single) or can allow one dose container $30c_1$ to release dry powder to the airway channel 41 and/or 51, then be used again later for the other dose container $30c_2$. Thus, embodiments of the invention allow for some or all airway channels 41, 51 to be used once or twice. Also, while embodiments of the invention are illustrated as releasing only a dose from a single dose container 30*c* during one delivery, other embodiments allow the inhalers to dispense a combination drug so that two or more dose containers 30*c* may use a respective airway channel 41, 51 for delivery.

In some embodiments, the airway channels 41, 51 can define airways that are not able to release dry powder residing in a respective airway channel to a user once the inhaler is indexed again to another position so that the respective airway channel is no longer in communication with the inhalation port 10*p*. The channels can be configured to have "sink traps" to inhibit spillage according to some embodiments of the present invention to provide overdose protection (unless the dual use configuration is used whereby only a single other dose may be released using that airway channel(s) as noted above).

Where two airway disks are used, e.g., both the lower and upper disks 40, 50, the inhaler device 10 can be configured to operate even when inverted and have the same overdose protection feature. Spillage of dry powder from the inhaler 10 as the dose container 30*c* is opened can be influenced by gravity. For example, for a conventional obround or elliptical mouthpiece shape, there are two primary device orientations (right-side-up and upside-down), embodiments of the invention allow for operation of the inhaler device in both orientations. In the embodiment shown, for example, in FIG. 2A, this can be accomplished by having an individual airway section for a respective dose container 30*c* (or dose containers where combination drug delivery is desired) both above and below the target corresponding dose container(s) 30*c*.

FIGS. 2A and 3A illustrate that the dose container disk 30 can include 60 dose containers 30*c* while FIG. 3B illustrates that the dose container disk 30 can include 30 dose containers 30*c*. Greater or lesser numbers of dose containers may be used. FIGS. 2A, 3A and 3B also illustrate that the dose container disk 30 can include at least one indexing notch 34, shown as a plurality of circumferentially spaced apart indexing notches 34. To assemble the assembly 20, a tab on one of the airway disks 40, 50, typically the lower disk 40, includes a radially extending tab 45 (FIGS. 4, 6) that aligns with and engages one of those notches 34 to position the channels 41, 51 in alignment with the dose containers 30*c*. Other alignment means may be used including the reverse of the notch and tab configuration described (e.g., the airway disk can have the notch and the dose container disk can have the tab).

As shown in FIGS. 2B, 3A and 3B, the dose containers 30*c* may be arranged so that they are circumferentially spaced apart in one or more rows. As shown in FIG. 3A, the dose containers 30*c* are arranged in staggered concentric rows, a front row 31 at a first radius from a center of the disk and a back row 32 at a second different radius. As shown in FIG. 3A dose containers 30*c* on each respective row are spaced apart a distance "D" and the offset of the centerlines of those on the back row to those on the front row is "D/2". The dose container disk 30 can be a molded polymer, copolymer or blends and derivatives thereof, or may comprise metal, or combinations thereof, or other materials that are capable of providing sufficient moisture resistance.

The dose container disk 30 can have an outer diameter of between about 50-100 mm, typically about 65 mm and a thickness of between about 2-5 mm, typically about 3 mm. The disk 30 can comprise a cyclic olefin (COC) copolymer. The apertures 30*a* can have a diameter of between about 2-5 mm, typically about 3 mm and the sidewalls 30*w* of the dose containers 30*c* may have an angle or draft of about 1-3 degrees per side, typically about 1.5 degrees, as shown in FIG. 3D, to facilitate removal from a mold (where a molding process is used to form the disk 30). The dose container 30 is configured to be able to protect the powder from moisture ingress, while providing a desired number of doses in a compact overall inhaler size. The individual apertures 30a are spaced apart from each other to allow sufficient seal area and material thickness for moisture protection of the powder.

Figure 2A:
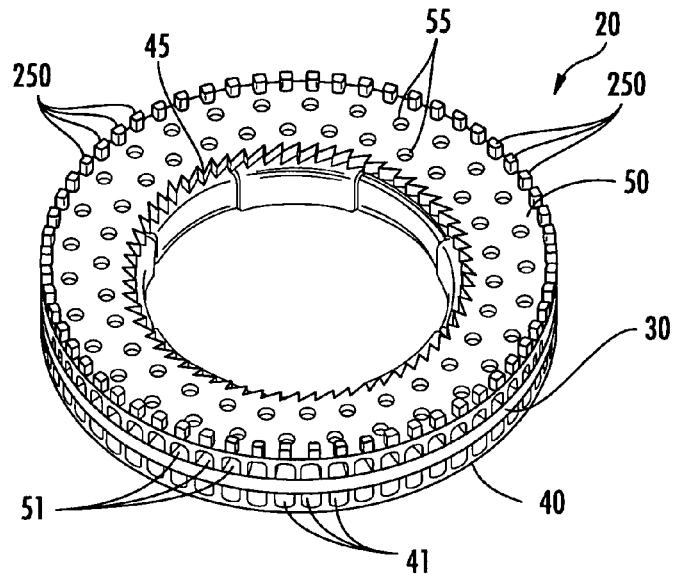
FIG. 2A is a top perspective view of a dose container assembly according to some embodiments of the present invention.
Figure 2C:
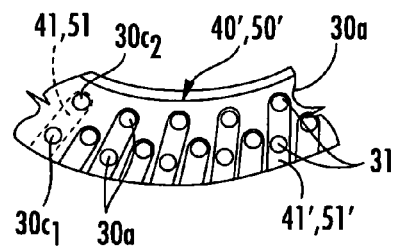
FIG. 2C is a partial cutaway view of airway channels aligned with two dose containers according to some embodiments of the present invention.
Figure 2B:
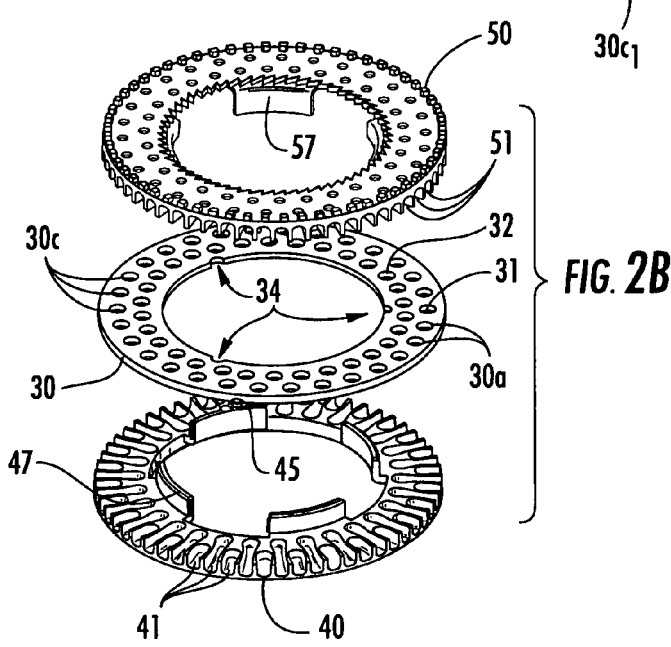
FIG. 2B is an exploded view of the assembly shown in FIG. 2A.
Figure 2D:
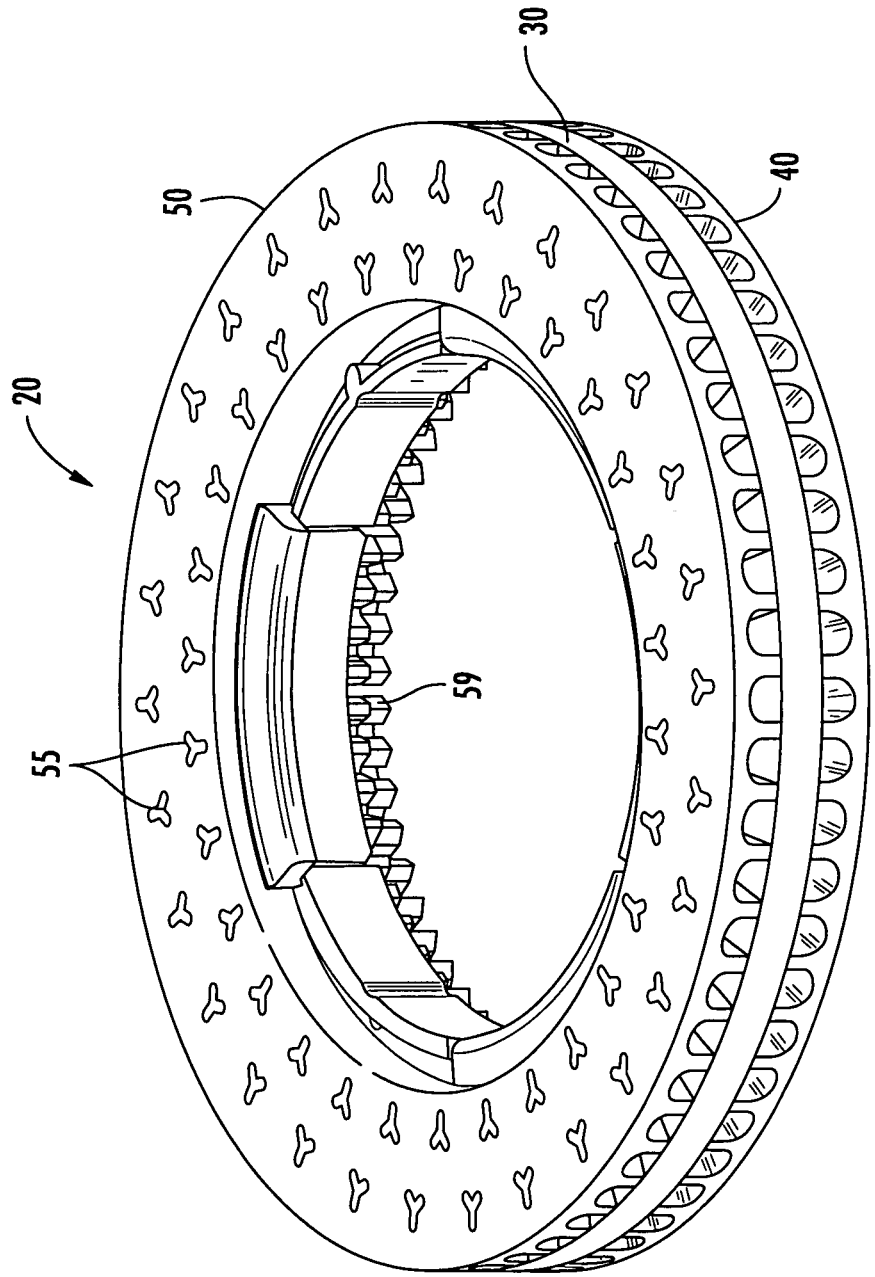
FIG. 2D is a top perspective view of another exemplary dose container assembly according to some embodiments of the present invention.
Figure 2E:
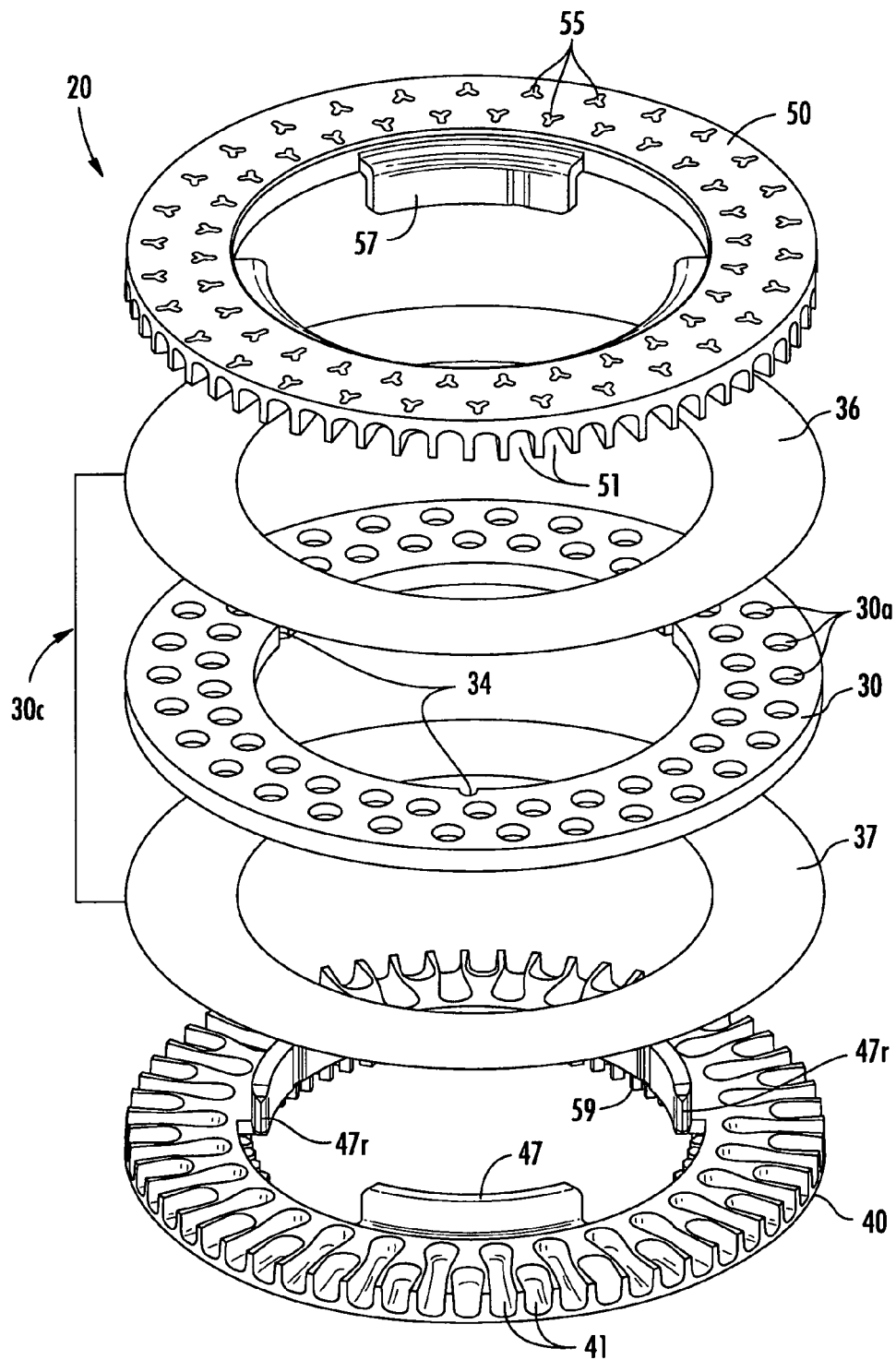
FIG. 2E is an exploded view of the dose container assembly shown in FIG. 2D according to embodiments of the present invention.
Figure 3A:
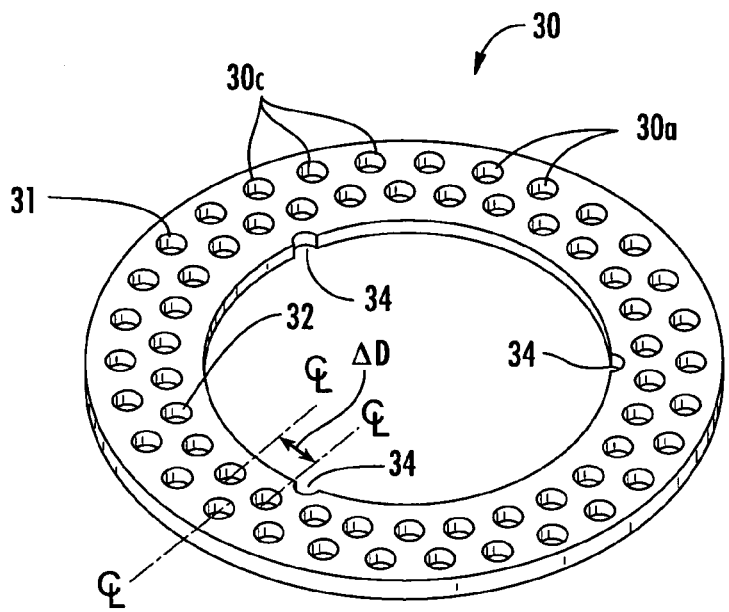
FIG. 3A is a top perspective view of a dose container ring according to some embodiments of the present invention.
Figure 3B:
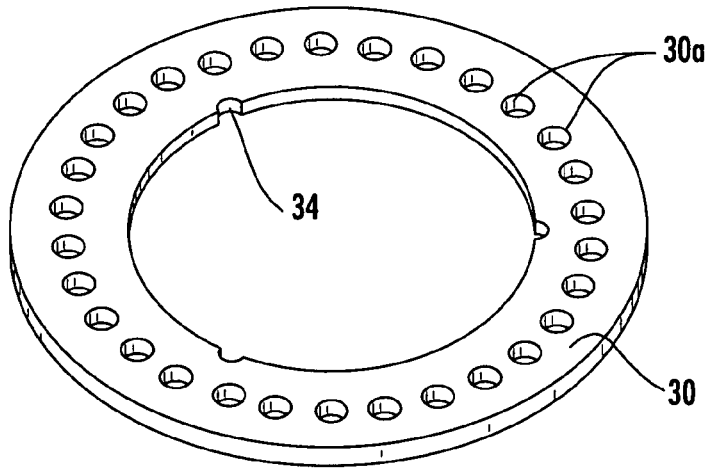
FIG. 3B is a top perspective view of a dose container ring according to some other embodiments of the present invention.
Figure 3C:
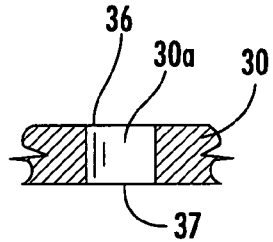
FIG. 3C is a partial cutaway view of a single dose container according to some embodiments of the present invention.
Figure 10A:
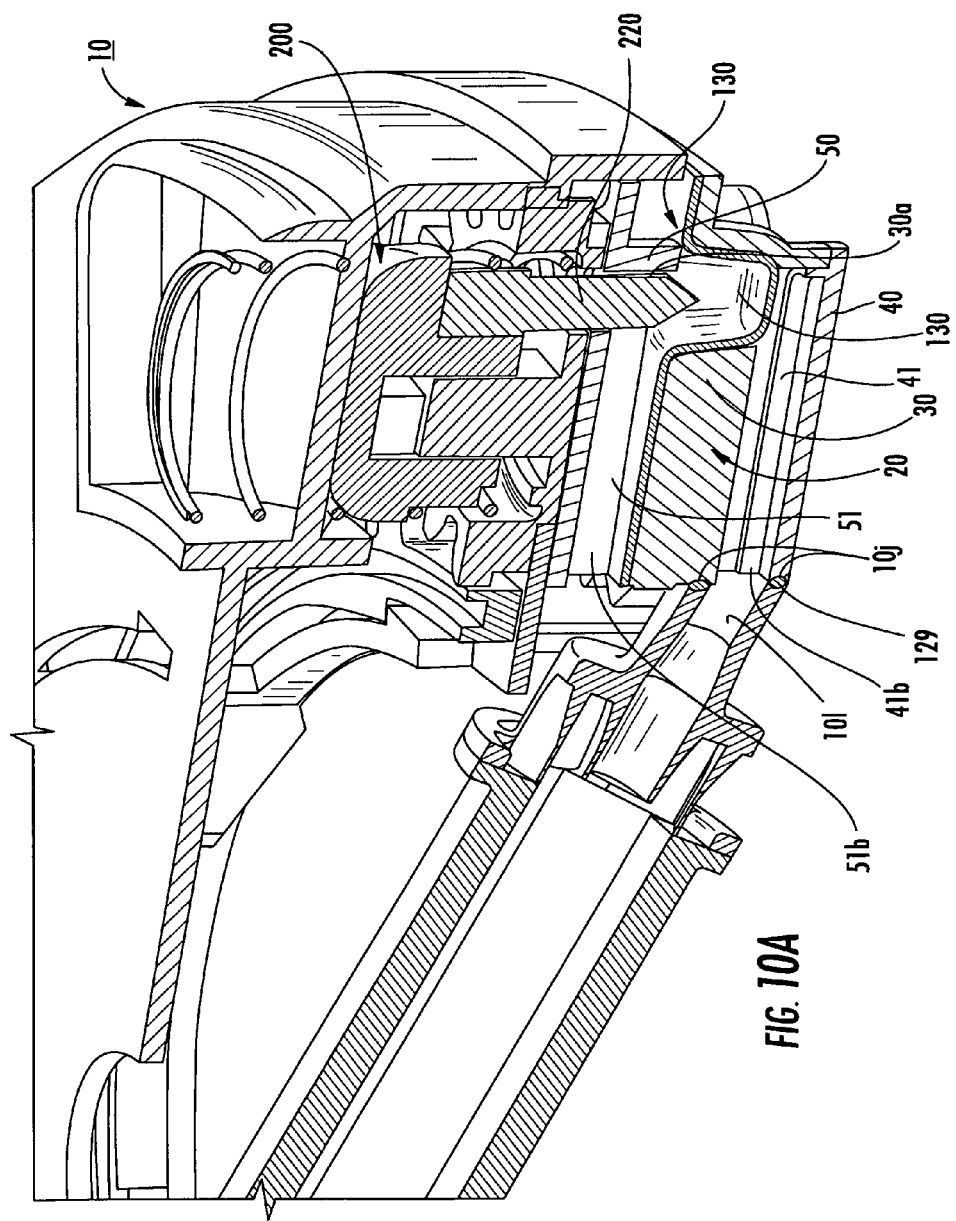
FIG. 10A is a greatly enlarged partial cutaway view of an inhaler with discrete airway channels for each dose container and a long airway path according to some embodiments of the present invention.

Similar to the embodiment shown in FIG. 2E, FIG. 3C illustrates that the dose containers 30c may be defined by apertures 30a sealed by sealant layers 36, 37 over and under the apertures 30a. The sealant can include foil, a polymer and/or elastomer, or other suitable materials or combinations of materials, including laminates. In a dry powder medicament inhaler 10, the drug powder is stored in a closed, moisture-resistant space provided by the dose containers 30c. The sealant layers 36, 37 (where used) may be provided as a substantially continuous ring or may be attached to the dose container disk 30 as individual strips or spots of sealant can be placed over and under the apertures 30a. In other embodiments, sealant is only provided on one primary surface of the dose disk, and the apertures 30a may be closed on one side rather than through apertures (not shown). In yet other embodiments, the dose disk 30 can have a blister configuration 130 (FIG. 10A).

Embodiments of the invention provide a dose container assembly 20 that can provide a suitable seal and facilitate attachment of the airway disks 40, 50 to the dose ring or disk 30. In some embodiments, the dose container disk 30 contains sealants 36, 37 which may be a continuous layer over the upper and lower (primary) surfaces of the dose disk 30 and the upper and lower airway disks 50, 40 can contact the respective sealant and abut the dose disk to allow for a tight fit. The exemplary attachment features shown in FIGS. 2E and 6 can reduce air leakage by allowing a close fit of the airway disks 40, 50 to the dose ring 30. The disks 40, 50 can sandwich the dose ring 30 and the dose ring can act as the "stop" to set the depth of engagement of the assembly features on the airway disks 40, 50. Embodiments of the invention provide a feature to index the airway disks 40, 50 relative to the dose ring 30, and some simple frictional engagement members, such as, but not limited to, "crush ribs", on one or both of the airway disks 40, 50 to secure their attachment to each other as will be discussed further below.

Figure 4A:
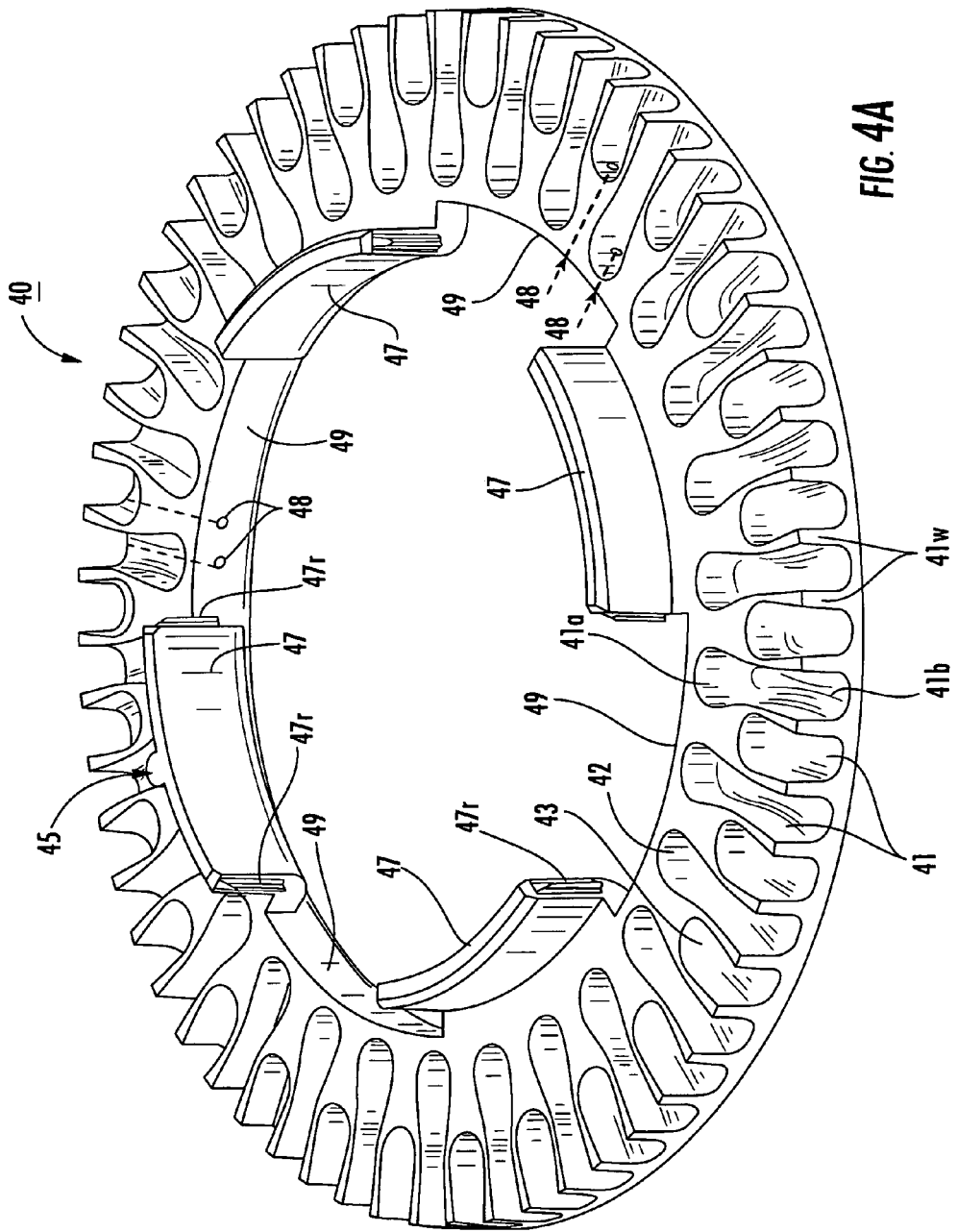
FIG. 4A is a greatly enlarged top perspective view of a lower airway disk according to some embodiments of the present invention.

FIG. 4A illustrates an example of a lower airway disk 40. As shown, the disk 40 defines a plurality of circumferentially spaced apart channels 41. For the staggered concentric dose container configuration, the disk 40 can include alternating long and short airway channels 42, 43, respectively. Each channel 41 includes opposing end portions 41a, 41b, one (substantially or entirely) closed end portion 41a typically positioned adjacent the dose container 30c and one open end portion 41b. The open end portion end portion 41b can merge into and/or is positioned adjacent the exit port 10p and/or mouthpiece 10m (FIGS. 7A-7C) and/or a make-up air port or channel. The intake and flow can be in either direction and the open end 41b can be configured to face either the inner or outer perimeter of the disk 40 (e.g., be either positioned radially innermost or radially outermost on the disk 40). The channels 41 include upwardly extending sidewalls 41w with adjacent pairs of the long and short channels sharing one of the sidewalls 41w. Optionally, as shown by the broken line with respect to feature 48 in FIG. 4A, the channels 41 can include a small bleed hole 48 that allows air to enter but is sized to inhibit dry powder from exiting therefrom (the bleed holes 48 are shown only with a few of the channels 41 for ease of illustration).

Figure 4B:
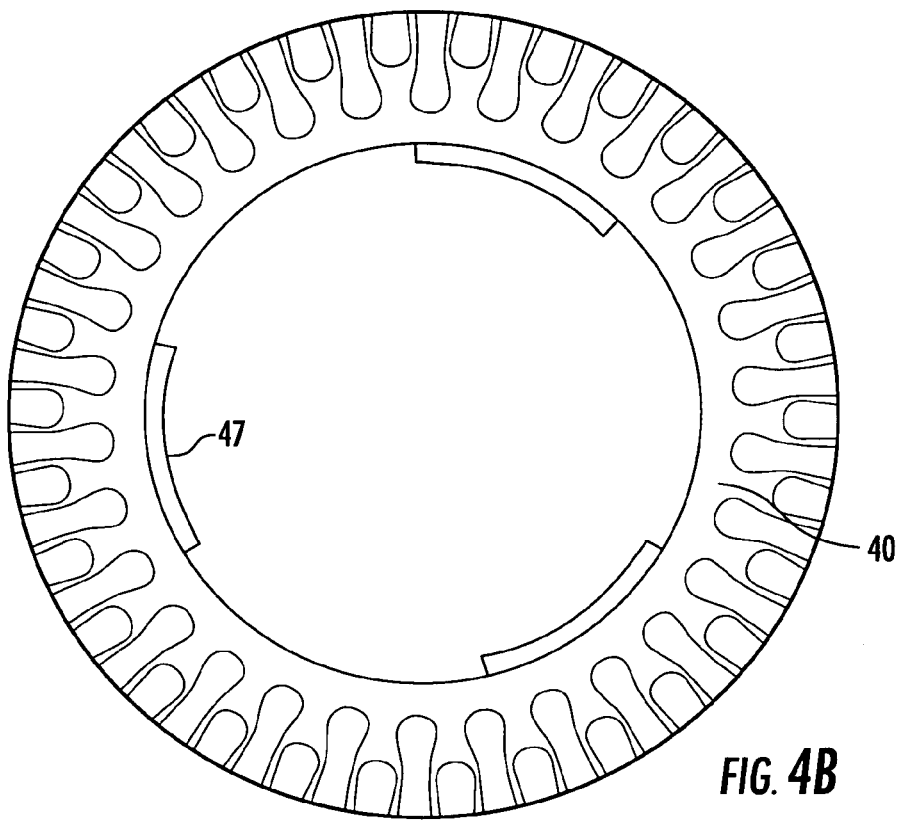
FIG. 4B is a top view of a lower airway disk according to some embodiments of the present invention.

FIGS. 4A and 4B illustrate that the disk 40 can include circumferentially spaced apart upwardly extending tabs 47, one of which includes the radially extending tab 45 discussed above. The disk 40 can also include circumferentially extending recesses which align with tabs on the upper airway disk 50 to sandwich the dose disk therebetween. The tabs 47 can include crush ribs 47r that matably engage with tabs 57 on the upper airway disk to hold the three piece assembly 20 with sufficient force without requiring any additional attachment means.

Figure 4C:
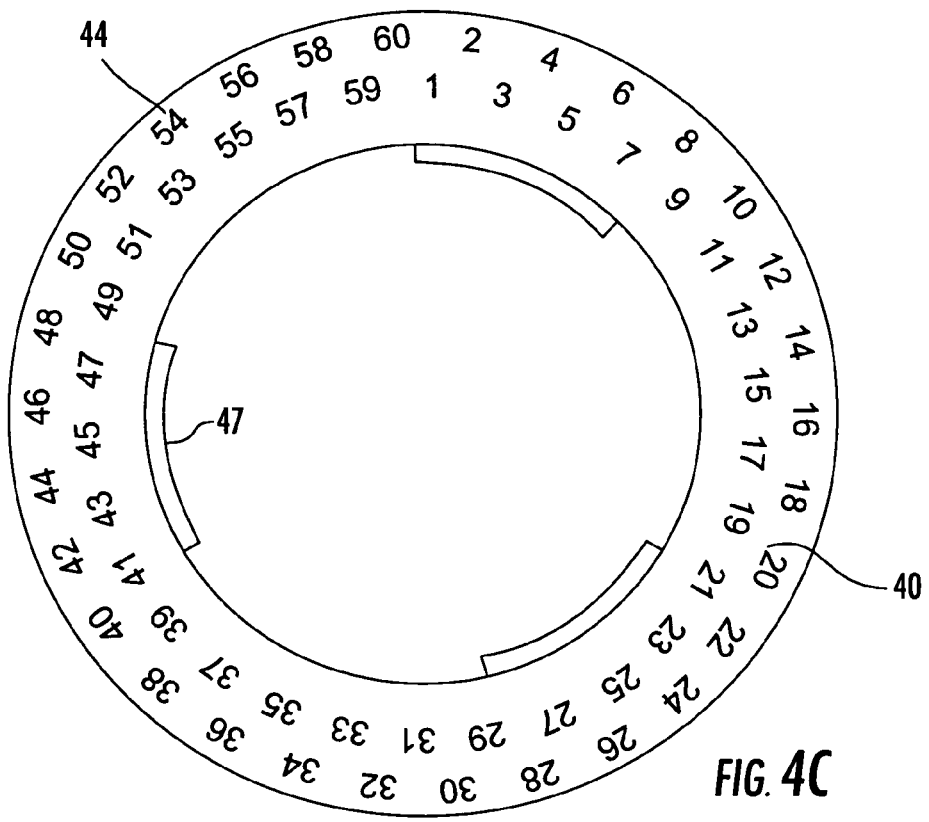
FIG. 4C is a bottom view of the lower airway disk shown in FIG. 4B.
Figure 10B:
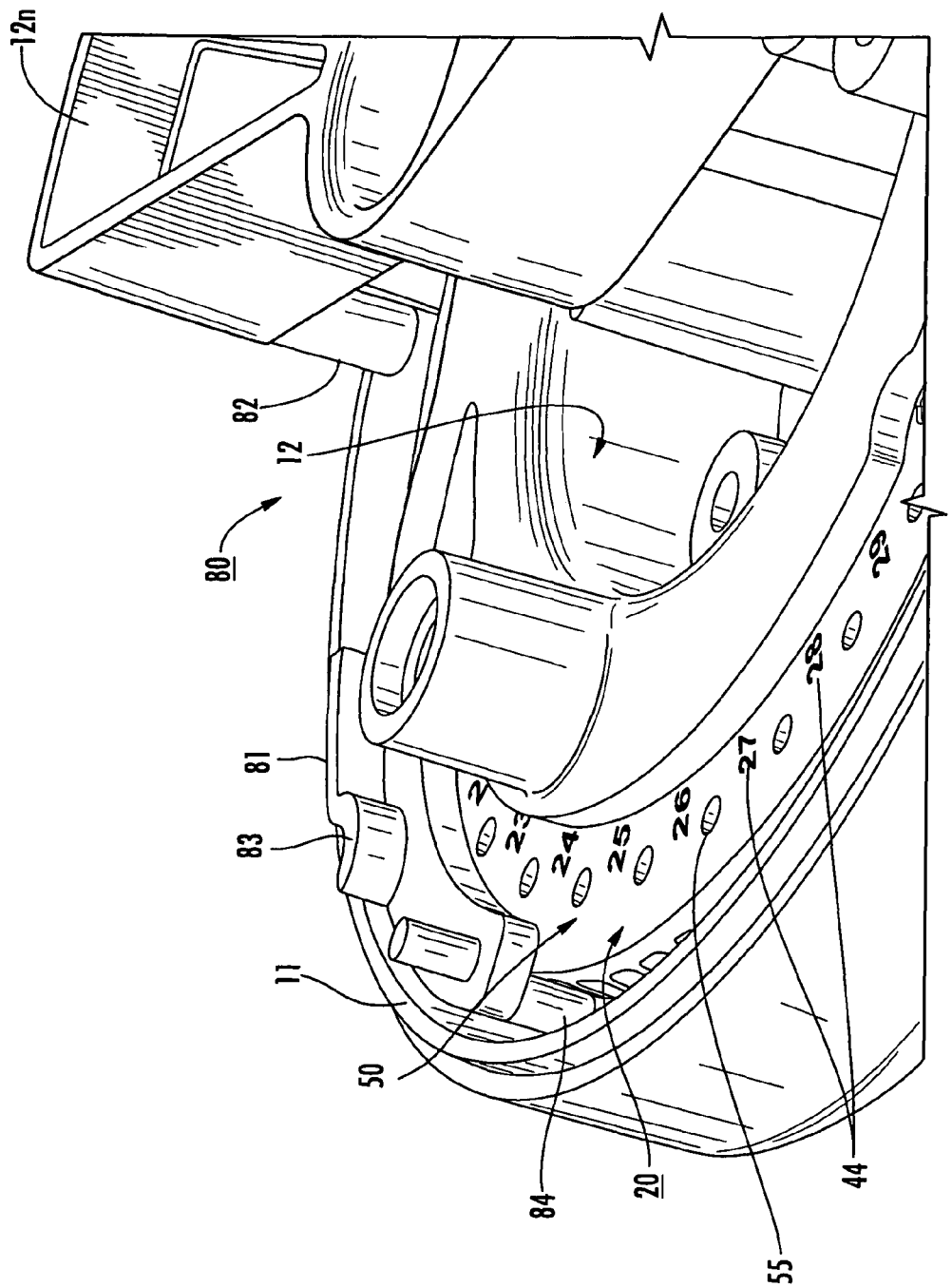

FIG. 4C illustrates that the disk 40 can also include dose indicia 44 so that a user can visually note what dose is being dispensed or a number of doses left in the inhaler. The dose indicia 44 can align with a dose reading aperture in the inhaler housing so that a user can visually assess the dose indicia/information that is visible to a user when a respective dose is indexed or is next to be indexed, to the dispensing position. Dose indicia 44 may also or alternatively be placed on the upper disk 50 and aligned with a dose reading aperture (not shown), or on both disks (also not shown). FIG. 10B illustrates that dose indicia 44 may be placed along the outer perimeter edge of the upper surface of the upper disk 50, and numbered sequentially, but other patterns may be used, depending on the opening sequence (and the number of doses on the disk). In some embodiments, the dose indicia 44 numbering can serially progress to alternate between rows of the dose containers 30 where the dose containers are opened in sequence in alternate rows, e.g., number 1 on the outer row, number 2 on the inner row, number 3 on the outer row (or vice versa) and so on. However, other dose numbering patterns may be used, depending on the opening sequence (and the number of doses on the disk). That is, this numbering may be appropriate where the inhaler is configured to open a dose container in one row, then open an adjacent dose container in the other row (e.g., inner to outer ring or outer to inner ring of dose containers), and repeating this sequence serially, where two rows of dose containers are used. However, other embodiments may open all the inner dose containers or all the outer dose containers, then open the dose containers in the other row or use a different alternating pattern of opening the dose containers on the inner and outer rows, and the dose numbering indicia on the disk 40 and/or 50 can be presented accordingly.

Figure 5A:
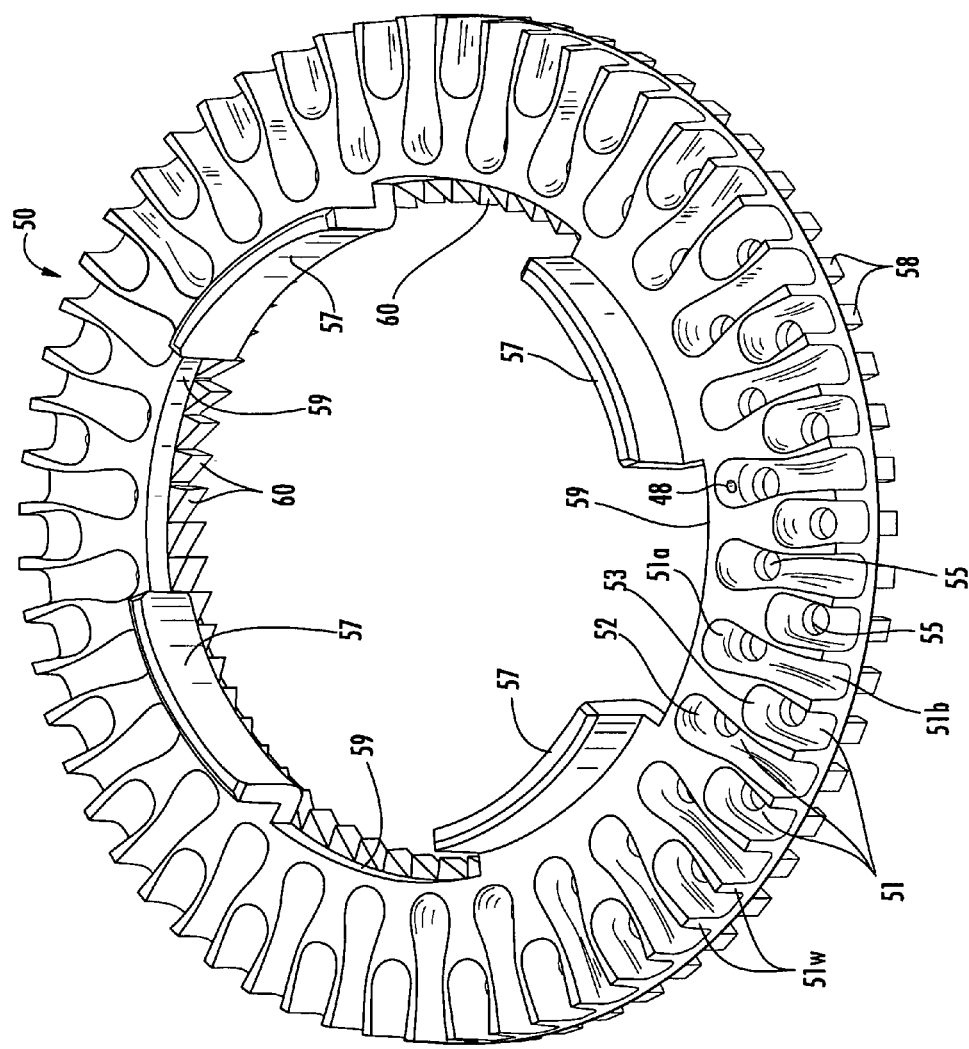
FIG. 5A is a greatly enlarged top perspective view of an upper airway disk according to some embodiments of the present invention.

FIG. 5A illustrates an example of an upper airway disk 50. In this embodiment, the upper airway disk 50 is shown inverted from its normal use position (and inverted relative to the orientation shown in FIG. 2A). As shown, the disk 50 defines a plurality of circumferentially spaced apart channels 51. For the staggered concentric dose container configuration, the disk 50 can include alternating long and short airway channels 52, 53, respectively. Each channel 51 includes opposing end portions 51a, 51b, the closed or substantially closed portion 51a is typically positioned adjacent the dose container 30c. The intake and flow can be in either direction and the open end 51b can be configured to face either the inner or outer perimeter of the disk 50 (e.g., be either positioned radially innermost or radially outermost). The other (open) end portion 51b merges into and/or is positioned adjacent the exit port 10p and/or mouthpiece 10m and/or make-up air port or channel. The channels 51 include outwardly extending sidewalls 51w with adjacent pairs of the long and short channels sharing one of the sidewalls 51w. Optionally, as shown by the broken line with respect to feature 48 in FIG. 5, the channels 51 can include a small bleed hole 48 (shown with only a few channels for ease of illustration) that allows air to enter but is sized to inhibit dry powder from exiting therefrom.

As also shown in FIG. 5A, each channel 51 can include an aperture 55 that is configured to reside over a respective dose container 30c with the upper sealant layer 36 of the dose container 30c residing under the aperture 55. The apertures 55 allow a piercing (e.g., slicing or puncturing) member (e.g., 220, FIG. 13D) to extend through the aperture and open the sealant layers 36, 37 (FIG. 3C). As shown in FIG. 5A, the upper disk 50 can also include one or more of indexing ribs 58 and/or inner perimeter gear teeth 60 or other features that can index the disk within the inhaler to rotate the disk to provide the different dose containers 30c to a dispensing position and/or position a piercing mechanism over the target dose container for dispensing to open the dose container 30c. In other embodiments, one or both of these rotating and positioning mechanisms (or different features) can be provided on the lower disk or the dose disk (not shown).

Figure 5B:
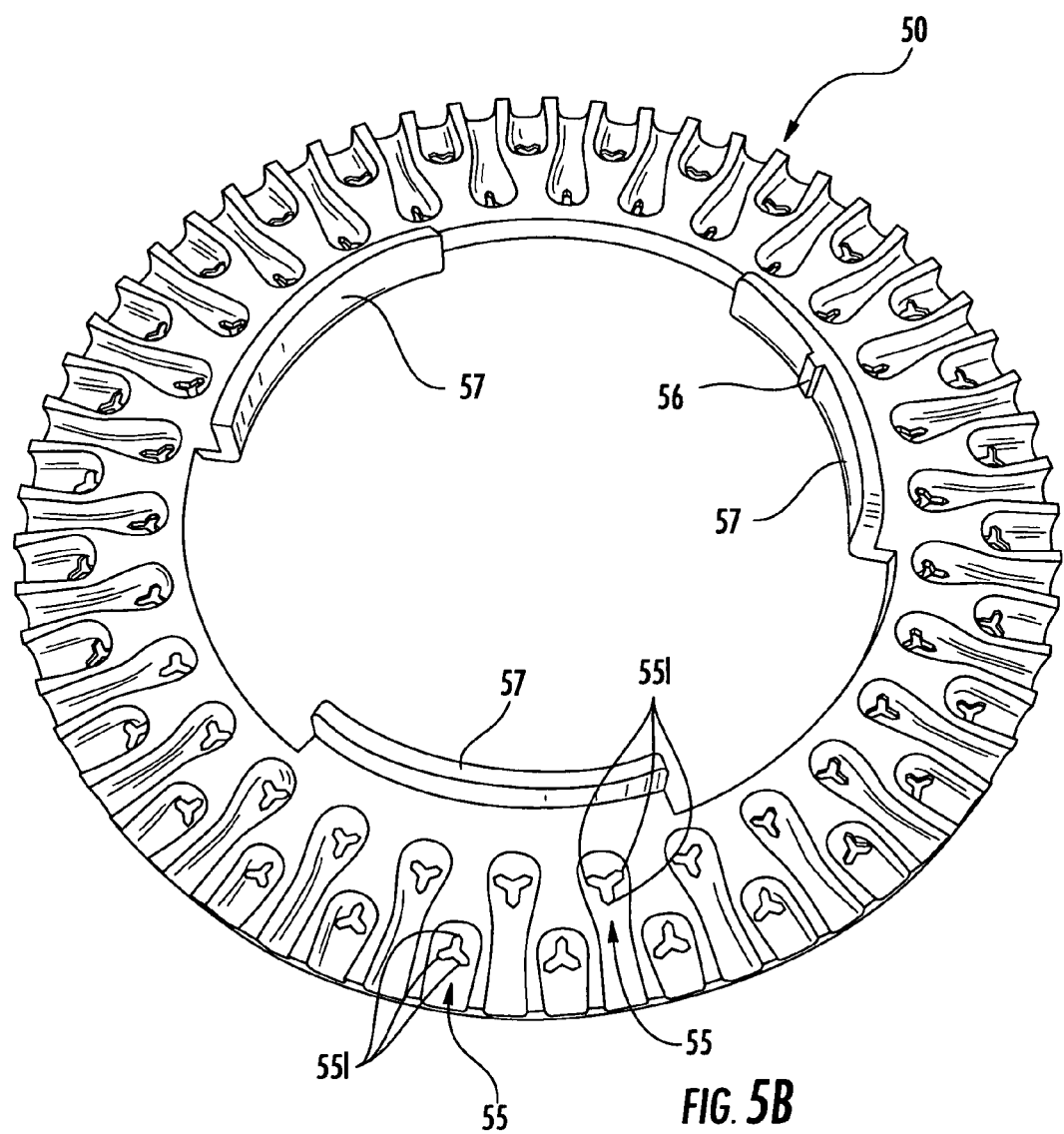
FIG. 5B is a greatly enlarged perspective view of an upper airway disk according to other embodiments of the present invention.

FIG. 5B illustrates that the disk 50 can include three tabs 57 instead of four as shown in FIG. 5A (the lower airway disk 40 can also include three tabs instead of four in this embodiment, see FIGS. 4B, 4C). One of the tabs 57 can have a vertically extending orientation rib 56, shown on an inner perimeter surface of the tab 57. In some embodiments, the orientation rib 56 on the upper disk 50 cooperates with a piercing frame associated with the piercing mechanism fixed in the inhaler housing so that the orientation rib 56 aligns to the frame to set a correct initial position according to dose number (e.g., 1) and prevents indexing past the number of doses in the disk assembly 20. Stated differently, the orientation rib 56 cooperates with the inhaler housing to set an initial position of the disk assembly 20 and also stops the disk assembly from rotating around more than once.

FIG. 5B also illustrates that the apertures 55 can be configured with a geometry that corresponds to the shape of the piercer 220. The apertures 55 can be configured to closely surround the piercer 220. The piercer 220 can be a fluted piercer. As shown, the aperture 55 has three lobes 55l to snugly matably receive a correspondingly shaped three lobe (fluted) piercer 220 (FIG. 14D). The lobes 55l can be in a different orientation in the inner row versus the outer row, e.g., rotated 180 degrees.

FIGS. 2A and 6 illustrate the dose container assembly 20 integrally attached together. FIGS. 2B, 4A, and 5A illustrate the exemplary disk components, 30, 40, 50. The tabs 57 of the disk 50 fit into spaces 49 of the disk 40 and the tabs 47 of the disk 40 fit into spaces 59 of the disk 50 with the crush ribs 47r firmly abutting the outer edges of tabs 57 to frictionally engage the components together with the dose disk 30 sandwiched therebetween with a flush fit via a relatively easy "press-fit" assembly method. The dose container disk 30 is aligned with the upper and lower airway disks via the (radially outward extending) tab 45 that engages one of the alignment notches 34 of the dose container ring 30 as discussed above. However, other alignment features or indicia may be used as well as other attachment configurations.

The upper and lower airway disks 50, 40 (where both are used) can be attached to the dose container disk 30 so as to reduce any gaps in the airway path defined thereby. The disk 30 can be a stop for attachment features on the airway disks 40, 50. The disk 30 with the sealants 36, 37 can have substantially planar upper and lower primary surfaces without requiring any attachment features. The lower portion of the upper airway disk 50 and the upper portion of the lower airway disk 40 can snugly reside against the respective opposing primary surfaces of the dose container disk 30 so that the attachment features/components are only on the upper and lower disks 50, 40 allowing for a snug and sufficiently air-tight interface between the disks 30, 40, 50 without gaps created by tolerances in other build configurations. The press-fit attachment without use of adhesives while providing for the substantially air-tight interface can be advantageous and cost-effective. However, as noted above, other attachment configurations may be used, including, for example, ultrasonic welding, adhesive, laser weld, other friction fit and/or matable configurations, the use of seals (O-rings, gaskets and the like) between the connection regions of the walls of the airway channels facing the dose container 30c and the sealant layers 36, 37 over and/or under the dose containers 30c of the disk, including combinations thereof, and the like.

Figure 7A:
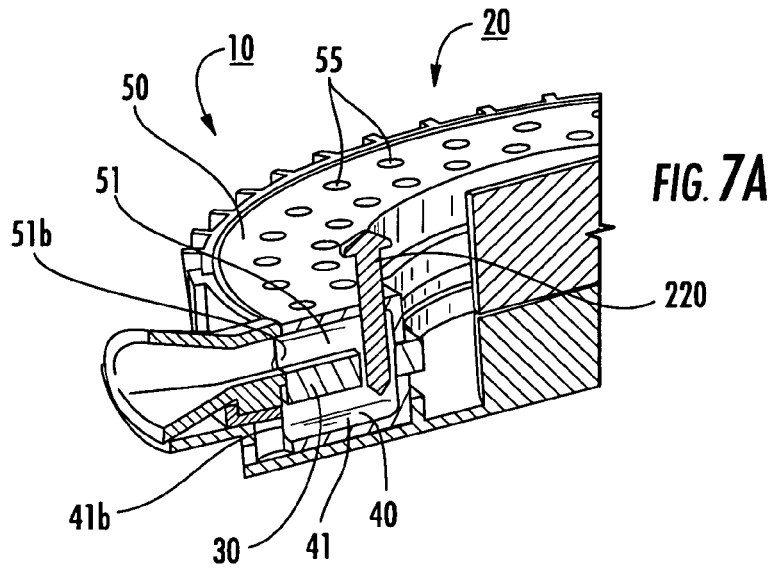
FIGS. 7A-7C are partial cutaway views of a dose container assembly in an inhaler cooperating with a piercing mechanism having a three-stage operation sequence according to some embodiments of the present invention.
Figure 7B:
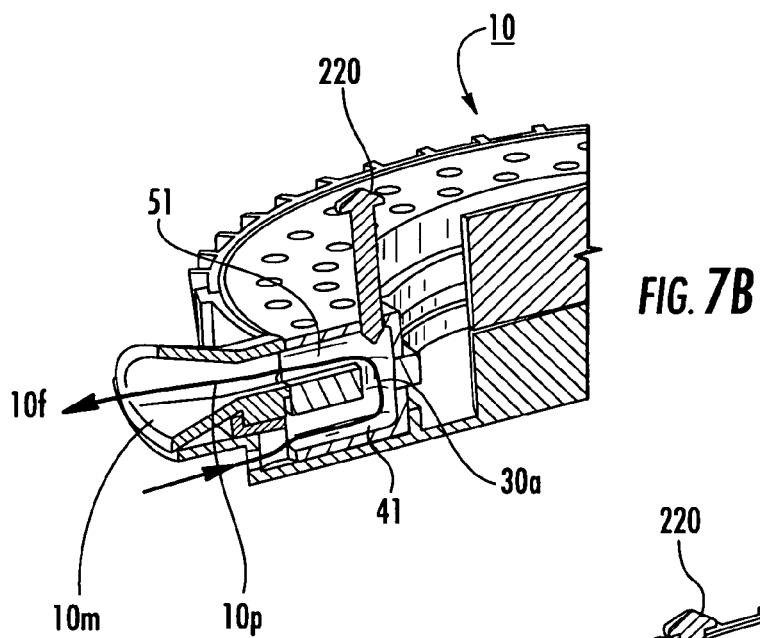
Figure 7C:
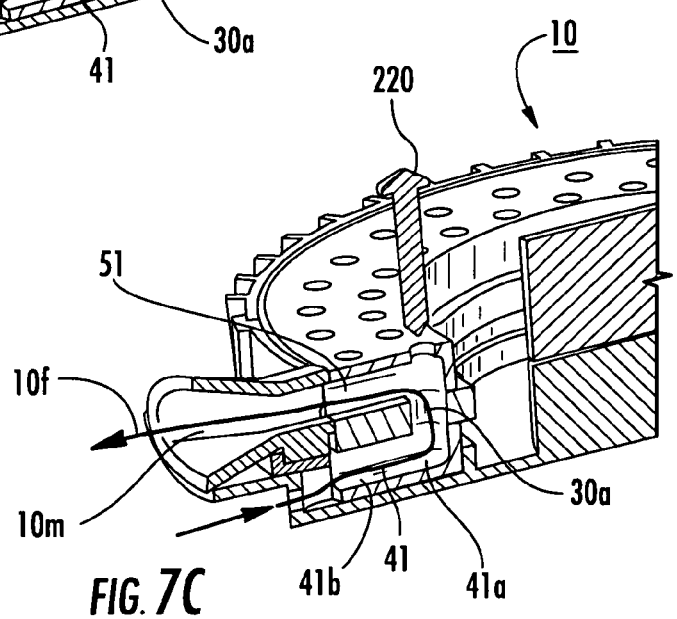

As shown in FIGS. 7A-7C, in operation, pairs of upper and lower aligned channels 41, 51 can reside over and under a respective dose container 30c and are in fluid communication via the opened dose container 30c and aperture 30a. That is, as shown in FIG. 7A, a piercing member 220 advances to pierce the upper and lower sealant layers 36, 37, respectively (FIG. 3C). The piercing member 220 can be configured to extend and remain in the lower airway channel or may (partially or fully) retract before the dispensing after opening the lower sealant. Also, although shown as extending down to pierce the sealant layers, the piercing member 220 can be configured to extend upward from the bottom. Either way, the piercing member 220 can be configured to occlude the aperture 55 in the upper (or lower disk).

As shown in FIG. 7B, the piercing member 220 can then partially or fully retract, or stay extended in the lower (or upper) airway channel, depending on the configuration of the mechanism, but is typically configured to plug and/or cooperate with a member that can plug the aperture 55 of the upper disk 50 (or lower disk 40 if piercing from the bottom) or otherwise occlude this passage 55 so that the piercing member 220 and/or cooperating member substantially blocks, occludes (and/or seals) the aperture/opening 55 (FIGS. 2A, 5). In this way, if the inhaler is inverted, powder is prevented from spilling out of the channel 51 because of the blockage provided by the piercing member 220. The airflow path 10f may be any direction from above to below the dose container 30c or vice versa or from the inner perimeter to the outer or vice versa, shown for example only in FIG. 7B by the arrow to allow air to flow through the bottom channel up through the aperture 30a and out the top channel 51 to the mouthpiece 10m. It is also noted that the exit or open end portion of the channel 41b, 51b may face the inner perimeter rather than the outer perimeter of the disc assembly 20 as shown in FIGS. 7A-7C (see, e.g., FIG. 10A).

After dispensing, the piercing member 220 is fully retracted as shown in FIG. 7C and the dose container assembly 20 can be rotated to a dispensing position and/or the piercing member 220 can be activated to open a different dose container 30c. In operation, the dose container assembly 20 can be radially pushed outward to seal or provide a snug exit path for the airway channel 41 and/or 51 against the mouthpiece 10m. FIG. 10A illustrates that a seal 129, such as an O-ring may be used to provide a sufficiently air-tight path between the airflow exit path 10/(or short path 10s and/or mouthpiece 10m) and the disk assembly 20. Other airpath seal or closure configurations may be used.

FIGS. 10B-10E illustrate an embodiment of the inhaler 10 that can bias the disk 20 toward the mouthpiece 10m using a lever assembly 80 that can facilitate an accurate, repeatable position of the disk 20 for piercing, as well as control air leakage at the mouthpiece joint 10j. With regard to air leakage, embodiments of the inhaler provide a tight connection that is temporally synchronized with the time of inhalation, while at other times, e.g., during indexing of the disk 20, the inhaler can allow a looser fit which facilitates rotation of the disk 20 in the inhaler 10. In this embodiment, the mouthpiece 10m resides on the outer perimeter of the disk assembly 20 with the exit ports of the disk assembly 20 also residing on the outer perimeter of the disk assembly.

Figure 10D:
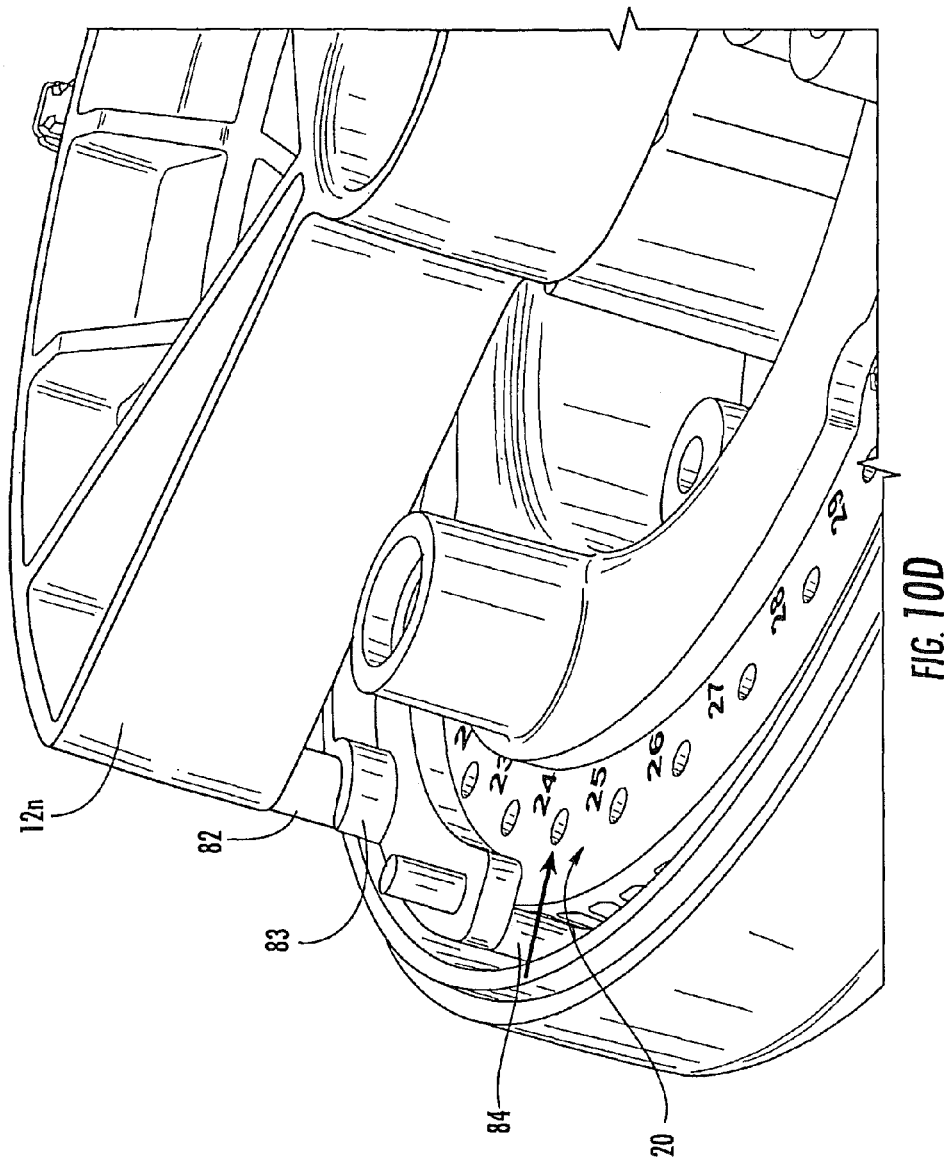
Figure 10E:
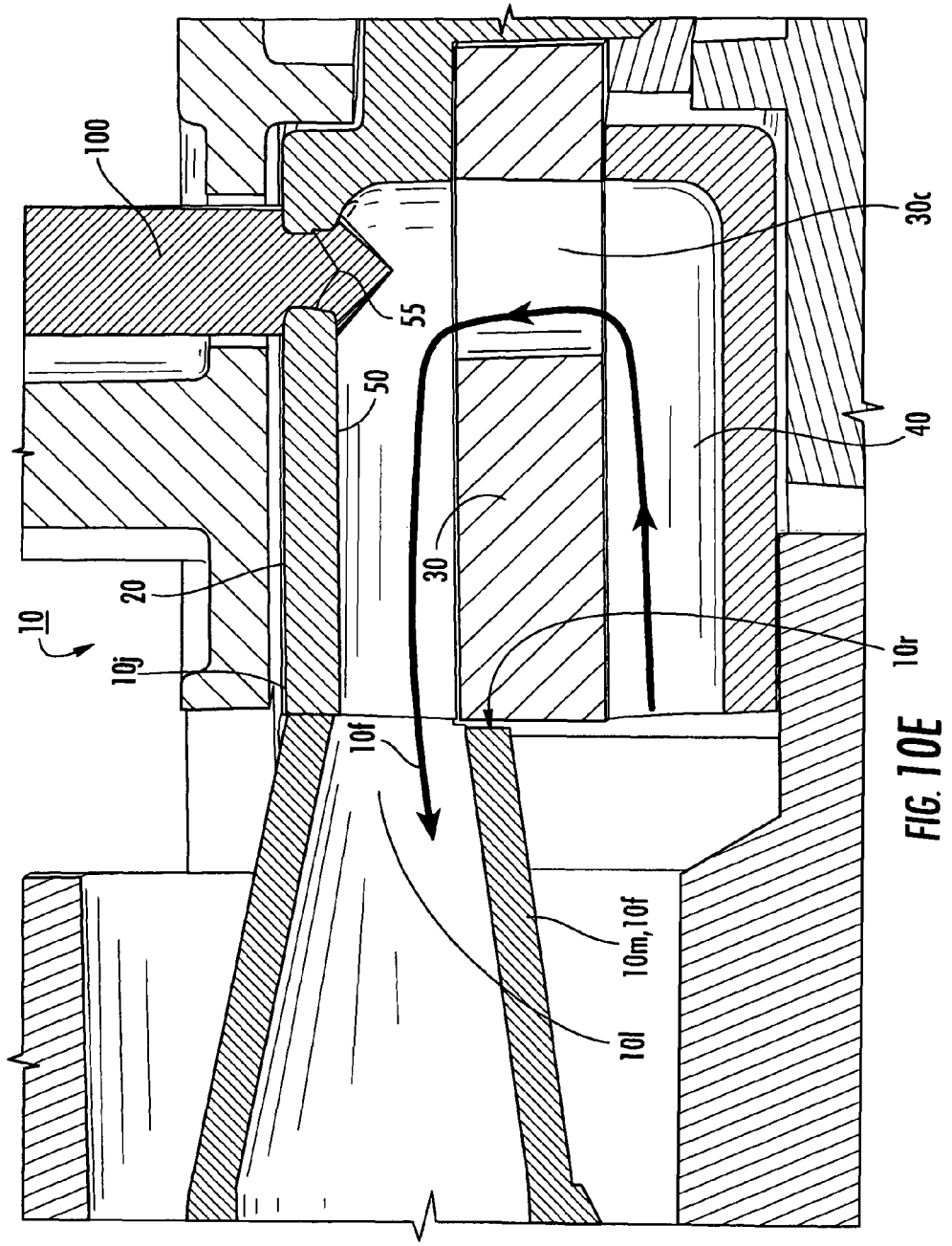
FIG. 10E is a greatly enlarged cutaway view of an airflow path in an inhaler and secure joint provided by the mechanism in FIGS. 10B-10D according to embodiments of the present invention.

As shown in FIG. 10B, the lever assembly 80 includes a lever arm 81 that communicates with an upper surface of the upper airway disk 50 and extends down a distance to reside closely spaced to an outer perimeter of the disk assembly 20. The lever assembly 80 also includes a finger 82 that resides above the disk assembly 20 and extends down toward the disk assembly 20. The lever assembly 80 also includes a loading post 84 that resides proximate an outer perimeter of the disk assembly 20. The lever arm 81 includes a recess 83 that is configured to receive the finger 82. As the finger 82 resides in the recess 83, the post 84 pushes the disk assembly 20 radially inward to cause a tight joint 10*j* at the time of inhalation (FIG. 10E). The recess 83 can have an open perimeter shape and the finger 82 can slidably enter and exit therefrom. The lever arm 81 can define a ramp (inclined in the direction toward the recess 83) that slidably engages the finger 82 and directs the finger 82 to move toward the recess 83.

The lever assembly finger 82 is attached to lever 12*n* and rotates with respect to the frame 12 in the inhaler housing, typically upon user actuation of the lever 12*n*. When the lever 12*n* is returned from "actuated" (dosing) position, the finger 82 is pulled out of the recess 83 so that the disk assembly 20 is free to rotate to index to a next dispensing position.

Typically during inhalation, the loading post 84 resides radially opposite (substantially diametrically opposed to) the mouthpiece 10*m*. The lever arm 81 and post 84 do not rotate. This component is affixed to a frame 12 that is attached to the inhaler housing. The finger 82 rotates with respect to the frame 12 (and the lever arm 81).

As shown in FIG. 10B, the finger 82 does not contact the lever arm 81 during this portion of the stroke cycle of the lever assembly 80 to allow for free rotation during indexing. FIG. 10C illustrates the finger 82 moving toward the recess 83. FIG. 10D illustrates the finger 82 in the recess 83 to bias the disk assembly 20 toward the exit flow path member 10*fm*. At the moment of inhalation, the finger 82 is advanced to its fullest extent of travel. Indexing (rotation) of the disk assembly 20 occurs while the finger 82 is elsewhere in its travel path (arm stationary). Therefore, as shown by the arrow in FIG. 10D, the lever assembly 80 can bias the disk assembly 20 while the finger 82 is at the far extent of travel to seal the joint 10*j* at the proper time (inhalation), while allowing free movement during indexing (typically also unbiased the rest of the time).

It is recognized that, during manufacturing, there may be a tolerance-induced mismatch between the diameters of the dose disk 30 and the upper airway disk 50 of the disk assembly 20. As shown in FIG. 10E, inner or outer sidewall surfaces (shown as outer sidewall surfaces) of both of these disks, 30, 50 contact the mouthpiece 10*m* when the disk assembly 20 is biased against it. Thus, as shown in FIG. 10E a small relief 10*r* can be cut or otherwise formed into the proximate or abutting surface of the an exit flowpath member 10*fm* (which may be the mouthpiece 10*m*) at a location that coincides with the dose disk 30 to assure that the upper airway disk 50, which has the greater amount of contact surface, is always the part to contact the mouthpiece or exit flowpath member 10*fm* in communication with the mouthpiece 10*m*.

Figure 1B:
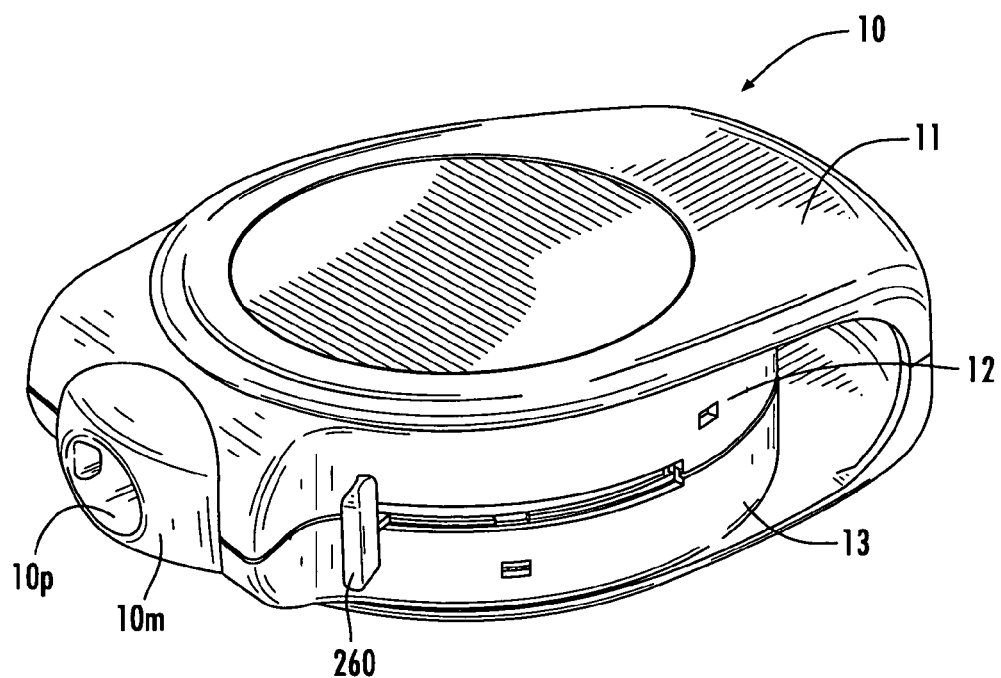
FIG. 1B is a front perspective view of the inhaler of FIG. 1A with the cover moved to an open or operational position.

The inhaler 10 can include a user-accessible actuator such as a lever, knob, switch, slider, crank, pushbutton or other mechanical and/or electromechanical device that can index the dose ring or disk 30 to rotate the assembly 20 to place one or more dose containers 30*c* (FIG. 2B) in a dispensing position in an inhalation chamber in fluid communication with the inhalation port 10*p* (FIG. 1B) and/or cause a piercing member 220 (FIGS. 7A-7C) to open a dose container 30*c* in the front row, then the back row (or vice versa) to release medicament to an inhalation air flow path for inhalation by a user (as will be discussed further below). To release the powder for inhalation, the sealed dose container 30*c* is opened and connected to an airway 41 and/or 51 which is in turn connected to the inhaler mouthpiece 10*m* (see, e.g., FIGS. 7A-7C, 10E). After the drug falls into the channel 41 or 51 (depending on which orientation the inhaler is in), this is a "used" channel and the drug therein is either delivered (if the user inhales properly and timely) or isolated (if the user does not inhale and closes the mouthpiece or otherwise causes the indexing of the disk assembly 20), and the "used" channel is indexed with the opened dose container 30*c* so that it cannot be used again or so that it is used again for only the other dose container in the shared channel (as discussed with respect to FIG. 2C). Any powder remaining in the opened dose container is separated from the airway when the next dose container is indexed into position.

In some embodiments, the portion of the airway provided by the airway channel 41 or 51 adjacent to each dose container 30*c* is unique to that individual dose container 30*c*. In this way, any spillage of powder into the airway will only be available to the mouthpiece and user as long as that dose container is indexed into connection with the primary (mouthpiece) airway. Indexing to the next dose container will also index the adjacent airway section out of connection with the active inhalation airway path, taking any spilled and/or accumulated powder with it.

Figure 8A:
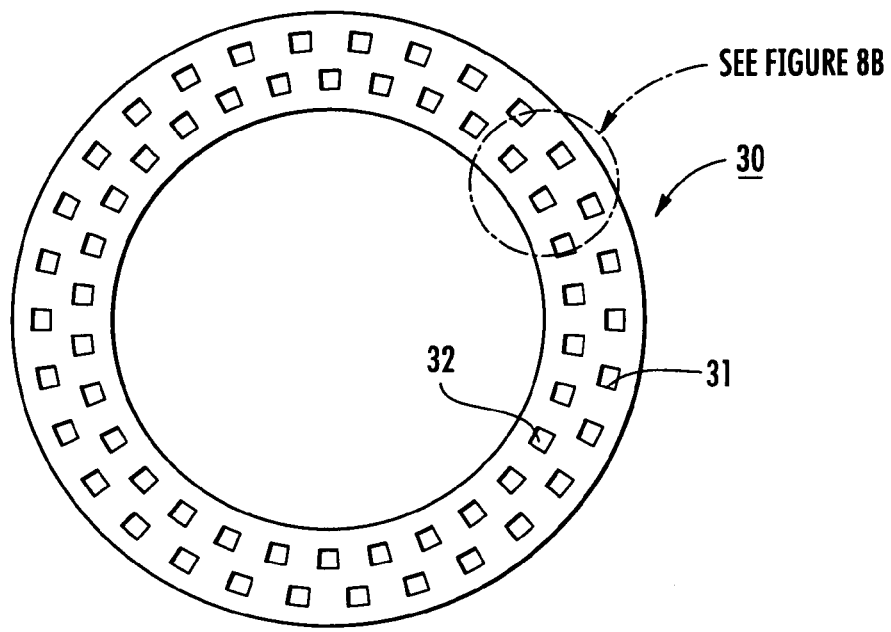
FIG. 8A is a top view of a dose container ring according to some embodiments of the present invention.
Figure 8B:
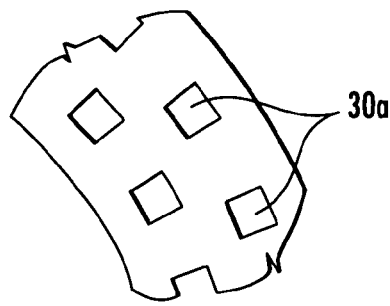
FIG. 8B is a partial enlarged fragmentary view of the ring shown in FIG. 8A.
Figure 9:
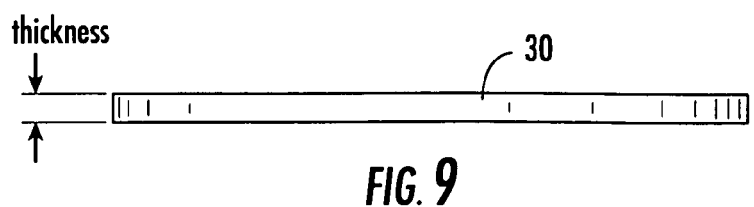
FIG. 9 is a side view of the ring shown in FIG. 8A.

FIGS. 8A, 8B and 9 illustrate an example of a dose container disk or ring 30 with two rows of apertures 30*a* used for dose containers 30*c*. The dose container disk 30 can be relatively thin, such as about 2-4 mm thick. The dose container apertures 30*a* can be configured so that the inner row 32 is at least about 2 mm from the outer row 31 and so that the inner and outer rows of dose containers are spaced inward from the respective perimeters by about 2 mm. This spacing can provide sufficient moisture permeability resistance and/or oxygen resistance.

FIG. 10A illustrates on embodiment of an inhaler 10 with a long exit air path 10*l*. In this embodiment, the airway disks can orient the channels 41, 51 so that the open ends 41*b*, 51*b* face and open to the inside of the disk rather than the outside. FIG. 10A also illustrates that the dose container disk 30 can be configured with blisters 130.

FIG. 10A also illustrates that the piercing mechanism 200 can rotate such that the piercing member 220 can pierce a dose container 30*c* on the inner row, then rotate to pierce the adjacent one 30*c* on the outer row. Examples of piercing mechanisms 200 and piercing members 220 will be described in detail with respect to FIGS. 11, 12A-12B, 13A-13I, and 18A-18G.

Figure 11:
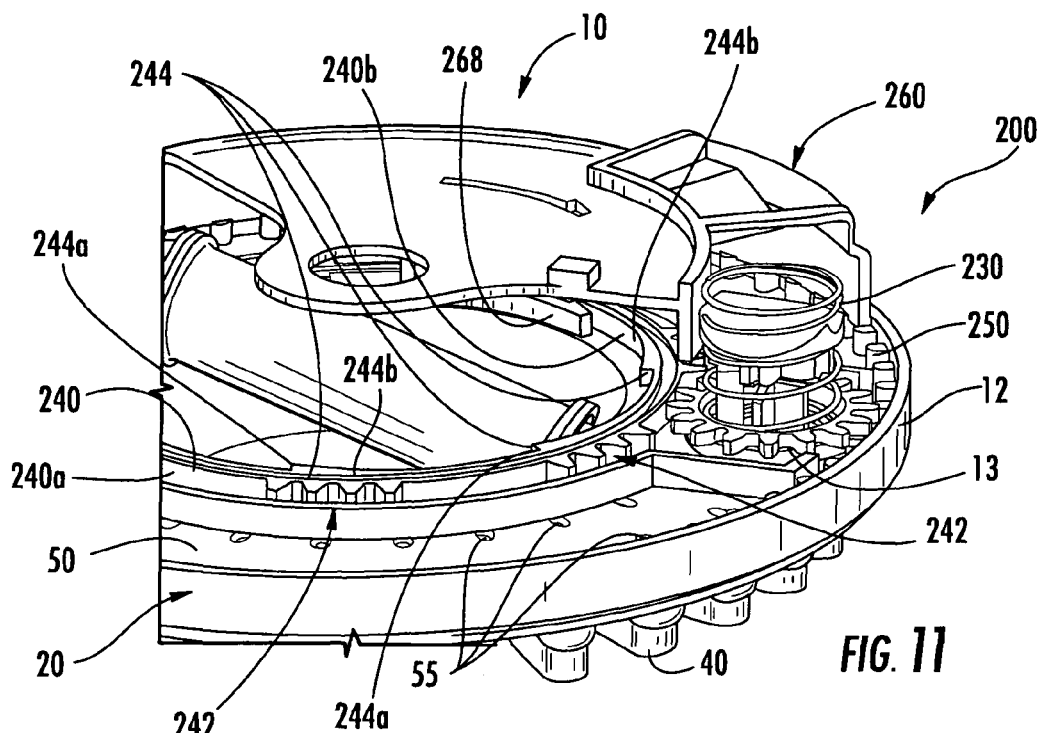
FIG. 11 is a cutaway, partial perspective view of an inhaler having a rotatable piercing mechanism, according to some embodiments of the present invention.

FIG. 11 is a partial cutaway perspective view of a dose container assembly 20 in an inhaler 10 cooperating with a rotating piercing mechanism 200 according to some embodiments of the present invention. As described above, the dose container assembly 20 includes a dose container disk 30, a lower airway disk 40 and an upper airway disk 50. In other embodiments, the dose container assembly 20 can include the dose container disk 30 and only one of the lower airway disk 40 or the upper airway disk 50.

The dose container assembly 20 is rotatably secured within the inhaler housing 12. As described above with respect to FIGS. 3A and 3C, the dose container disk 30, in some embodiments, has opposing upper and lower primary surfaces, a first row of circumferentially spaced apart dose containers 30*c* at a first radius and a second row of circumferentially spaced apart dose containers 30c at a second radius so that the first and second rows are concentric with respect to a center of the disk 30. The dose containers 30c contain dry powder therein and are defined by apertures 30a, which are sealed by sealants 36, 37 over and under the apertures 30a.

The piercing mechanism 200 is operably associated with the dose container assembly 20 and is configured to pierce the first and second sealants 36, 37 that seal a dose container 30c. The piercing mechanism 200 is rotatable such that it can serially alternate between the two rows of dose containers 30c. For example, the piercing mechanism 200 is configured to pierce the sealants 36, 37 over and under a dose container 30c in a first row of dose container apertures 30a, and then rotate and pierce the sealants 36, 37 over and under a dose container 30c in a second row of dose container apertures 30a.

Figure 12A:
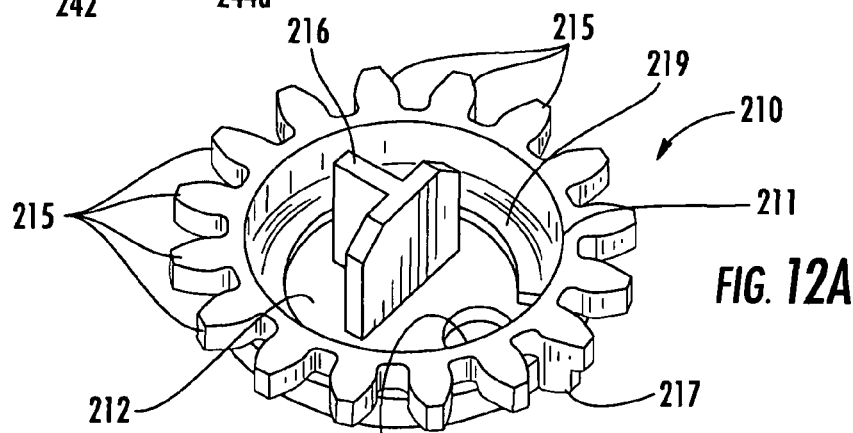
FIG. 12A is a top perspective view of a rotatable drum for the piercing mechanism of FIG. 11.
Figure 12B:
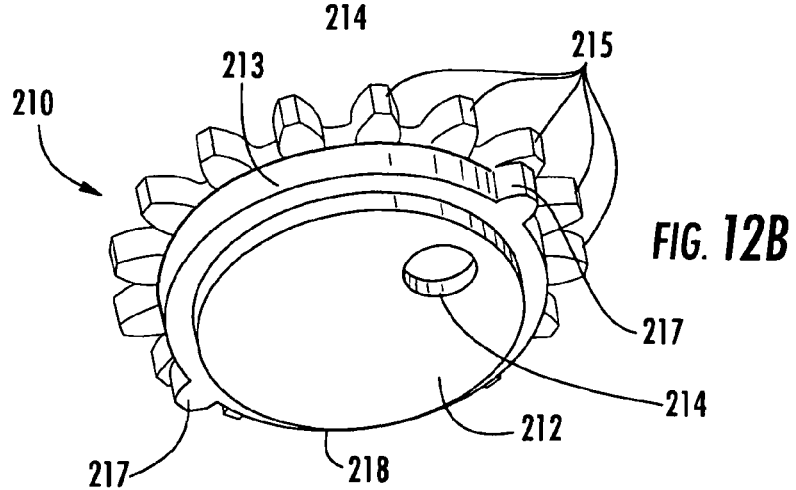
FIG. 12B is a bottom perspective view of the rotatable drum for the piercing mechanism of FIG. 11.

In the illustrated embodiment, the piercing mechanism 200 includes a rotatable drum 210, an elongate piercing member 220, and a biasing member 230. Referring to FIGS. 12A-12B, the rotatable drum 210 has an open end 211, an opposite closed end 212, and a cylindrical wall 213 that extends from the closed end 212 and terminates at the open end 211. The closed end 212 includes an aperture 214 formed therein in a location adjacent to the wall 213, as illustrated. The elongate piercing member 220 (FIG. 13B) is extended and retracted through the aperture 214, as will be described below. Gear teeth 215 extend circumferentially around the wall 213 adjacent the open end 211, as illustrated. A support member 216 extends outwardly from the closed end 212, as illustrated, and is configured to support the piercing member 220. In addition, a pair of diametrically opposed teeth 217 extend outwardly from the wall 213 below the gear teeth 215.

The closed end 212 of the drum 210 has a substantially circular portion 218 that extends outwardly therefrom so as to give the closed end 212a stepped configuration, as illustrated in FIG. 12B. This portion 218 is configured to be inserted within a corresponding substantially circular recessed portion 13 in the inhaler 10 to facilitate rotation of the drum 210.

The elongate piercing member 220 (FIG. 13B) includes a distal piercing portion 221 and a proximal head portion 222. In some embodiments, the distal piercing portion 221 can be a corkscrew piercer configured to pierce the sealants 36, 37 with a straight vertical non-rotational movement, as illustrated and described with respect to FIGS. 14A-14B, below. In some embodiments, the distal piercing portion 221 can have a fluted piercer configured to pierce the sealants 36, 37, as illustrated and described with respect to FIGS. 14C-14E.

The elongate piercing member 220 is movably associated with the support member 216 in the drum 210 so as to be capable of reciprocal movement between piercing and non-piercing positions. In the piercing position, the piercing member distal piercing portion 221 extends through the drum aperture 214 and through the first and second sealants 36, 37 of a dose container 30c (FIGS. 13C, 13D). In a retracted position, the distal piercing portion 221 is retracted above a lower surface of the drum aperture 214, such that the drum 210 is free to rotate.

As shown in FIG. 11, a coil spring 230 serves the function of a biasing member that is configured to urge the piercing member 220 toward the fully retracted position. The illustrated spring 230 is supported at one end within the drum 210 by the closed end 212 and extends upwardly around the support member 216 and is attached to the head portion 222. An arcuate rib 219 extends from the drum closed end 212, as illustrated in FIG. 12A. An end of the coil spring 230 is positioned between the rib 219 and the internal surface of drum wall 213. The rib 219 provides stability to the spring 230 and inhibits the spring 230 from becoming misaligned within the drum 210. An opposite end portion of the spring 230 is attached to the head portion 222 of the piercing member 220 in any of various ways. As such, the spring 230 provides a biasing force to the piercing member 220 so as to urge the piercing member 220 to a retracted position away from the drum closed end 212.

Referring back to FIG. 11, a ring gear 240 is rotatably secured within the inhaler housing 12, and includes multiple sets of teeth 242 that are circumferentially spaced-apart from each other along an outer perimeter 240a, thereof. The illustrated ring gear 240 includes an inner perimeter 240b having a plurality of spaced-apart steps 244. Each step 244 includes an end 244a and a tapered portion 244b extending away from the end 244a. As shown and as will be described further below, each end 244a of a step 244 is configured to be engaged by a pawl 268 associated with an actuator 260 of the inhaler 10. The tapered portion 244b of each step 244 allows the pawl 268 to slide along the step 244 and engage the end 244a.

Still referring to FIG. 11, the piercing mechanism 200 is positioned relative to the ring gear 240 such that the drum gear teeth 215 cooperate with a respective set of teeth 242 on the ring gear outer perimeter. Rotation of the ring gear 240 by a predetermined amount, when a set of teeth 242 are engaged with the drum gear teeth 215, causes the drum 210 to rotate such that the piercing member 220 moves from a position overlying a dose container 30c in one row to a position overlying a dose container 30c in the other row. In the illustrated embodiment, and based upon the illustrated arrangement of dose containers 30c in the disk 30, rotation of the ring gear 240 by a predetermined amount causes the drum 210 to rotate approximately one-hundred eighty degrees (180°).

Still referring to FIG. 11, the dose container assembly 20 includes gear teeth 250 on an outer perimeter thereof. In embodiments where an upper airway disk is not utilized, the gear teeth 250 can extend from an outer or inner perimeter of the dose disk 30. In embodiments where an upper airway disk 50 is utilized, the gear teeth 250 can extend from an outer or inner perimeter of the upper airway disk 50. Embodiments of the present invention are not limited to gear teeth extending from the outer perimeter of the upper airway disk 50. The diametrically opposed teeth 217 that extend outwardly from the drum wall 213 are configured to engage the dose container assembly gear teeth 250. Rotation of the drum 210 via the ring gear 240, in turn, causes rotation of the dose container assembly 20. A set of teeth 217 may be diametrically opposed from each other, according to some embodiments. Embodiments of the present invention are not limited to a single tooth 217, as illustrated.

Figure 1C:
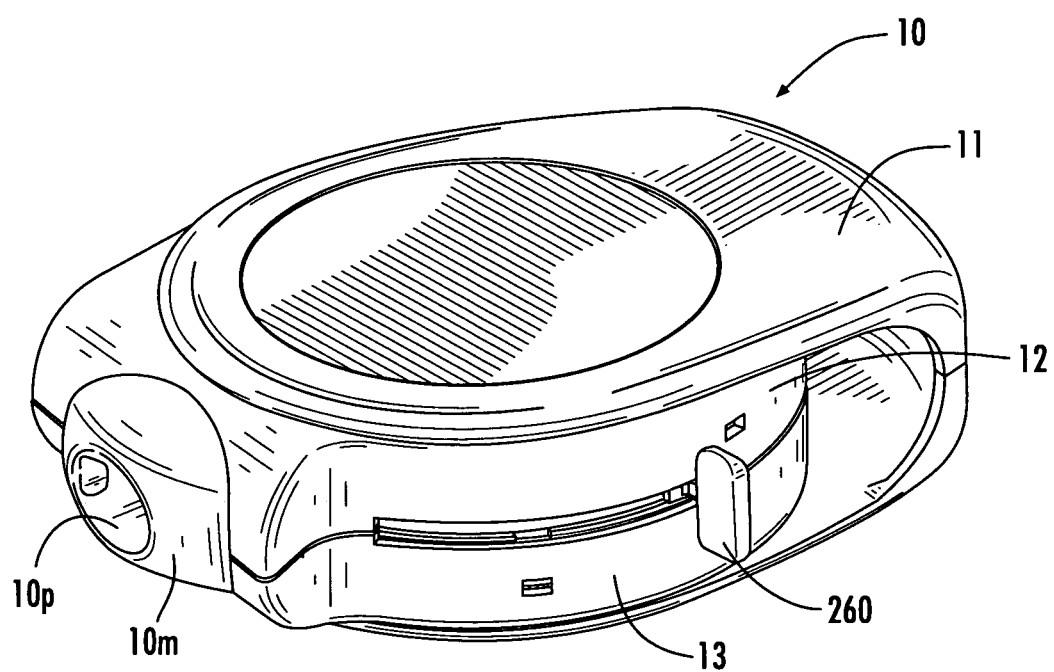
FIG. 1C is a front perspective view of the inhaler of FIG. 1B illustrating the user-accessible actuator lever moved to a second position.

The inhaler 10 includes a user-accessible actuator 260 that is configured to rotate the dose container assembly 20 to place one or more dose containers 30c (FIG. 2B) in a dispensing position in an inhalation chamber in fluid communication with the inhalation port 10p (FIG. 1) and to cause the piercing member 220 to open a dose container 30c in the front row, then the back row (or vice versa) to release medicament to an inhalation air flow path for inhalation by a user. The actuator 260 is movable between first and second positions, as illustrated in FIGS. 13A-13I.

Figure 13A:
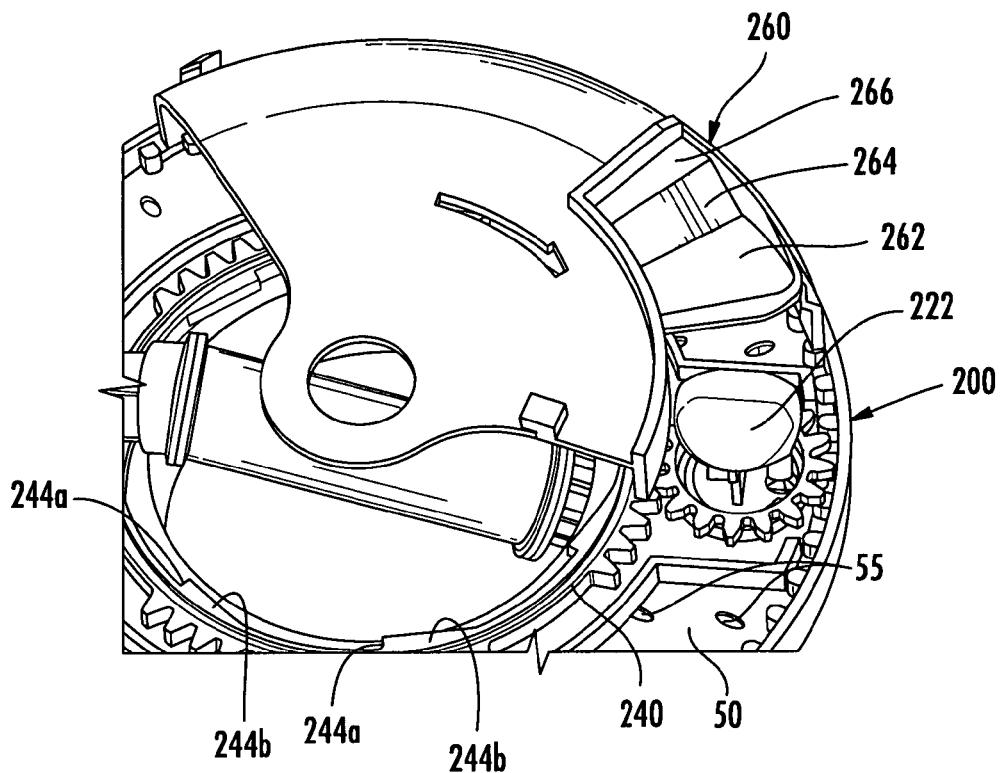
FIGS. 13A-13I are various views of the piercing mechanism of FIG. 11 that illustrate an exemplary sequence of operations for the rotatable piercing mechanism, according to some embodiments of the present invention.
Figure 13B:
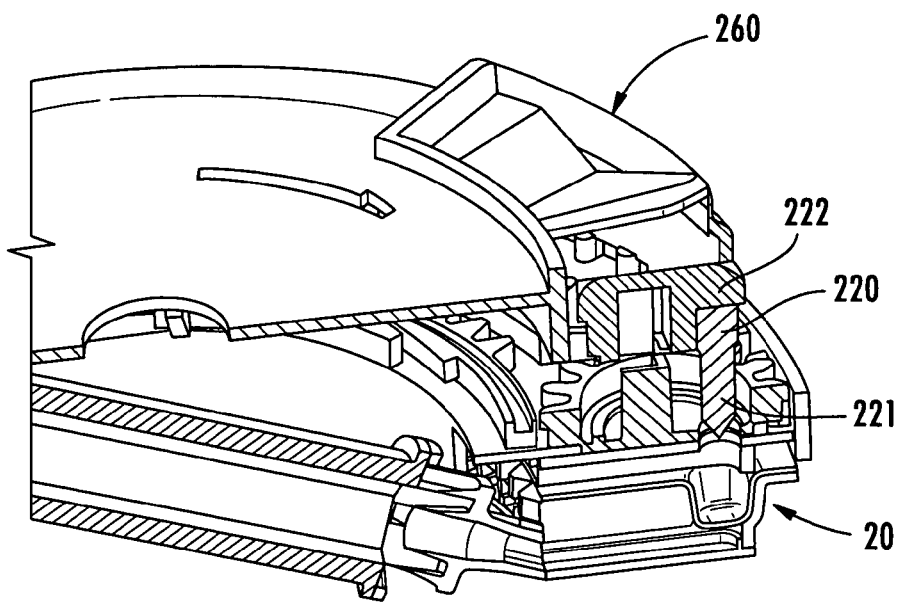
Figure 13C:
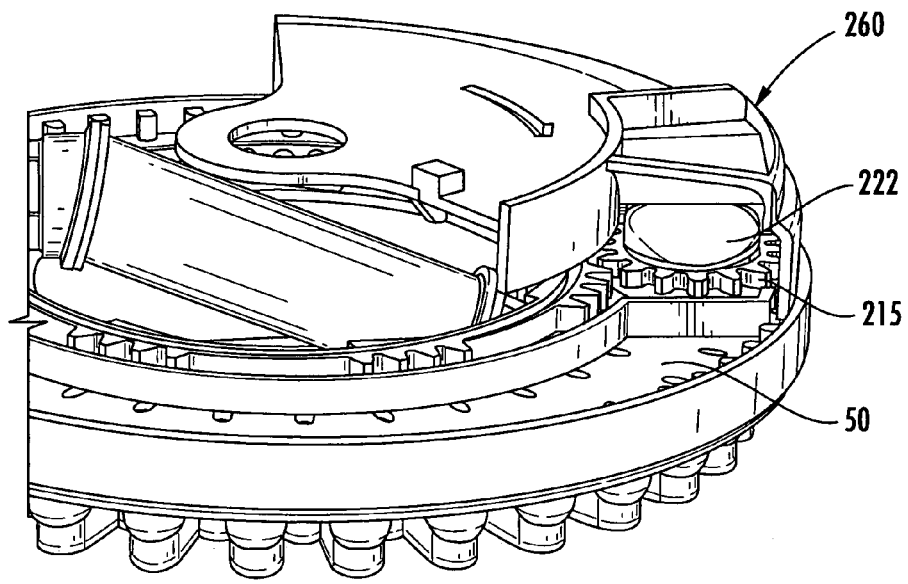
Figure 13D:
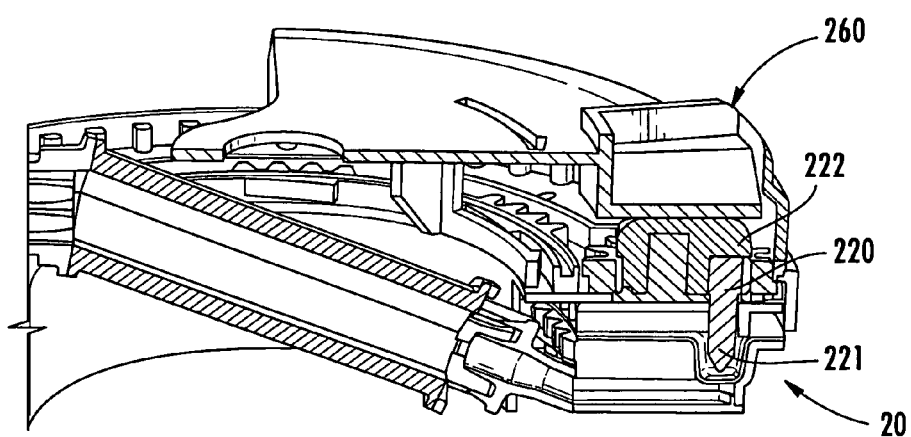

In FIGS. 13A-13B, the actuator 260 is in the first or rest position and the piercing member 220 is positioned over an aperture 55 in the upper airway disk 50 that corresponds with a respective dose container 30c. A user begins to rotate the actuator 260 in a clockwise direction which causes the actuator 260 to engage the piercing member head portion 222. The illustrated actuator 260 includes first and second inclined portions 262, 264 adjacent to each other. The first portion 262 has an inclined configuration (e.g., a ramp) that causes the piercing member 220 to move downwardly to the piercing position as the actuator moves in the clockwise direction. The actuator second portion 264, which is adjacent to the first portion 262, has an inclined configuration opposite that of the first portion 262. In other words, the inclined first and second portions 262, 264 form a V-shape. A third portion 266 adjacent to the second portion 264 has a non-inclined configuration, as illustrated.

The actuator second portion 264 allows the piercing member 220 to move from a piercing position to a partially retracted position. When the actuator is in the second position, the non-inclined third portion 266 is engaged with the head portion 222 of the piercing member 220. As such, the piercing member 220 is in a partially retracted position to inhibit dry powder spillage and overdosing conditions as described above.

Figure 13E:
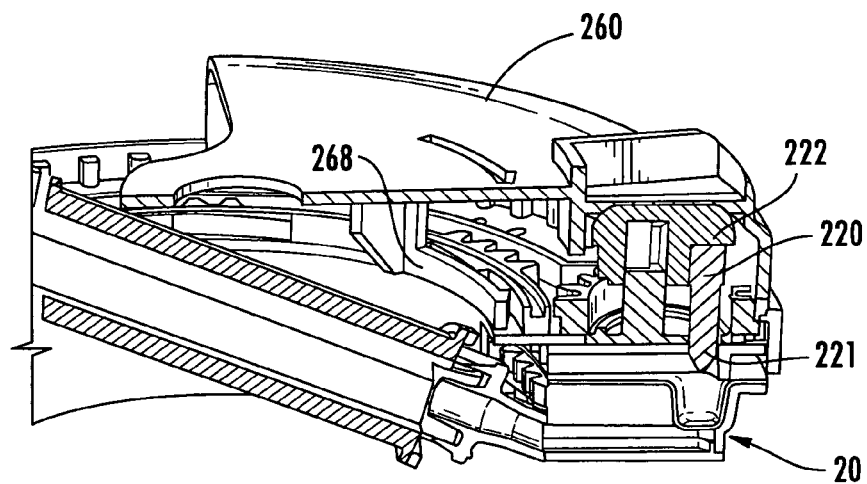

FIGS. 13C-13D illustrate clockwise movement of the actuator 260 such that the actuator first portion 262 pushes the piercing member 220 downward to puncture the first and second sealants 36, 37. In FIG. 13E, the actuator 260 has continued to rotate in the clockwise direction to the second position such that the head portion 222 of the piercing member 220 is engaged by the non-inclined portion 266. In the second position, the piercing member 220 is allowed to partially retract. This allows airflow through the pierced dose container 30c, but blocks the aperture 55 in the airway disk 50, thereby preventing possible powder spillage during inverted operation of the inhaler 10.

Figure 13F:
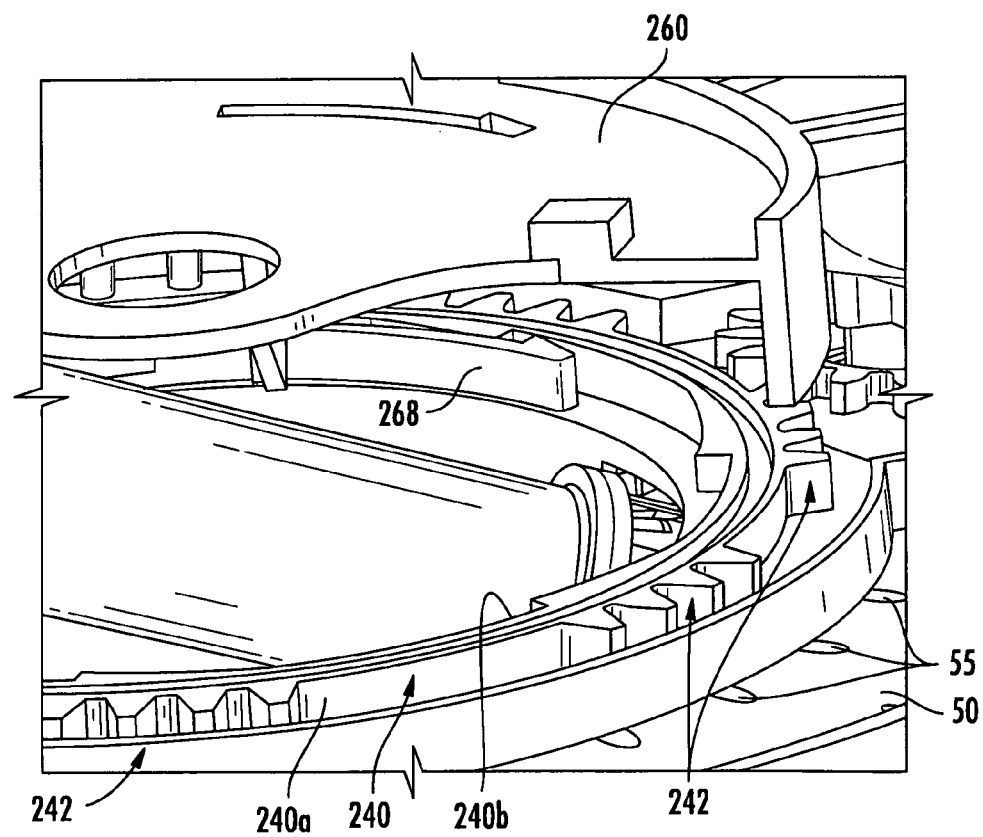

Referring to FIG. 13F, the actuator 260 pawl 268 is about to engage a step 244 on the inner perimeter of the ring gear 240 as the actuator 260 is moved from the second position to the first position. When engaged with the step 244, the pawl 268 causes rotation of the ring gear 240 when the actuator 260 is moved from the second position to the first position. In FIG. 13F, the actuator 260 is in the second position and the pawl 268 has moved along the tapered portion 244b of a step 244 and past the end 244a of the step 244.

Figure 13G:
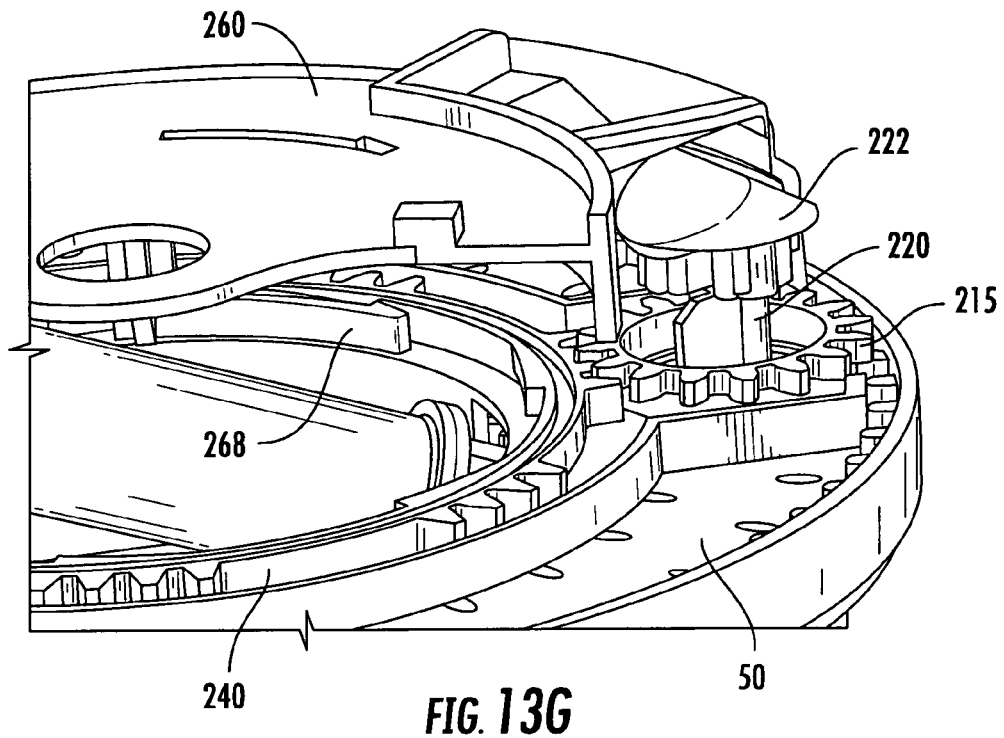
Figure 13H:
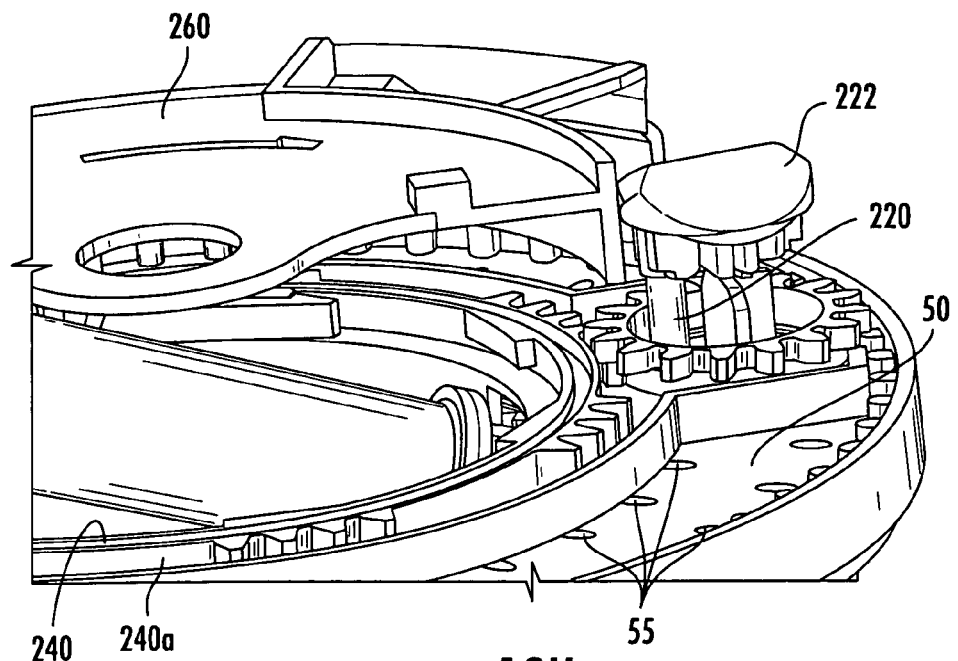

After inhalation of the powder, the user moves the actuator 260 from the second position to the first position (i.e., counterclockwise). Movement of the actuator 260 from the second position to the first position is illustrated in FIGS. 13G-13H. Movement of the actuator 260 to the first position allows the piercing member 220 to partially retract from the dose disk 30 and airway disks 40, 50. The counterclockwise movement of the actuator 260 then causes the actuator pawl 268 to engage the end 244a of a step 244 and to rotate the ring gear 240 in the counterclockwise direction. This counterclockwise rotation of the ring gear 240 cause one of the sets of teeth 242 on the outer perimeter 240a of the ring gear 240 to engage the drum gear teeth 215 and to cause rotation of the drum 210 by a predetermined amount. The amount of rotation of the drum 210 is controlled by the number and configuration of teeth 242 and this number is selected such that the drum 210 is rotated substantially one-hundred eighty degrees (180°) so that the piercing member 220 is positioned above a dose container 30c in the other row of dose containers.

Figure 16:
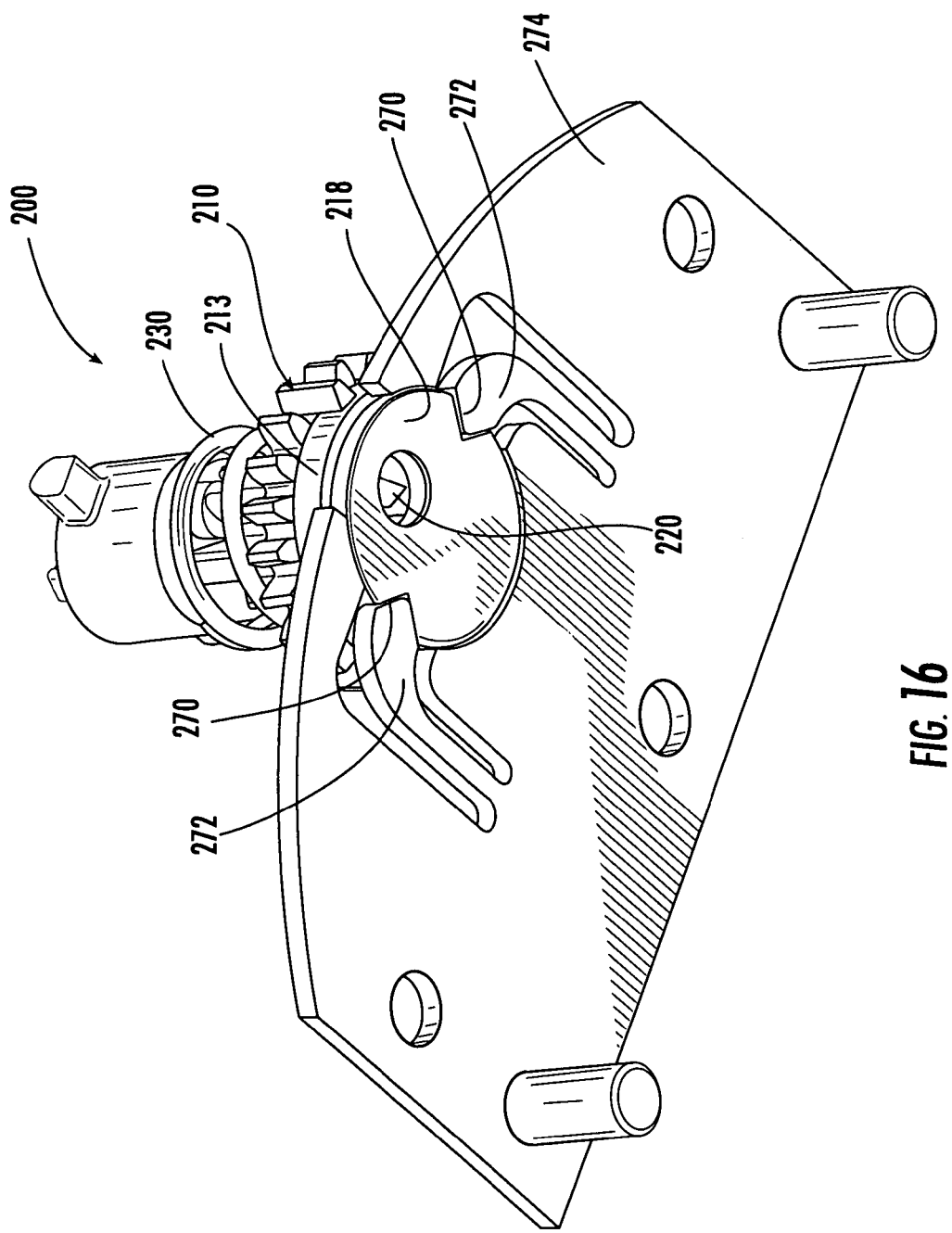
FIG. 16 is a bottom perspective view of the rotatable drum for a piercing mechanism, according to embodiments of the present invention.

In some embodiments, one or more alignment members may be provided to cooperate with the drum 210 to assure exact positioning of the piercing member 220 over an aperture 55 in the upper airway disk 50. For example, as illustrated in FIG. 16, drum portion 218 includes a pair of notches 270. A corresponding pair of spring-loaded pawls 272 associated with frame 274 that rotationally supports the drum 210 are configured to deflect and cooperate with notches 270 when the drum 210 is rotated to a piercing position. These spring-loaded pawls 272 stop rotation of the drum 210 so as to precisely position the piercing member 220. The force exerted by the spring-loaded pawls 272 is sufficient to locate and retain the drum 210 in a correct piercing position, but not so high as to inhibit rotation of the drum under the rotational force imparted by the ring gear 240, as described above. Embodiments of the present invention are not limited to the illustrated number or configuration of spring-loaded pawls 272 and notches 270. A single spring-loaded pawl 272 and notch 270 may be utilized, for example.

Figure 13I:
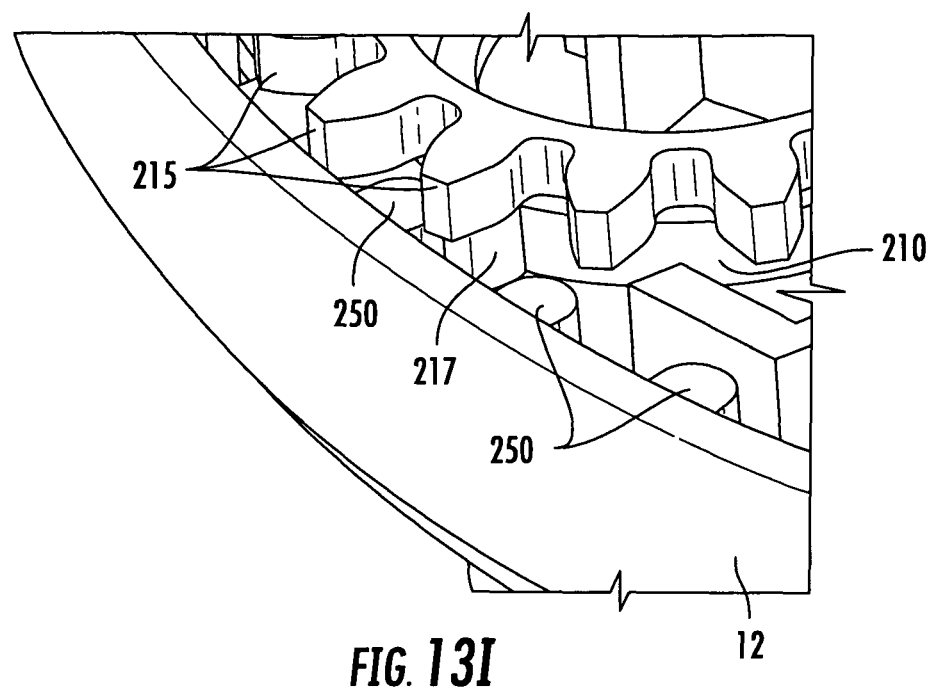

Referring to FIG. 13I, as the drum 210 is rotated by the ring gear 240, one of the diametrically opposed teeth 217 extending from the drum 210 engages a mating tooth 250 on the dose container assembly 20 and rotates the dose container assembly a predetermined amount, e.g., about six degrees (6°), etc. The amount of rotation of the dose container assembly 20 depends on the number and arrangement of dose containers 30c in the dose container disk 30. This amount of rotation can be controlled by the number and arrangement of gear teeth 250 on the dose container assembly and/or by the number and arrangement of teeth 217 extending from the drum 210.

When the actuator 260 is returned to the first position, a fresh dose container 30c is positioned under the piercing member 220, and the inhaler is ready for another cycle.

FIG. 14A illustrates one embodiment of a piercing mechanism 200 with a corkscrew piercer 220. In operation the corkscrew moves up and down vertically straight, typically without rotation, to create a desired opening shape (e.g., circular) through the sealant layers 36, 37. In other embodiments, the corkscrew may rotate during extension and/or dispensing. In the embodiment shown, the corkscrew piercer 220 can remain in the lower channel 41 while the dry powder is dispensed in the airflow path and the blockage of the aperture 30a can be provided by a resilient member 120 that is mounted on the corkscrew 220 and moves up and down therewith. The piercing member 220 can have a two stage operation, fully up (for indexing) and fully down. The most forward portion of the corkscrew can have a point with a configuration that creates a desired cutting configuration into the sealant (e.g., foil). In some embodiments, the corkscrew piercer 220 can cut a shape with a tab into the sealant 36, 37, then fold the tab down to release the dry powder. Positioning the corkscrew piercer 220 in the channel 41 during dispensing may provide improved aerodynamics or shear or impaction flow turbulence for the dry powder. The resilient member 120 can comprise a foam block or other resilient member 120 (such as a hard or rigid member biased by a spring) that can be used to seal or plug the aperture 30a. FIG. 14B illustrates a similar corkscrew piercer 220 that is used with a disk assembly 20 having both upper and lower airway disks 50, 40. A resilient and/or flexible member 200p such as a polymeric and/or elastomeric or foam plug can be used to occlude or seal the disk aperture 55.

FIGS. 14C and 14D illustrate a piercing mechanism 200 with a fluted solid piercer 220. The flute may have a straight flute configuration or the flute can have a twist or partial twist along it length, e.g., the maxima and minima of the lobes change axially along the length of the flute. The flute can have a cross section with a plurality of lobes, typically three or four lobes, shown as three lobes in FIG. 14C. The fluted configuration may extend only a partial forward length and merge into a constant diameter segment that resides in and helps occlude or seal the aperture 55 as shown in FIG. 14E. In other embodiments, the solid or fluted piercer configuration can merge into a cap or plug 200p that resides over and/or in the aperture 55 (see, e.g., FIG. 146). In some embodiments, the twisted flute 220 can remain in the lower disk 40 during dispensing which may facilitate turbulence and/or compaction in the airway.

FIG. 14D illustrates that the fluted piercer 220 can rotate as it pierces the foil or other sealant material to form a round hole or may be extended straight without rotation. In other embodiments, the fluted piercer 220 can be extended or advanced without rotation to pierce the sealant layer(s) 36, 37. FIG. 14E illustrates that the fluted piercer 220' can include a fluted forward portion 220f with a length "$L_1$" that merges into a solid portion 112 that can have a substantially circular cross-section with a length "$L_2$". $L_1$ is typically longer than $L_2$. $L_1$ can have a length sufficient to allow the forward fluted portion 220f to reside in the dose container aperture 30a (typically just below the lower sealant line or in-line with or slightly above or below the lower surface of the disk 30) and/or through the lower sealant 37 at the same time, with the solid portion engaging the airway disk aperture 55.

FIG. 14F illustrates a piercing mechanism 200 that can include a plug 200p (similar to that shown in FIG. 14B for the corkscrew configuration) that can occlude the passage 55. The plug 200p can be used with any piercer, including the corkscrew 220 (FIG. 14A) or the solid fluted piercer 220 (FIG. 14C) or other piercer configuration. The piercing head can remain in the lower channel 41 during dispensing as shown in FIG. 14E, or the piercer may retract partially through a passage in the plug (not shown) while leaving the plug 200p in position against and/or over the aperture or passage 55.

The inhaler 10 can have a body that is a portable, relatively compact "pocket-sized" configuration. In some embodiments, the inhaler body can have a width/length that is less than about 115 mm (about 4.5 inches), typically less than about 89 mm (about 3.5 inches), and a thickness/depth of less than about 51 mm (about 2 inches), typically less than about 38 mm (about 1.5 inches). The inhaler body can also be configured to be generally planar on opposing primary surfaces to facilitate pocket storage.

The inhaler can include a circuit that can control certain operations of the inhaler 10. The inhaler 10 can include a computer port (not shown). The port may be, for example, an RS 232 port, an infrared data association (IrDA) or universal serial bus (USB), which may be used to download or upload selected data from/to the inhaler to a computer application or remote computer, such as a clinician or other site. The inhaler 10 can be configured to via a wired or wireless communication link (one-way or two-way) to be able to communicate with a clinician or pharmacy for reorders of medicines and/or patient compliance. The inhaler 10 may also include a second peripheral device communication port (not shown). The inhaler 10 may be able to communicate via the Internet, telephone, cell phone or other electronic communication protocol.

In some embodiments, the circuit can include computer program code and/or computer applications that communicate additional data to a user (optionally to the display) as noted above and/or communicate with another remote device (the term "remote" including communicating with devices that are local but typically not connected during normal inhalant use).

In some embodiments, the circuit can be in communication with a vibrator device (not shown). The vibrator device can be any suitable vibrator mechanism. The vibrator device can be configured to vibrate the dry powder in the airflow path. In some embodiments, the vibrator device can comprise a transducer that is configured to vibrate the opened cartridge(s) holding the dry powder. Examples of vibrator devices include, but are not limited to, one or more of: (a) ultrasound or other acoustic or sound-based sources (above, below or at audible wavelengths) that can be used to instantaneously apply non-linear pressure signals onto the dry powder; (b) electrical or mechanical vibration of the walls (sidewalls, ceiling and/or floor) of the inhalation flow channel, which can include magnetically induced vibrations and/or deflections (which can use electromagnets or permanent field magnets); (c) solenoids, piezoelectrically active portions and the like; and (d) oscillating or pulsed gas (airstreams), which can introduce changes in one or more of volume flow, linear velocity, and/or pressure. Examples of mechanical and/or electro-mechanical vibratory devices are described in U.S. Pat. Nos. 5,727,607, 5,909,829 and 5,947,169, the contents of which are incorporated by reference as if recited in full herein. Combinations of different vibrating mechanisms can also be used.

In some embodiments, the vibrator device can include a commercially available miniature transducer from Star Micronics (Shizuoka, Japan), having part number QMB-105PX. The transducer can have resonant frequencies in the range of between about 400-600 Hz.

In certain embodiments, the inhaler 10 can include visible indicia (flashing light or display "error" or alert) and/or can be configured to provide audible alerts to warn a user that a dose was properly (and/or improperly) inhaled or released from the inhaler. For example, certain dry powder dose sizes are formulated so that it can be difficult for a user to know whether they have inhaled the medicament (typically the dose is aerosolized and enters the body with little or no taste and/or tactile feel for confirmation). Thus, a sensor (not shown) can be positioned in communication with the flow path in an inhaler and configured to be in communication with a digital signal processor or microcontroller, each held in or on the inhaler. In operation, the sensor can be configured to detect a selected parameter, such as a difference in weight, a density in the exiting aerosol formulation, and the like, to confirm that the dose was released.

The sealed dose containers 30c can be configured so that the water vapor transmission rate can be less than about 1.0 g/100 in$^2$/24 hours, typically less than about 0.6 g/100 in$^2$/24 hours and an oxygen transmission rate that is suitable for the dry powder held therein. The dose container assemblies 20, 20' can be configured with a stable shelf life of between about 1-5 years, typically about 4 years.

The dose containers 30c can have a volume (prior to filling and sealing) that is less than about 24 mm$^3$, typically between 5-15 mm$^3$. The powder bulk density can be about 1 g/cm$^3$ while the power nominal density when filled (for reference) can be about 0.5 g/cm$^3$. The maximum compression of a drug by filling and sealing in the dose container 30c can be less than about 5%, typically less than about 2%. The maximum heating of drug during the filling and sealing can be maintained to a desirable level so as not to affect the efficacy of the drug or the formulation.

Figure 17:
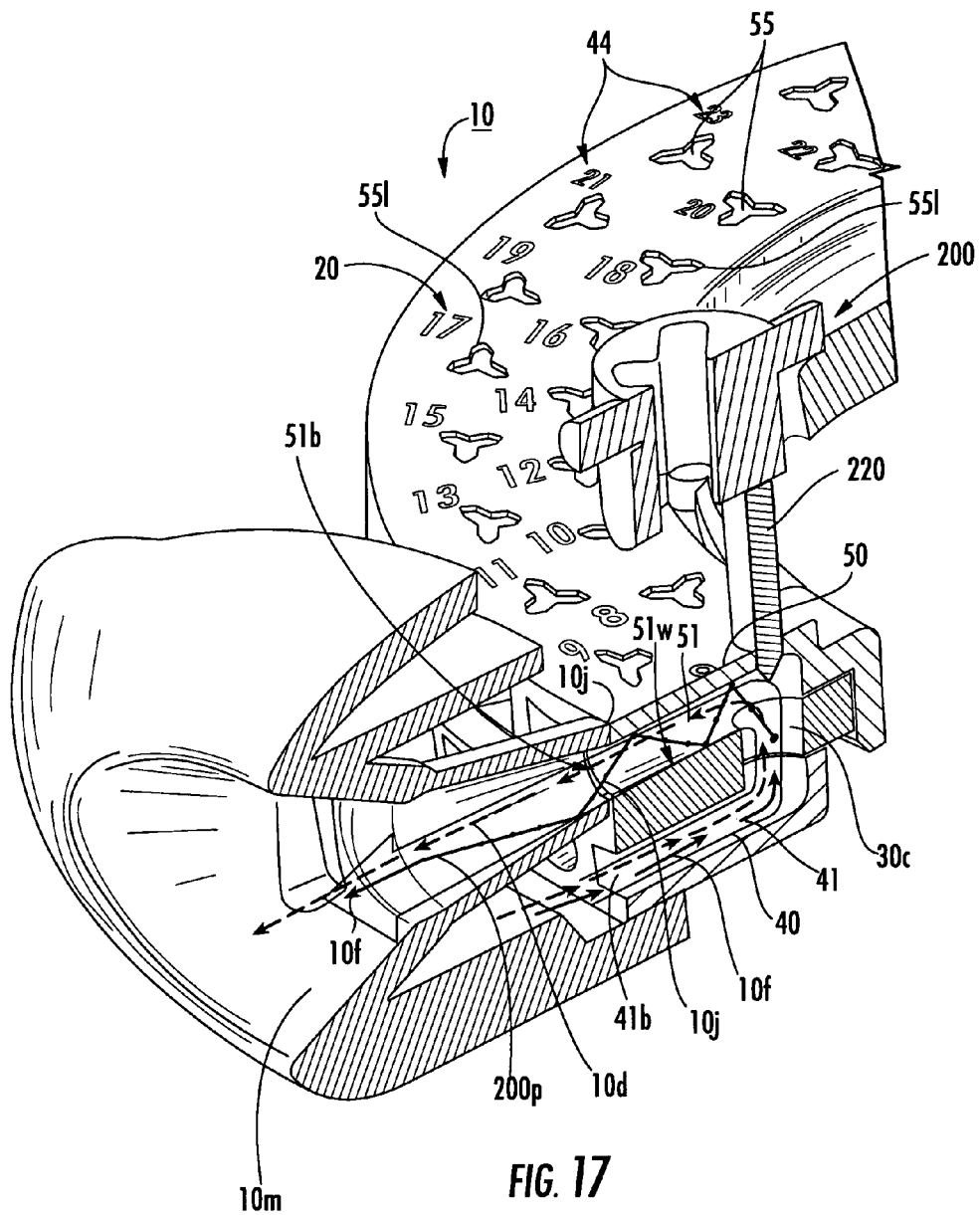
FIG. 17 is an enlarged partial section view of an inhaler having generally "U" shaped inhalation flow paths for each dose according to embodiments of the present invention.

FIG. 17 illustrates the substantially U-shaped airpaths created by the disk assembly 20 (e.g., the upper disk channel 51 and lower disk channel 41 define the long sides of the "U" which extend in a radial direction across the disk body. As shown, in this embodiment, the outer perimeter of the disk assembly 20 holds both the outlet and an inlet for the airflow path 10f. The "U" shaped flow path (or, in some embodiment, a partial "U" where only a one of the airflow disks 40, 50 is used) can function as a powder deagglomerator. The dry powder particles 10d impact the opposing wall of the airway disk channel 51 as they exit the dose container 30c with sufficient force to deagglomerate the drug powder.

FIG. 17 also illustrates an example of dry powder particle trajectories 10d entrained in air flow associated with the inspiratory airflow path 10f. After the dry powder exits the dose container 30c in the airflow path 10f, the air flow and smaller powder particles (10f) in the air are able to make the about 90 degree turn while heavier dry powder particles (10d) bounce off the inner wall 51w of the upper airway disk channel 51 with increasingly shallow angles eventually going more or less straight out of the mouthpiece 10m. The impact of the heavier dry powder against the walls 51w help deagglomerate the dry powder. Referring again to FIG. 5A, in the dual row dose container 30 embodiment, the channels 51 vary in length depending on if the dose container 30 is on the inner or outer row.

In some particular embodiments, the airway channels 41, 51 can include alternating short and long channels (see, e.g., FIG. 5A). The length of the long channel (the channels with the dose container on the inner perimeter where the outer perimeter is the exit location and vice versa if the inner perimeter is the exit location) can between about 5 mm to about 15 mm, typically about 10 mm, the length of the short channel can be between about 3-10 mm, typically about 5 mm (e.g., about 40-70% the length of the long channel. The depth (vertical height) of each channel 41, 51 can be the same or can, in some embodiments vary. Exemplary depths of the channels 41, 51 are between about 1 mm to about 3 mm, typically about 2 mm, but other depths can be used.

Figure 15:
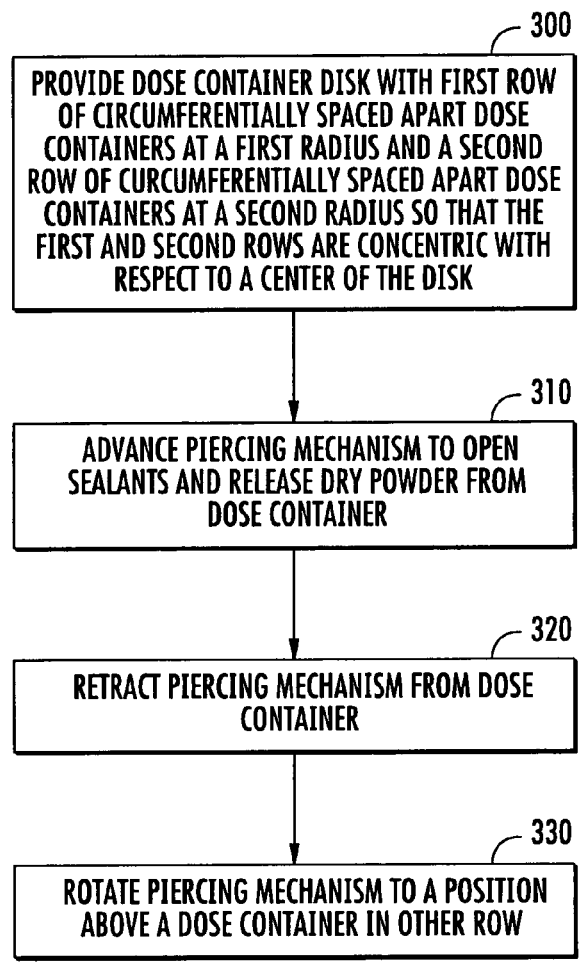
FIG. 15 is a flow chart of exemplary operations that can be used to operate an inhaler according to some embodiments of the present invention.

Referring to FIG. 15, exemplary operations that can be used to operate an inhaler according to some embodiments of the present invention are illustrated. A dose container disk having opposing upper and lower primary surfaces, a first row of circumferentially spaced apart dose containers at a first radius and a second row of circumferentially spaced apart dose containers at a second radius so that the first and second rows are concentric with respect to a center of the disk, are provided (Block 300). The dose containers have dry powder therein, and each dose container terminates at a respective aperture in the upper surface and at a respective aperture in the lower surface. A first flexible sealant resides over the apertures in the upper surface, and a second flexible sealant resides over the apertures in the lower surface. A piercing mechanism is advanced to open both sealants and release dry powder from a dose container (Block 310). The piercing mechanism is retracted from the dose container (Block 320), and rotated to a position above a dose container in the other row (Block 330).

FIGS. 18A-18G are cutaway, top perspective views of a dose container assembly 20 in an inhaler 10 cooperating with a rotating piercing mechanism 200 according to other embodiments of the present invention. The dose container assembly 20 includes a dose container disk 30, a lower airway disk 40 and an upper airway disk 50 as described above and illustrated in FIGS. 2A-2B. However, embodiments of the present invention are not limited to this dose container assembly configuration. For example, in other embodiments, the dose container assembly 20 can include the dose container disk 30 and only one of the lower airway disk 40 or the upper airway disk 50.

The illustrated dose container assembly 20 is rotatably secured within the inhaler housing 12. As described above with respect to FIGS. 3A and 3C, the dose container disk 30, in some embodiments, has opposing upper and lower primary surfaces, a first row of circumferentially spaced apart dose containers 30c at a first radius and a second row of circumferentially spaced apart dose containers 30c at a second radius so that the first and second rows are concentric with respect to a center of the disk 30. The dose containers 30c contain dry powder therein and are defined by apertures 30a, which are sealed by sealants 36, 37 over and under the apertures 30a.

Figure 3D:
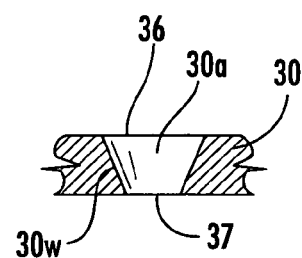
FIG. 3D is a partial cutaway view of a single dose container according to some embodiments of the present invention.

The piercing mechanism 200 is operably associated with the dose container assembly 20 and is configured to pierce the first and second sealants 36, 37 that seal a dose container 30c (see FIGS. 3C-3D). The piercing mechanism 200 is rotatable such that it can serially alternate between the two rows of dose containers 30c. For example, the piercing mechanism 200 is configured to pierce the sealants 36, 37 over and under a dose container 30c in a first row of dose container apertures 30a, and then rotate and pierce the sealants 36, 37 over and under a dose container 30c in a second row of dose container apertures 30a.

Figure 18A:
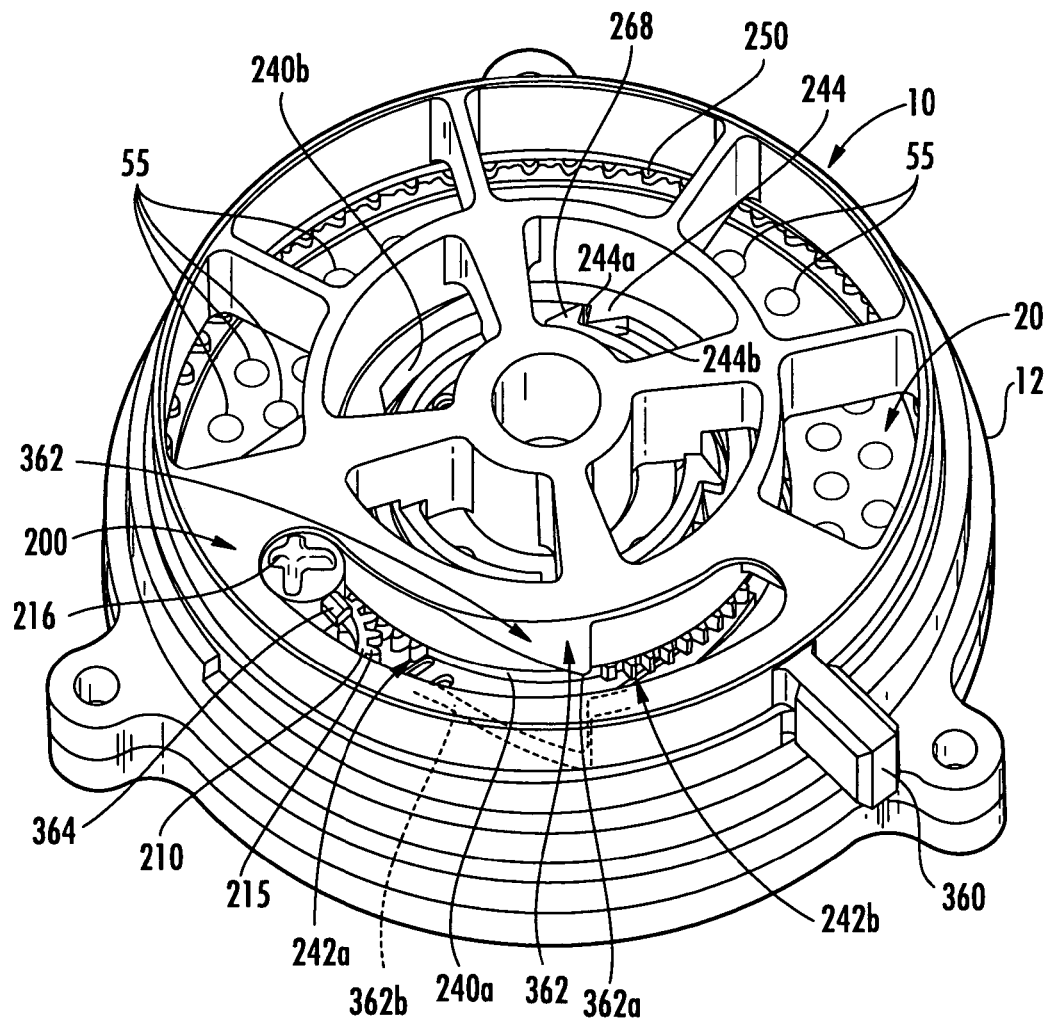
FIGS. 18A-18G are cutaway, top perspective views of an inhaler having a rotatable piercing mechanism and illustrate an exemplary sequence of operations for a rotatable piercing mechanism, according to some embodiments of the present invention.
Figure 18B:
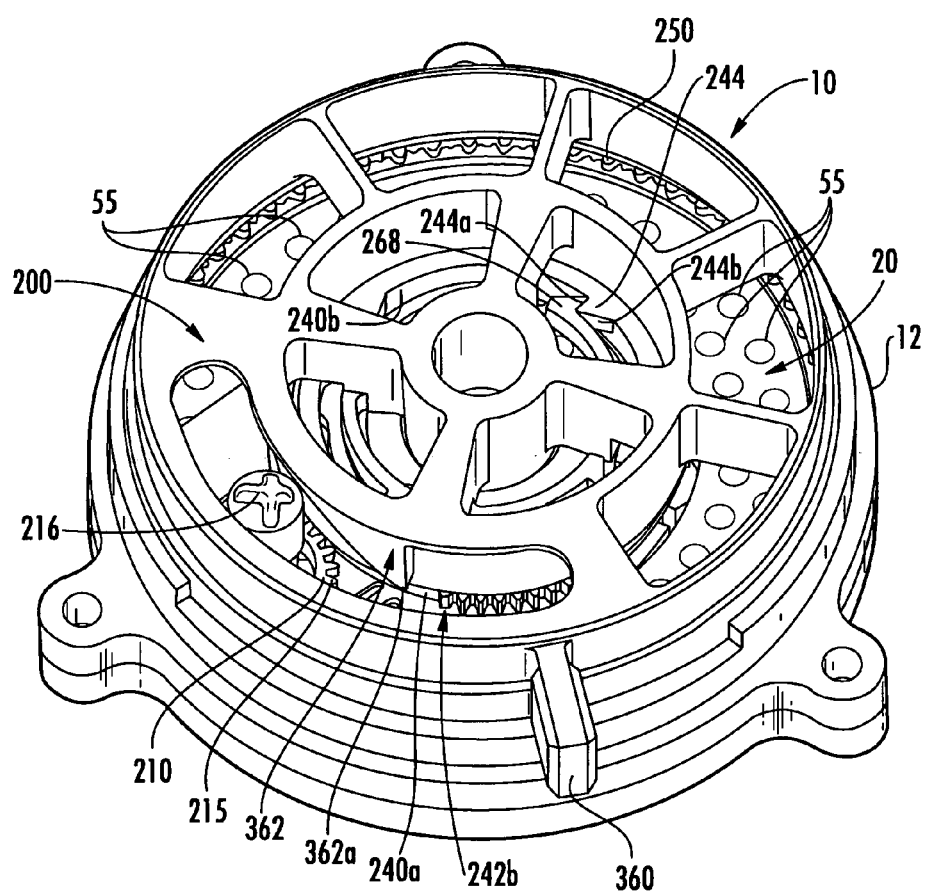
Figure 18C:
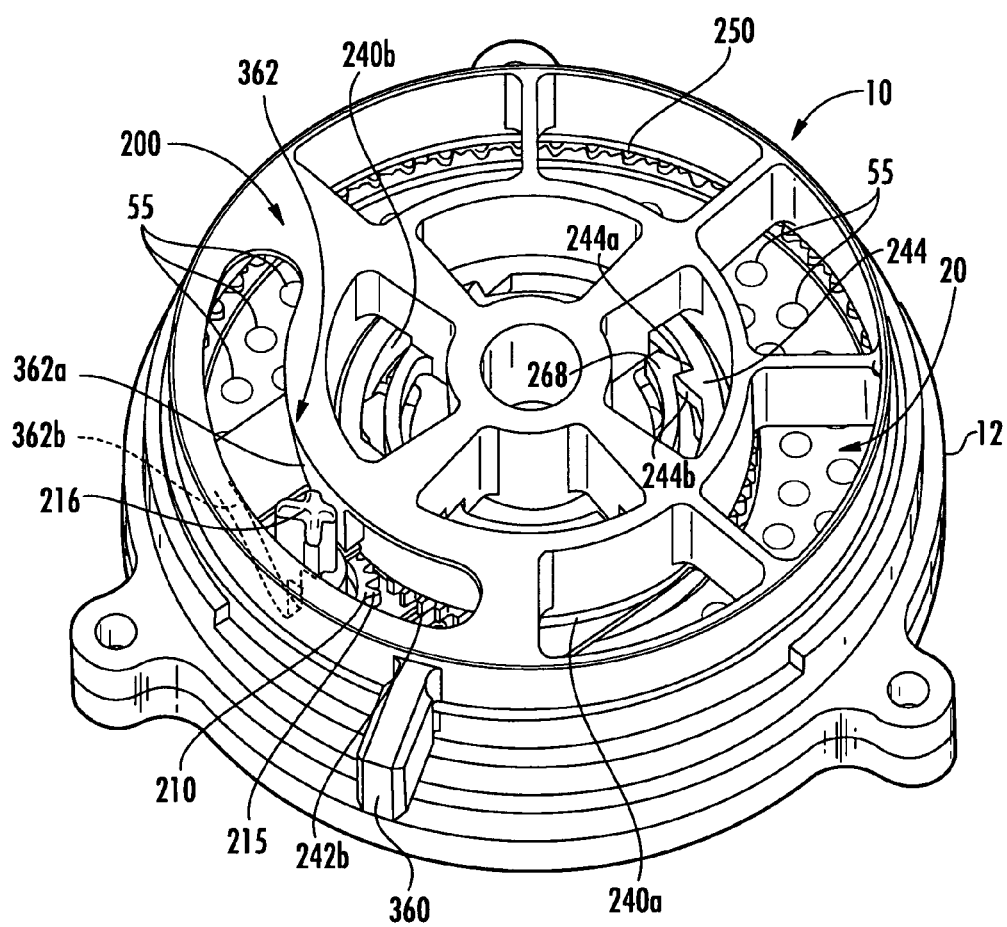
Figure 18D:
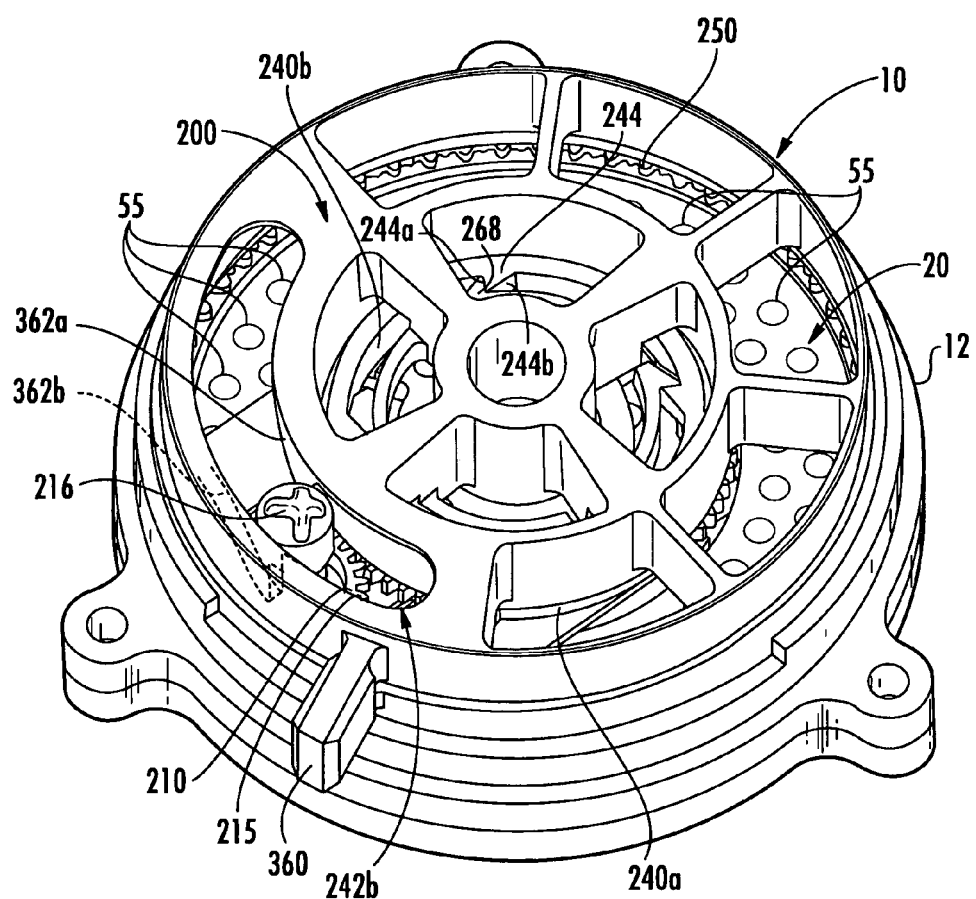
Figure 18E:
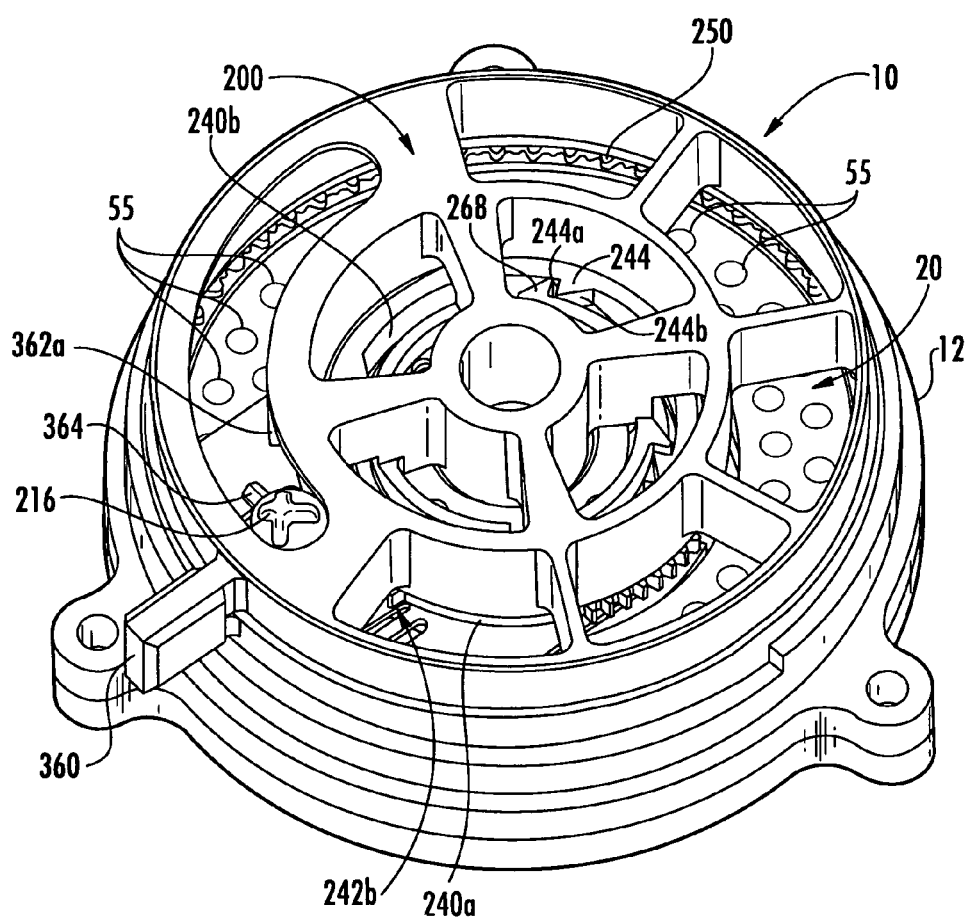
Figure 18F:
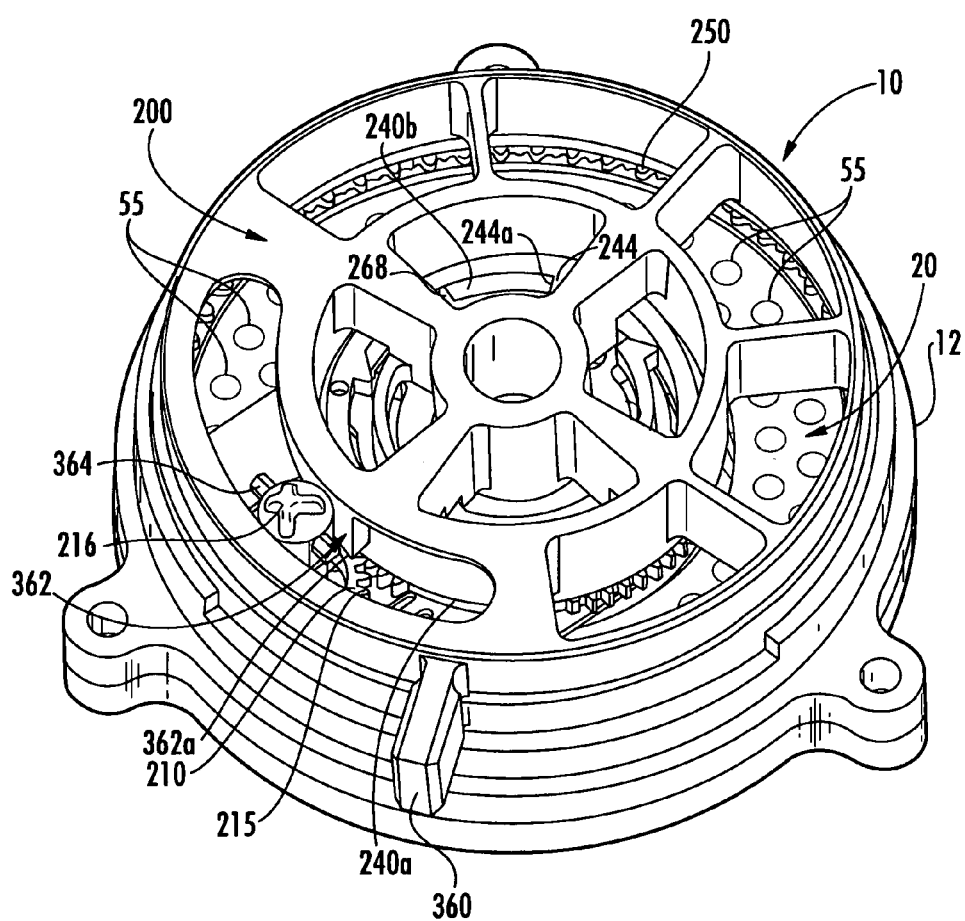
Figure 18G:
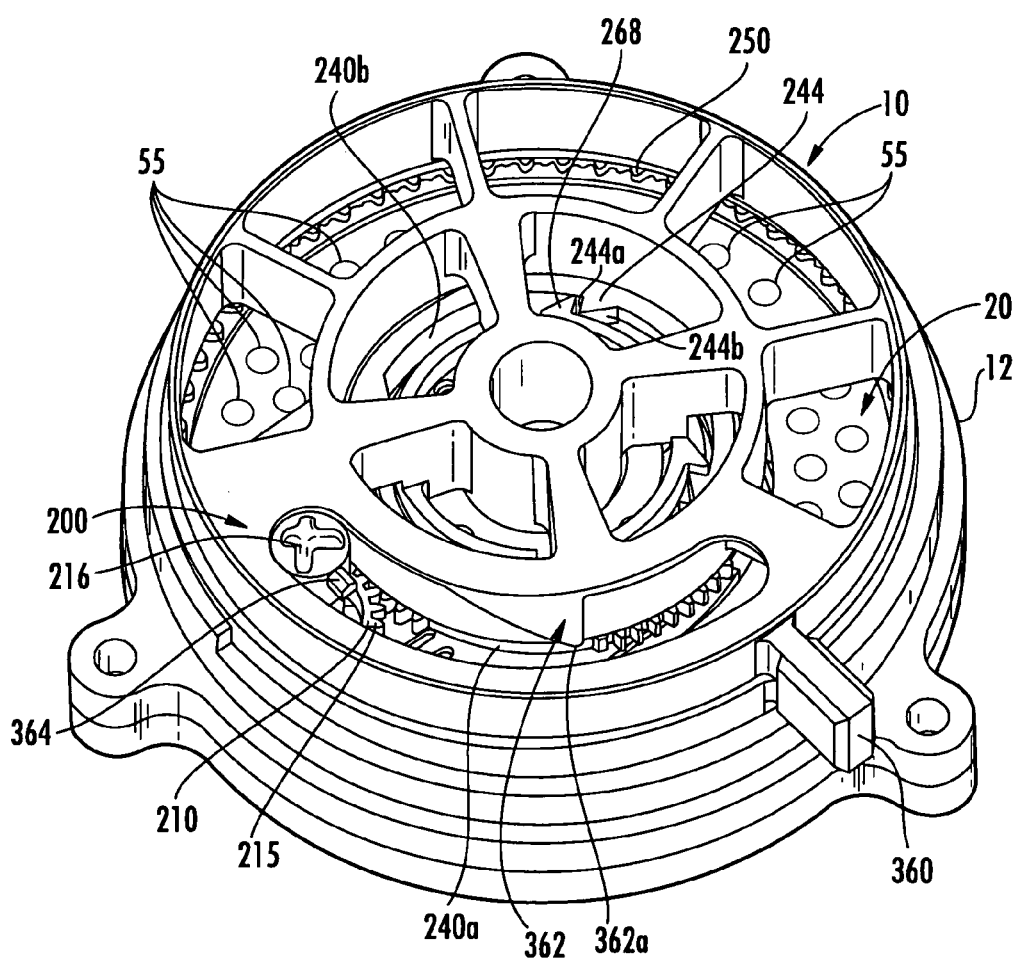

As described above, the piercing mechanism 200 includes a rotatable drum 210, an elongate piercing member 220, and a biasing member 230. Also, as described above with respect to FIGS. 12A-12B, the rotatable drum 210 has an open end 211, an opposite closed end 212, and a cylindrical wall 213 that extends from the closed end 212 and terminates at the open end 211. The closed end 212 includes an aperture 214 formed therein in a location adjacent to the wall 213, as illustrated. The elongate piercing member 220 is extended and retracted through the aperture 214, as will be described below. Gear teeth 215 extend circumferentially around the drum wall 213 adjacent the open end 211, as illustrated. A support member 216 extends outwardly from the closed end 212, as illustrated, and is configured to support the piercing member 220. In addition, a pair of diametrically opposed teeth 217 extend outwardly from the wall 213 below the gear teeth 215.

The elongate piercing member 220 has a configuration as described above. Moreover, in some embodiments, the distal piercing portion can be a corkscrew piercer configured to pierce the sealants 36, 37 with a straight vertical non-rotational movement, as illustrated and described with respect to FIGS. 14A-14B, below. In some embodiments, the distal piercing portion can have a fluted piercer configured to pierce the sealants 36, 37, as illustrated and described with respect to FIGS. 14C-14D.

The elongate piercing member 220 is movably associated with the support member 216 in the drum 210 so as to be capable of reciprocal movement between piercing and non-piercing positions. In the piercing position, the piercing member distal piercing portion 221 extends through the drum aperture 214 and through the first and second sealants 36, 37 of a dose container 30*c* (FIGS. 13C, 13D). In a retracted position, the distal piercing portion 221 is retracted above a lower surface of the drum aperture 214, such that the drum 210 is free to rotate. As described above, a coil spring 230 (FIG. 11) serves the function of a biasing member that is configured to urge the piercing member 220 toward the fully retracted position.

FIGS. 18A-18G illustrate an alternative embodiment to the rotating piercing mechanism 200, discussed above. As shown, a ring gear 240 is rotatably secured within the inhaler housing 12, and includes multiple sets of teeth 242*a*, 242*b*, etc., that are circumferentially spaced-apart from each other along an outer perimeter 240*a*, thereof. The illustrated ring gear 240 includes an inner perimeter 240*b* having a plurality of spaced-apart steps 244. Each step 244 includes an end 244*a* and a tapered portion 244*b* extending away from the end 244*a*. As described above, each end 244*a* of a step 244 is configured to be engaged by a pawl 268 associated with the actuator 360 of the inhaler 10. The tapered portion 244*b* of each step 244 allows the pawl 268 to slide along the step 244 and engage the end 244*a*.

The illustrated actuator 360 includes a ramp 362 having a pair of spaced-apart first and second inclined portions 362*a*, 362*b*. The piercing member 220 also includes a pair of opposing arms 364 extending outwardly therefrom, as illustrated in FIG. 18F. These arms 364 are configured to engage the respective inclined portions 362*a*, 362*b* of the ramp 362, as will be described below.

The actuator 360 is movable by a user of the inhaler 10 between first (FIG. 18A) and second (FIG. 18E) positions. Movement of the actuator 360 from the first position to the second position causes rotation of the ring gear 240 by a predetermined amount. As is shown, this predetermined amount includes four stages of rotation. During a first stage of rotation of the ring gear 240 via the actuator 360, a first set of ring gear teeth 242*a* cooperates with the drum gear teeth 215 and rotates the drum 210 such that the piercing member 220 overlies a dose container 30*c*. This first stage of rotation is illustrated in FIGS. 18A-18B. In the illustrated embodiment, the drum 210 is rotated counterclockwise by ninety degrees (90°) during the first stage of rotation of the ring gear 240. As illustrated in FIG. 18A, at the beginning of the first stage of rotation, the arms 364 are oriented such that they do not engage any portion of the actuator 360. The rotation of the ring gear 240 during the first stage causes rotation of the drum 210 and piercing mechanism 200 such that the arms 364 are in position to engage the ramp 362 (FIG. 18B).

During the second stage of rotation of the ring gear 240, the arms 364 engage the respective inclined portions 362*a*, 362*b* of the ramp 362. Continued rotation of the ring gear 240 via the actuator 360 causes the inclined portions 362*a*, 362*b* to urge the arms 364 downward, thereby causing the piercing member 220 to move downwardly to the piercing position (FIG. 18C).

During the third stage of rotation, the piercing member 220 is moved to the retracted position. This is illustrated in FIG. 18D. As illustrated, continued clockwise rotation of the ring gear 240 via the actuator 360 causes the arms 364 to disengage from the respective inclined portions 362*a*, 362*b* of the ramp 362. The spring 230 (FIG. 11) then urges the piercing member 220 toward the fully retracted position.

During the fourth stage of rotation of the ring gear 240, a second set of ring gear teeth 242*b* cooperates with the drum gear teeth 215. Continued rotation of the ring gear 240 via the actuator 360 causes the drum 210 to rotate such that the piercing member 220 does not overlie a dose container 30*c*. At the end of the fourth stage of rotation of the ring gear 240, the actuator 360 is in the second position (FIG. 18E). In the illustrated embodiment, the drum 210 is rotated counterclockwise by ninety degrees (90°) during the fourth stage of rotation of the ring gear 240. At the end of the fourth stage of rotation, the piercing member 220 is oriented such that the arms 364 do not engage any portion of the actuator 360. At this point, a dose is ready for inhalation by a user and the closed end 212 of the drum 210 blocks the aperture 55.

After inhalation of the powder, the user moves the actuator 360 from the second position (FIG. 18E) back to the first position (FIG. 18G) (i.e., counterclockwise). The inhaler 10 is now ready for another cycle.

FIGS. 19A-19B, 20, 21A-21B, 22, 23A-23B, 24A-24B, 25, and 26A-26B illustrate an alternative embodiment to the rotating piercing mechanism 200, discussed above. As shown, a ring gear 240 is rotatably secured within the inhaler housing 12, and includes multiple sets of teeth 242*a*, 242*b*, etc., that are circumferentially spaced-apart from each other along an outer perimeter 240*a*, thereof. The illustrated ring gear 240 includes an inner perimeter 240*b* having a plurality of spaced-apart steps 244. Each step 244 includes an end 244*a* and a tapered portion 244*b* extending away from the end 244*a*. As described above, each end 244*a* of a step 244 is configured to be engaged by a pawl 268 associated with the actuator 360 of the inhaler 10. The tapered portion 244*b* of each step 244 allows the pawl 268 to slide along the step 244 and engage the end 244*a*.

The illustrated actuator 360 includes a pair of spaced-apart first and second ramps 362*a*, 362*b* that extend outwardly from surface 361. The piercing member 220 also includes a pair of opposing arms 364 extending outwardly therefrom, as illustrated. These arms 364 are configured to engage the respective ramps 362*a*, 362*b*, as will be described below.

Each ramp 362*a*, 362*b* includes a first leg 370 that is attached to the actuator surface 361 and a second leg 372 that has a free end 372*a*. The free end 372*a* of each second leg 372 is in contacting relationship with the actuator surface 361 or is closely located relative to the actuator surface 361 so as to make contact with the actuator surface 361 during a certain stage of actuator operation, as described below. In addition, each ramp second leg 372 is configured to deflect such that the free end 372*a* is temporarily biased away from the actuator surface 361 during a certain stage of actuator operation, as described below.

Figure 19A:
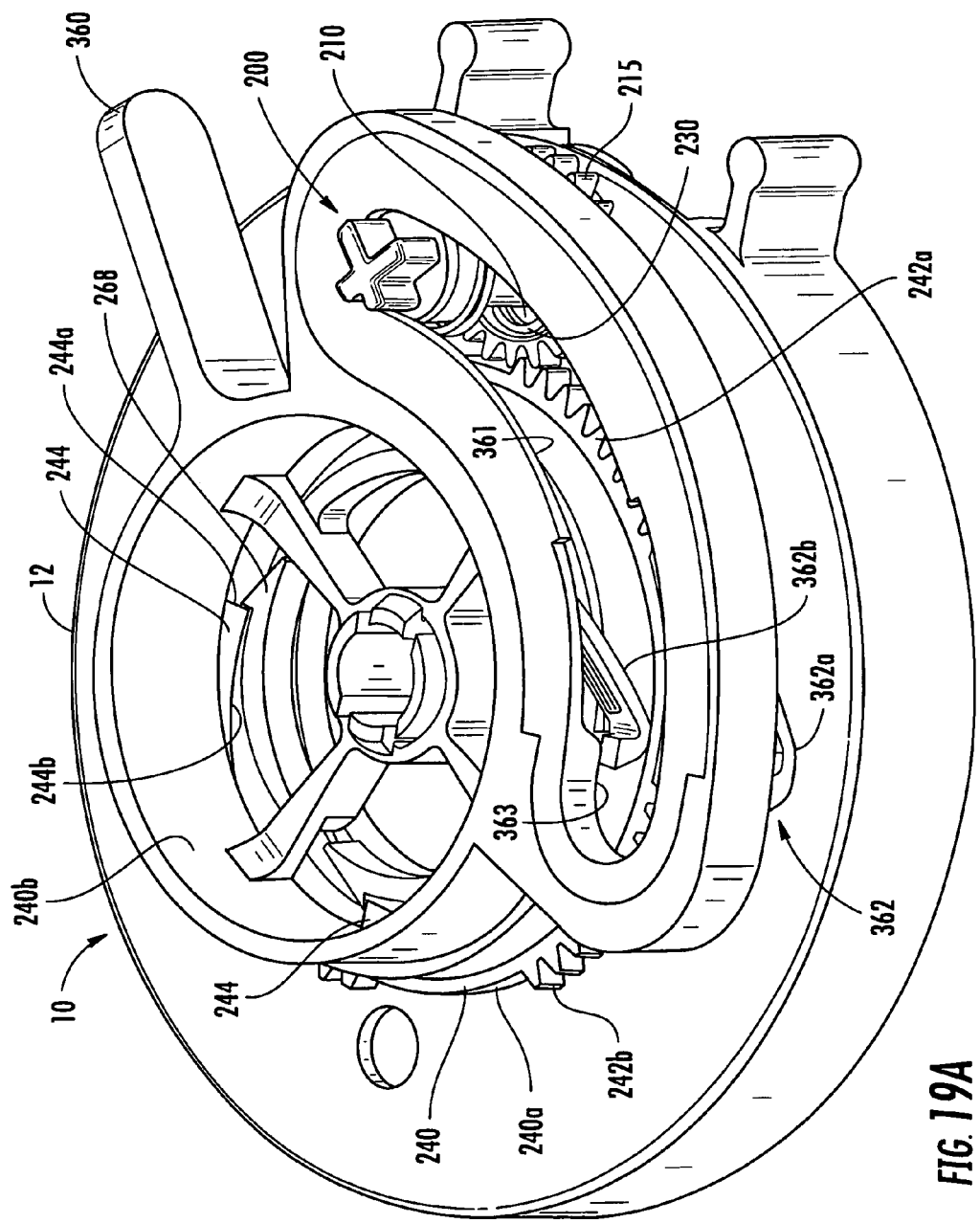
FIG. 19A is a cutaway, top perspective view of an inhaler having a rotatable piercing mechanism, according to some embodiments of the present invention.
Figure 19B:
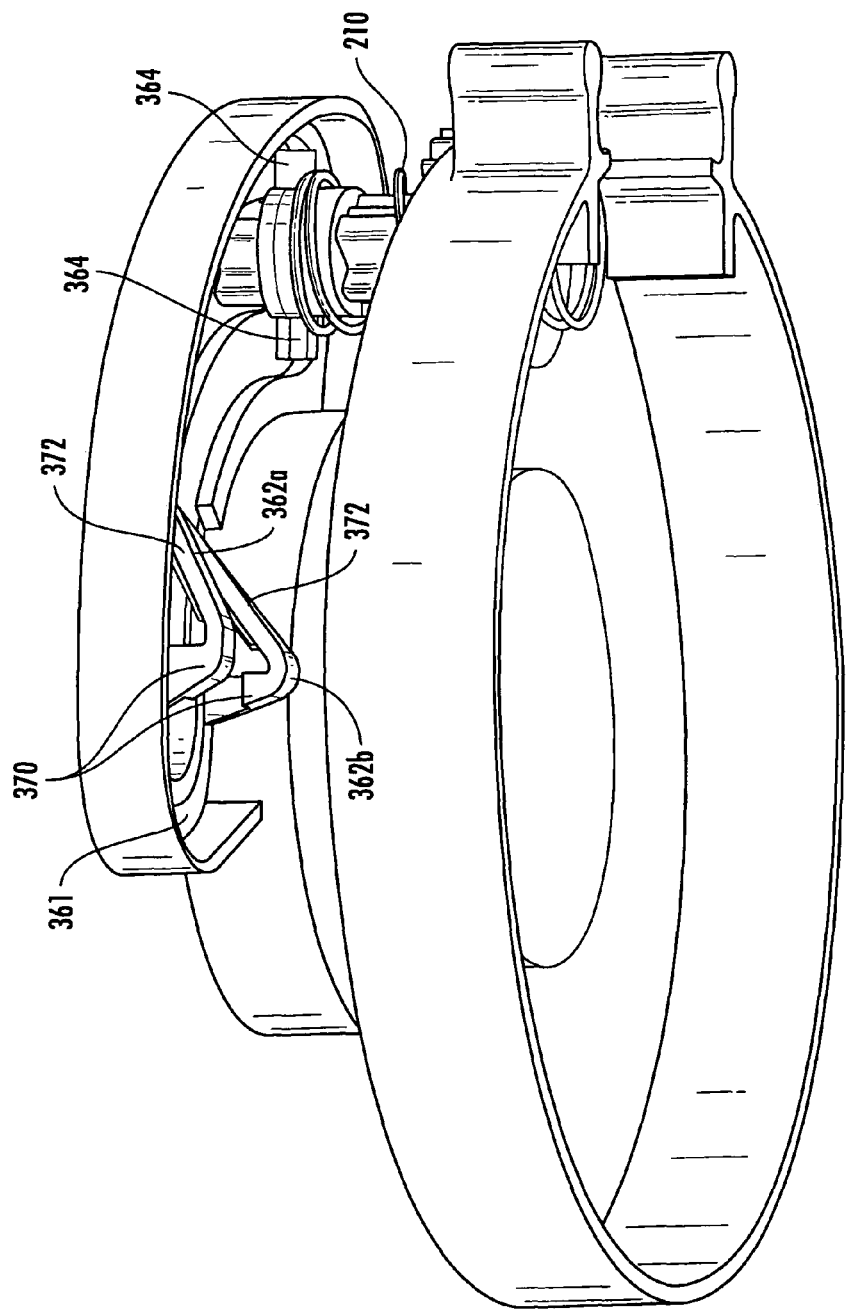
FIG. 19B is a bottom perspective view of the inhaler of FIG. 19A.
Figure 20:
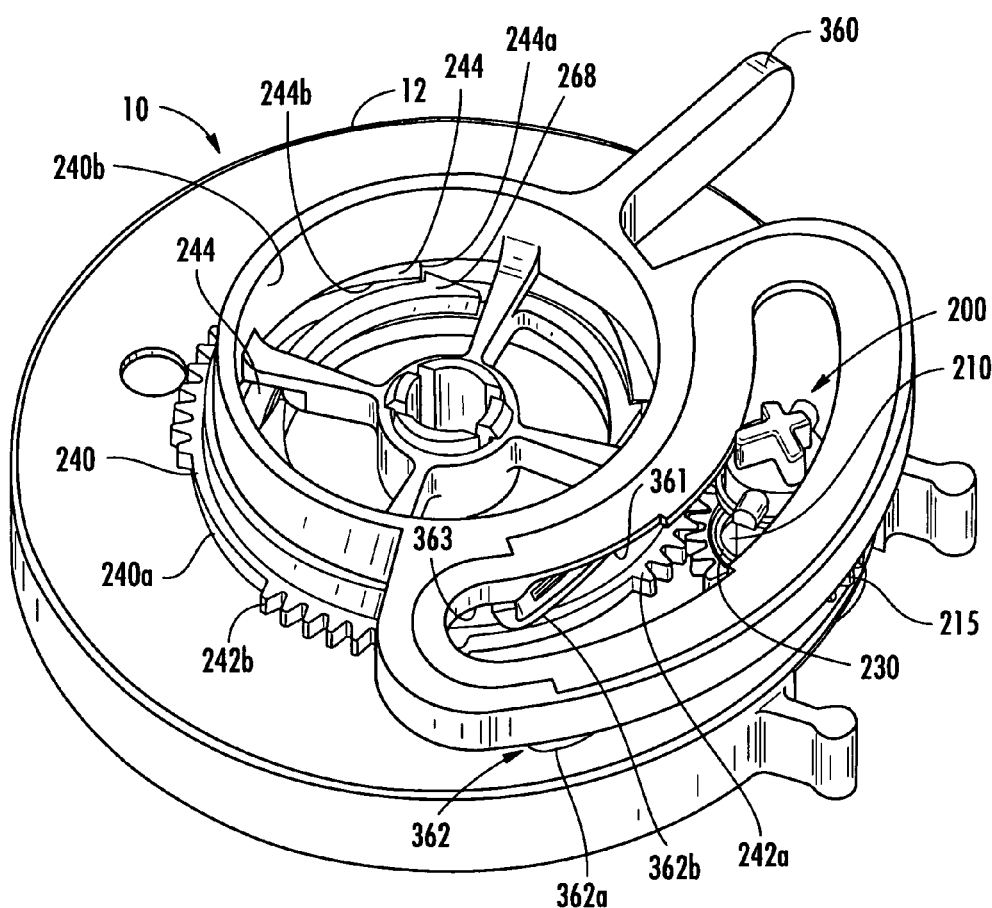
FIGS. 20 and 21A are top perspective views of the inhaler of FIG. 19A illustrating the actuator during movement from a first position to a second position and illustrating a first stage of rotation of the ring gear, according to some embodiments of the present invention.
Figure 21A:
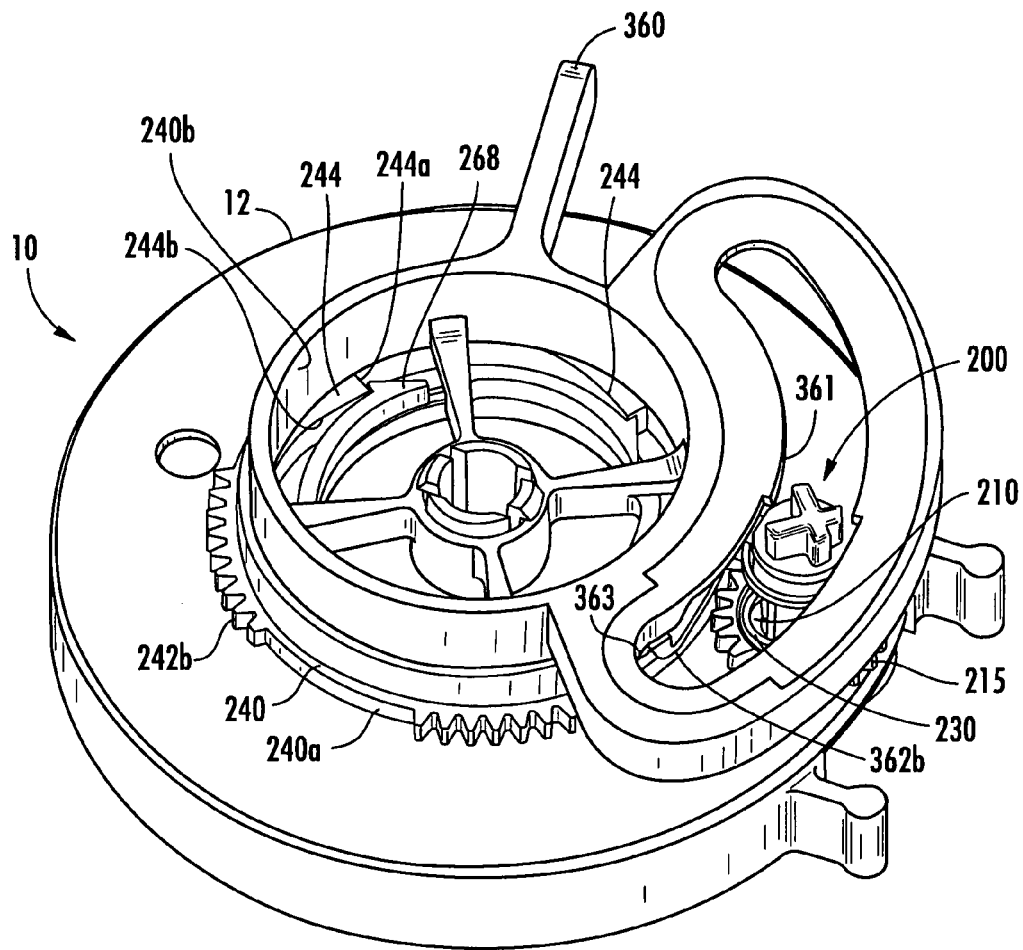
Figure 21B:
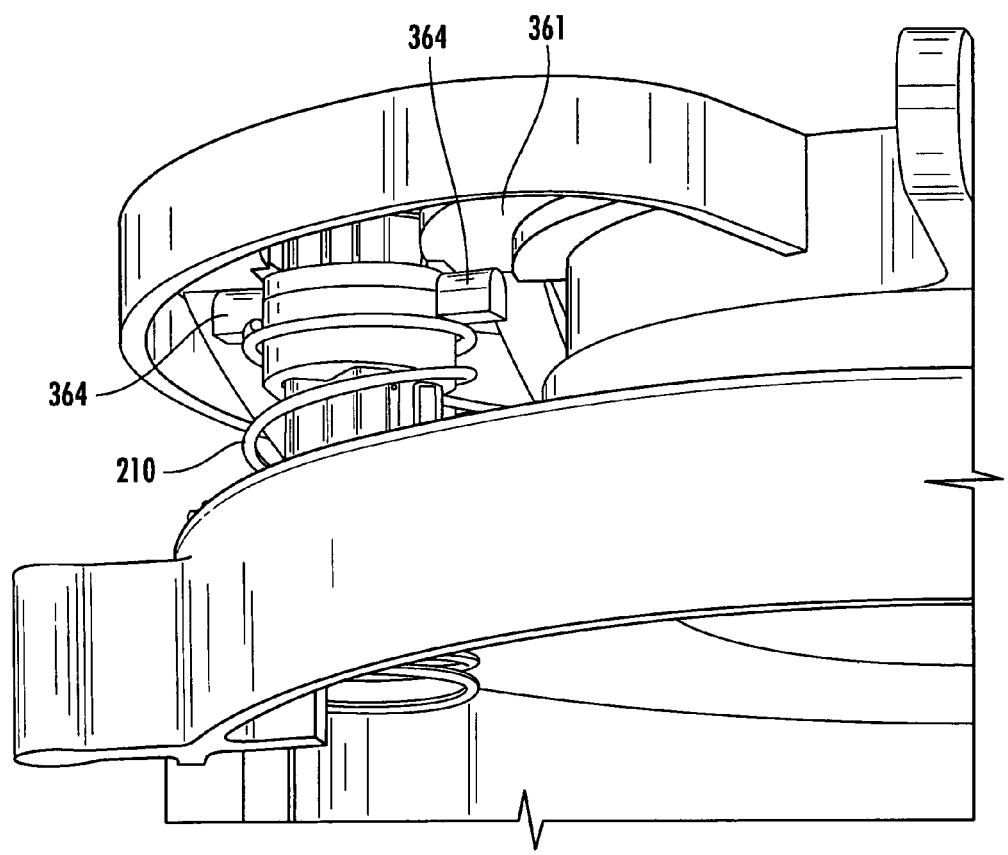
FIG. 21B is a bottom perspective view of the inhaler of FIG. 21A.
Figure 22:
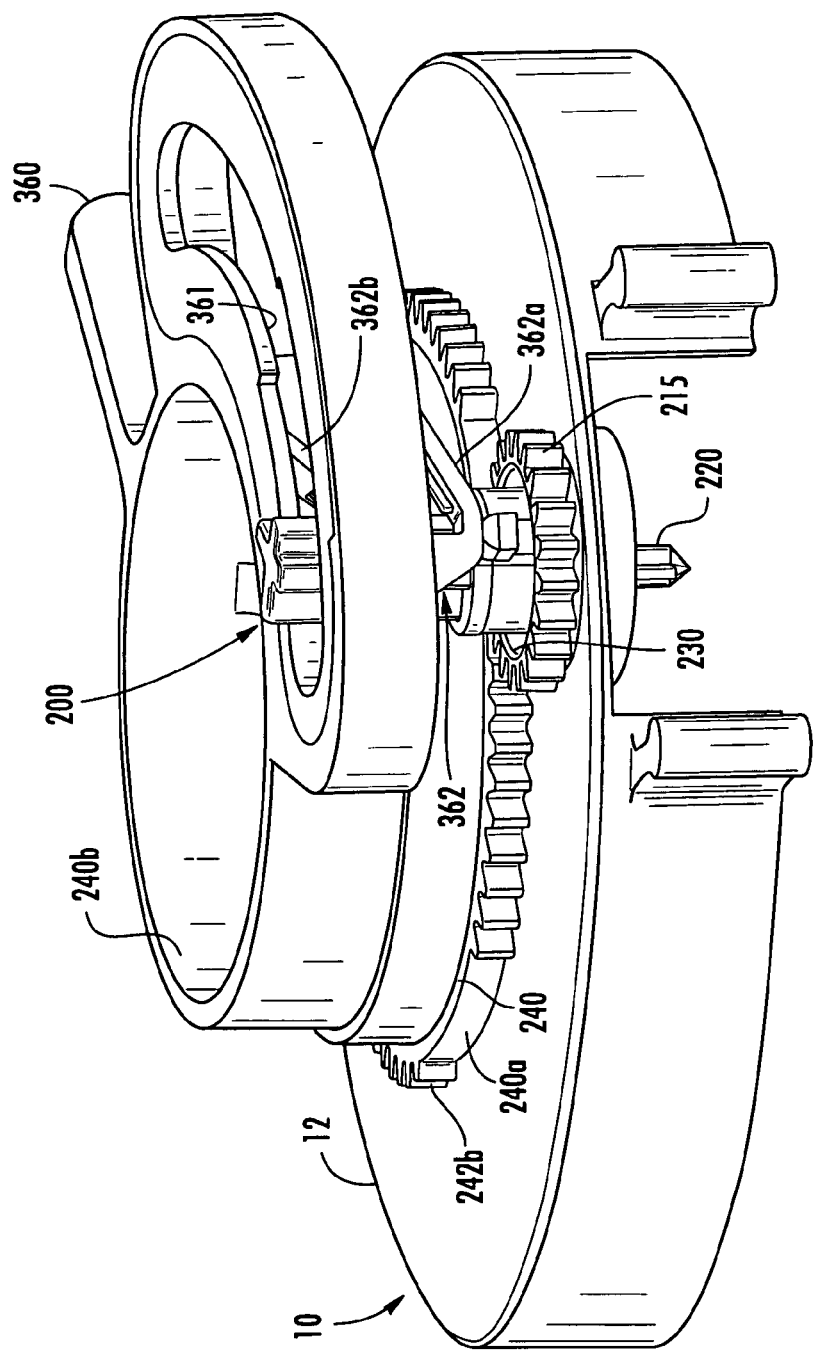
FIG. 22 is a top perspective view of the inhaler of FIG. 19A illustrating a second stage of rotation of the ring gear as the actuator is moved from the first position to the second position and illustrating the piercing member in an extended piercing position, according to some embodiments of the present invention.

The actuator 360 is movable by a user of the inhaler 10 between first (FIGS. 19A, 19B) and second (FIGS. 23A, 23B) positions. Movement of the actuator 360 from the first position to the second position causes rotation of the ring gear 240 by a predetermined amount. As is shown, this predetermined amount includes three stages of rotation of the ring gear 240. During a first stage of rotation of the ring gear 240 via the actuator 360, a first set of ring gear teeth 242*a* cooperates with the drum gear teeth 215 and rotates the drum 210 such that the piercing member 220 overlies a dose container (not shown). This first stage of rotation of the ring gear 240 is illustrated in FIGS. 19A-19B through FIGS. 21A-21B. In the illustrated embodiment, the drum 210 is rotated clockwise (as viewed from above) by one hundred eighty degrees (180°) during the first stage of rotation of the ring gear 240. As illustrated in FIGS. 19A-19B, at the beginning of the first stage of rotation, the piercing mechanism arms 364 are oriented such that they are in contacting relationship with the actuator surface 361. The rotation of the ring gear 240 during the first stage causes rotation of the drum 210 and piercing mechanism 200 such that the arms 364 rotate one hundred eighty degrees (180°) and again are oriented such that they are in contacting relationship with the actuator surface 361, as illustrated in FIGS. 21A-21B.

Upon completion of the first stage of rotation of the ring gear, the piercing member 220 overlies a dose container and the piercing mechanism arms 364 are in position to engage the ramps 362*a*, 362*b* (FIG. 21B). Continued rotation of the ring gear 240 via the actuator 360 (i.e., the second stage of rotation) causes the ramp second legs 372 to urge the arms 364 downward, thereby causing the piercing member 220 to move downwardly to the piercing position (FIG. 22) and into the dose container.

Figure 23A:
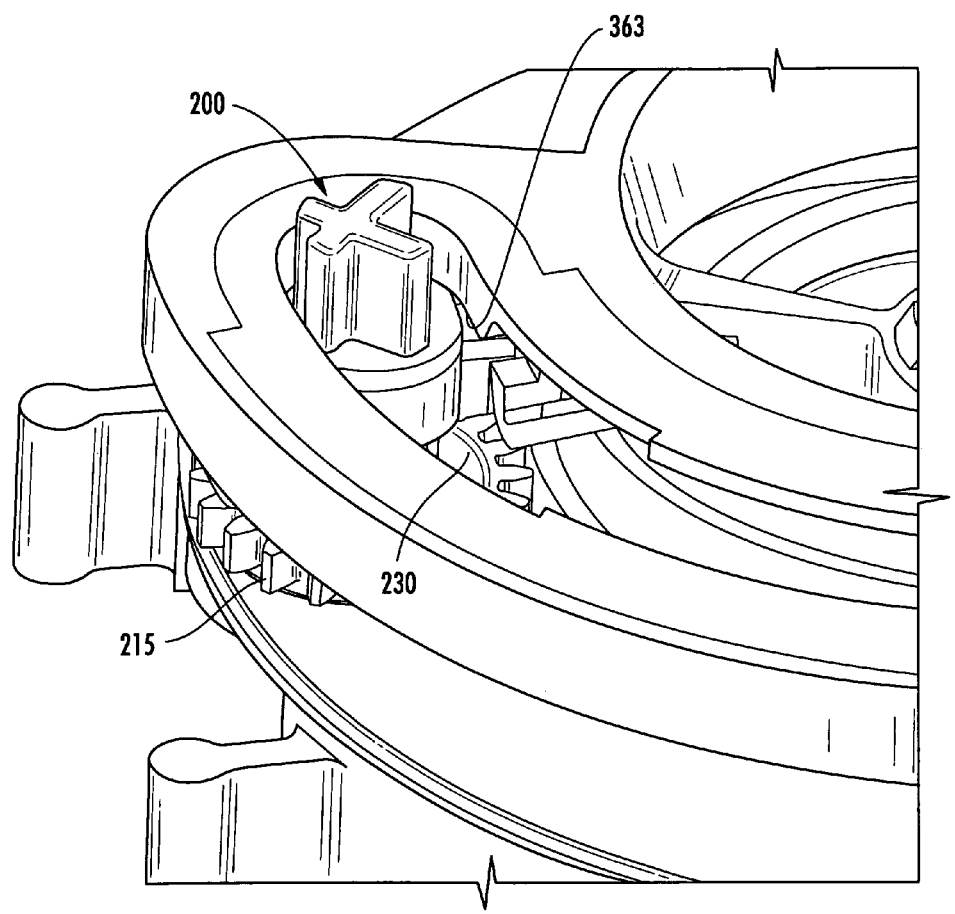
FIG. 23A is a top perspective view of the inhaler of FIG. 19A illustrating a third stage of rotation of the ring gear as the actuator is moved from the first position to the second position and illustrating the piercing member in a partially retracted position.
Figure 23B:
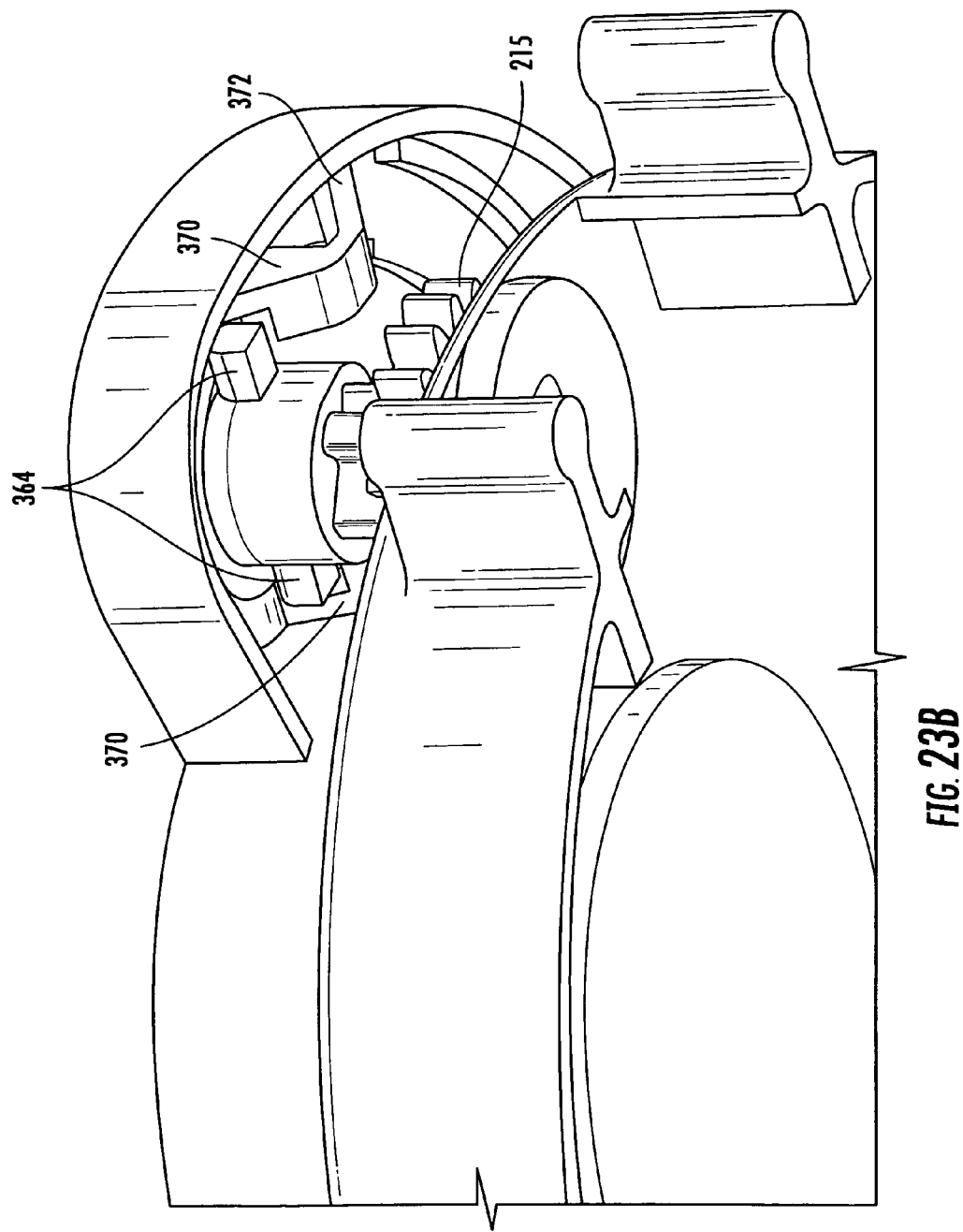
FIG. 23B is a bottom perspective view of the inhaler of FIG. 23A.
Figure 24A:
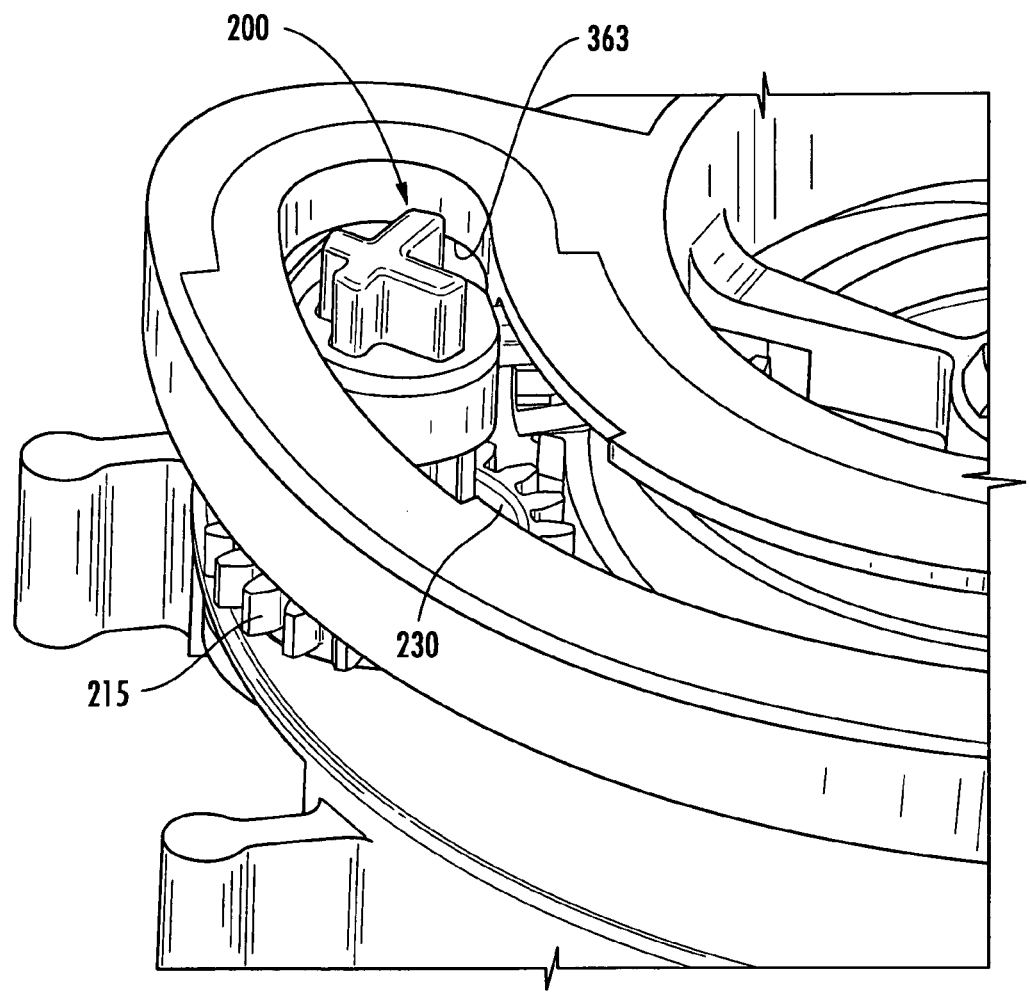
FIG. 24A is a top perspective view of the inhaler of FIG. 19A illustrating the piercing mechanism arms sliding between the ramp first legs as the actuator is moved from the second position back to the first position, according to some embodiments of the present invention.
Figure 24B:
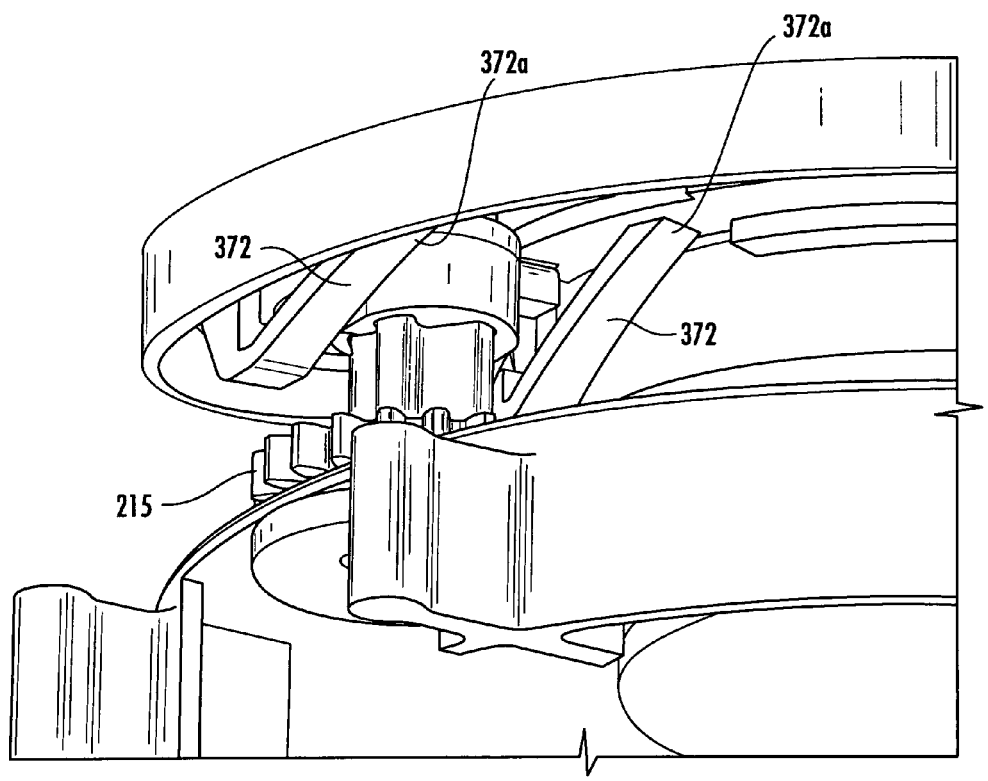
FIG. 24B is a bottom perspective view of the inhaler of FIG. 24A.
Figure 25:
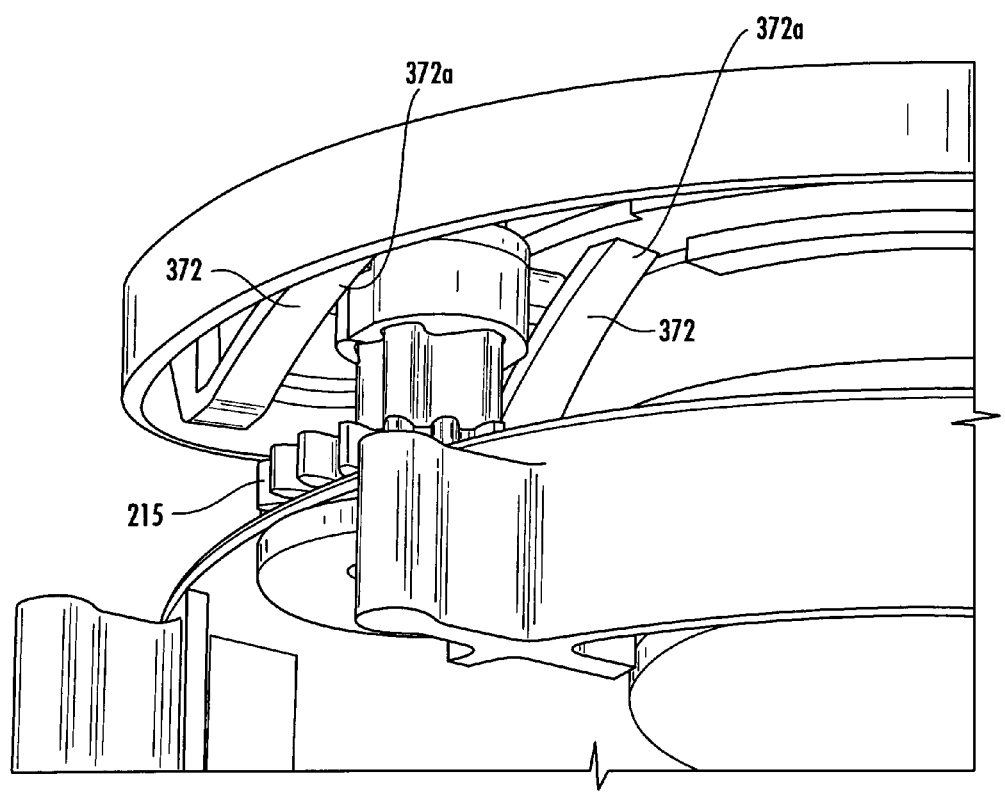
FIG. 25 is a bottom perspective view of the inhaler of FIG. 19A illustrating the piercing mechanism arms about to deflect the ramp second legs as the actuator is moved from the second position back to the first position, according to some embodiments of the present invention.
Figure 26A:
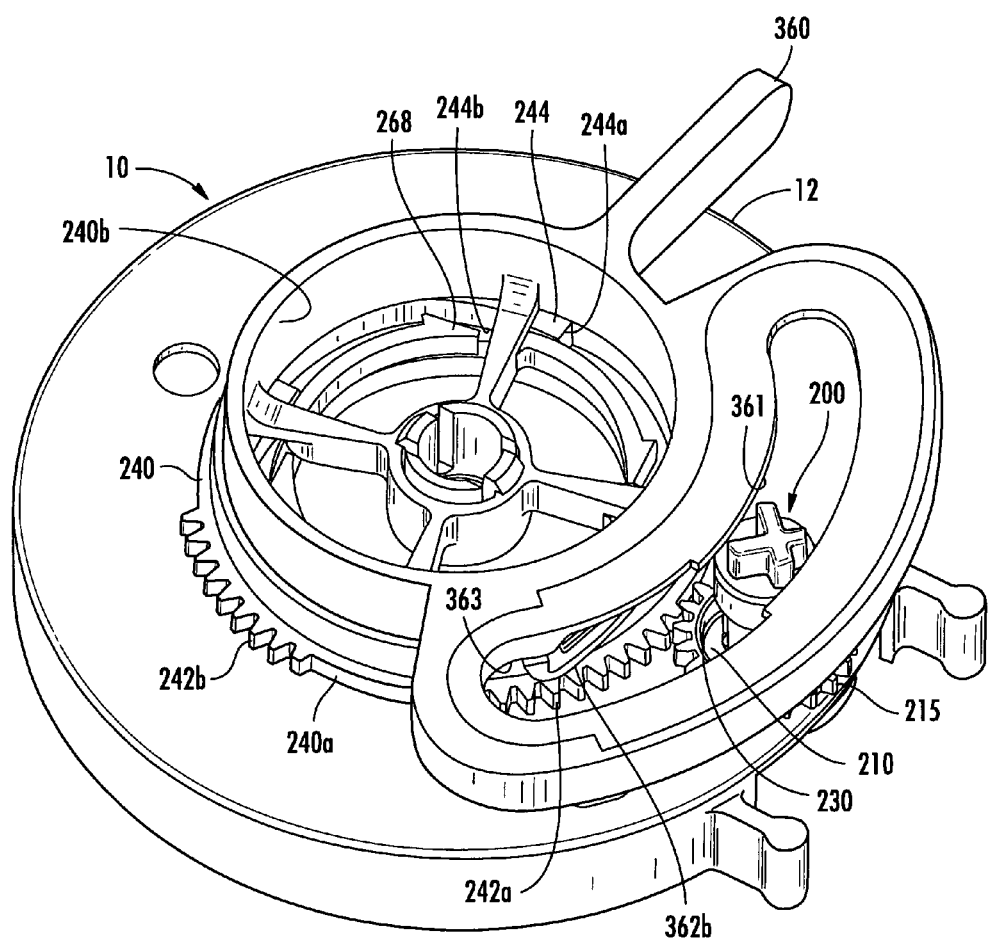
FIG. 26A is a top perspective view of the inhaler of FIG. 19A illustrating a position of the piercing mechanism after the piercing mechanism arms have passed between the ramp second legs and an actuator surface as the actuator is moved from the second position back to the first position, according to some embodiments of the present invention.
Figure 26B:
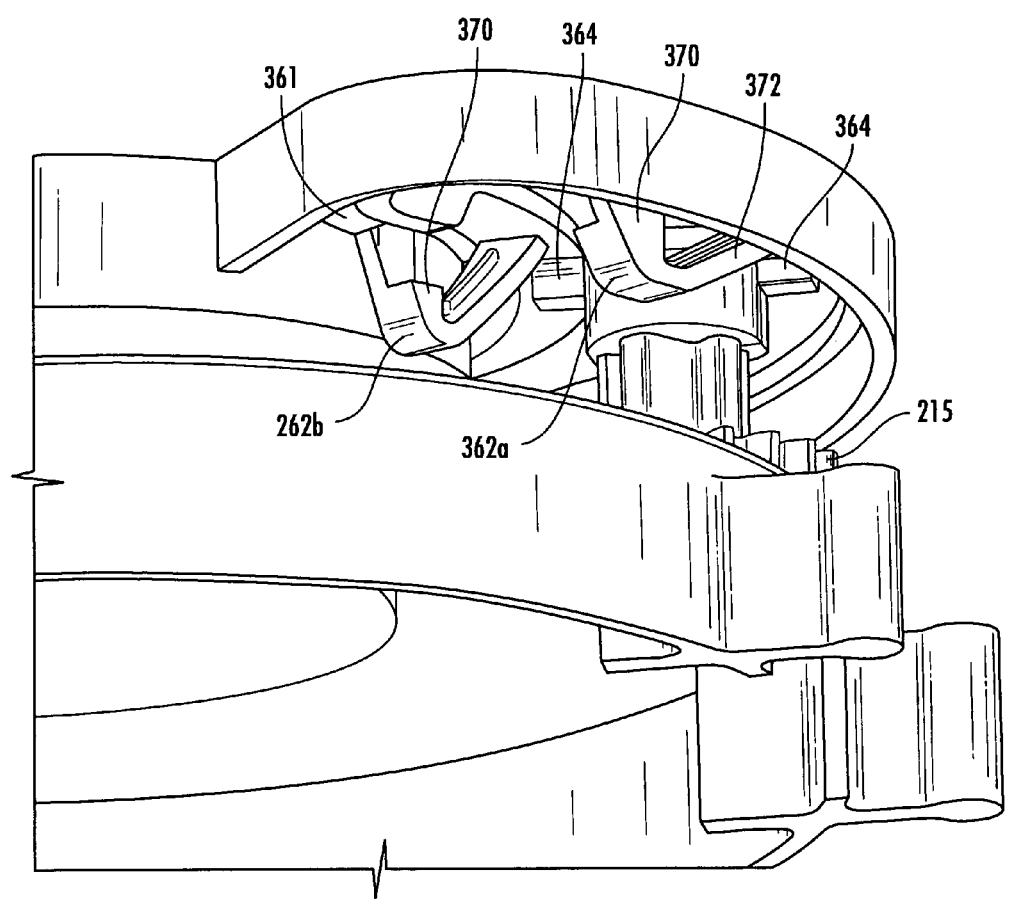
FIG. 26B is a bottom perspective view of the inhaler of FIG. 26A.

Continued rotation of the ring gear 240 via the actuator 360 (i.e., the third stage of rotation) causes the arms 364 to disengage from the ramps 362*a*, 362*b* such that the piercing member 220 moves upwardly under the force of the biasing member 230 (FIGS. 23A-23B) and such that arms 364 contact actuator surface 363 (FIG. 23A). Actuator surface 363 is closer to the disk assembly 20 (not shown) than actuator surface 361, as illustrated in FIG. 19A. Thus, when arms 364 are in contact with actuator surface 363, the piercing member 220 is partially retracted from a dose container and the function of blocking powder from falling out of the airway channel 51 (FIG. 5A) should the inhaler 10 be inverted, as described above. At the end of the third stage of rotation of the ring gear 240, the actuator 360 is at the second position.

At this point of operation (when the actuator 360 is in the second position), the user inhales powder from the dose container. After inhalation of the powder, the user moves the actuator 360 from the second position (FIGS. 23A-23B) back to the first position (i.e., counterclockwise). During movement of the actuator 360 from the second position back to the first position, the ring gear 240 is held stationary and the piercing member 220 fully retracts from the dose container. The biasing member 230 urges the piercing mechanism 200 upwardly as described above. Thus, as the actuator 360 is rotated back to the first position, the piercing mechanism arms 364 are in contact with the actuator surface 363 and then actuator surface 361, which is further away from the disk assembly, as a result of urging by the biasing member 230. When the arms 364 are in contact with the actuator surface 361, the piercing member 220 is fully retracted from the dose container.

As the actuator 360 is rotated back to the first position, the piercing member 220 does not rotate. The arms 364 of the piercing mechanism 200, which are in contact with actuator surface 361, slide between the ramp first legs 370 and under the second legs 372. Each arm 364 causes a respective second leg 372 to deflect such that the arm can slide between the leg free end 372a and the actuator surface 361 such that the piercing mechanism can move relative to the actuator 360 as illustrated in FIGS. 24A-24B through 26A-26B. The second legs 372 are resilient in that they return to a non-deflected position such that the free end 372a is in contacting relationship with the actuator surface 361 or is in close relationship therewith as described above after the arms 364 pass between the free ends 372a and the actuator surface 361. Continued counterclockwise movement of the actuator 360 returns the piercing mechanism 200 to the first position. The inhaler 10 is now ready for another cycle.

Certain embodiments may be particularly suitable for dispensing medication to respiratory patients, diabetic patients, cystic fibrosis patients, or for treating pain. The inhalers may also be used to dispense narcotics, hormones and/or infertility treatments.

A dry powder inhaler, comprising:
a circular dose container disk assembly having a plurality of circumferentially spaced apart radially oriented airway channels aligned with a plurality of circumferentially spaced apart sealed drug chambers with dry powder therein held in first and second concentric rows of different radius, wherein prior to active dispensing, the airway channels are drug free;
a mouthpiece configured to rotatably engage an outer perimeter of the dose container disk to communicate with the airway channels to entrain dry powder from an opened drug chamber to deliver dry powder to a user; a piercing mechanism configured to open the dose container chambers to release the dry powder therein;
an indexing mechanism in communication with the circular dose disk;
a mouthpiece cover in communication with the indexing mechanism and/or piercing mechanism whereby movement of the mouthpiece cover actuates the indexing mechanism to rotate the disk and/or move the piercing mechanism to alternately open a dose container on a first row then a dose container on the second row.

A method of operating an inhaler, comprising:
providing a dose container disk having opposing upper and lower primary surfaces, a first row of circumferentially spaced apart dose containers at a first radius and a second row of circumferentially spaced apart dose containers at a second radius so that the first and second rows are concentric with respect to a center of the disk, wherein the dose containers have dry powder therein, wherein each dose container terminates at a respective aperture in the upper surface and at a respective aperture in the lower surface, wherein a first flexible sealant resides over the apertures in the upper surface, and a second flexible sealant resides over the apertures in the lower surface;
rotating a piercing mechanism to a position above a dose container in the a row;
advancing a piercing mechanism to open both sealants and release dry powder from a dose container;
retracting the piercing mechanism from the dose container; and
rotating the piercing mechanism to a position not above a dose container in either row.

The following exemplary claims are presented in the specification to support one or more devices, features, and methods of embodiments of the present invention. While not particularly listed below, Applicant preserves the right to claim other features shown or described in the application.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A dry powder inhaler, comprising:
a housing;
a dose container disk rotatably secured within the housing, wherein the dose container disk comprises opposing upper and lower primary surfaces, a first row of circumferentially spaced apart through apertures associated with dose containers at a first radius and a second row of circumferentially spaced apart apertures associated with dose containers at a second radius;
a first flexible sealant residing over the apertures in the upper surface, and a second flexible sealant residing over the apertures in the lower surface, and wherein the dose containers have dry powder therein; and
a piercing mechanism configured to serially alternate between rows to pierce the sealants of a respective dose container in the first row, then pierce the sealants of a respective dose container in the second row, wherein the piercing mechanism comprises:
a rotatable drum; and
an elongate piercing member operably associated with the rotatable drum and capable of reciprocal movement between piercing and non-piercing positions.

2. The dry powder inhaler of claim 1, wherein the rotatable drum comprises an open end, an opposite closed end, and a cylindrical wall extending from the closed end and terminating at the open end, wherein the closed end includes an aperture formed therein and wherein the elongate piercing member comprises a distal piercing portion and a proximal head portion, wherein the distal piercing portion extends through the drum aperture and through the first and second sealants when the piercing member is in a piercing position, and wherein the distal piercing portion is retracted above a lower surface of the drum aperture when in a retracted position.

3. The dry powder inhaler of claim 1, wherein the piercing mechanism comprises a biasing member configured to urge the piercing member toward a retracted position.

4. The dry powder inhaler of claim 2, wherein the drum comprises gear teeth that extend circumferentially around the cylindrical wall, and further comprising a ring gear rotatably secured within the housing, wherein the drum gear teeth cooperate with the ring gear such that rotation of the ring gear by a predetermined amount causes the drum to rotate such that the piercing member moves from a position overlying a dose container in one row to a position overlying a dose container in the other row.

5. The dry powder inhaler of claim 2, wherein the drum comprises gear teeth that extend circumferentially around the cylindrical wall, and further comprising a ring gear rotatably secured within the housing, wherein the drum gear teeth cooperate with the ring gear such that rotation of the ring gear by a predetermined amount causes the drum to rotate about one-hundred eighty degrees (180°).

6. The dry powder inhaler of claim 4, wherein the ring gear comprises sets of teeth circumferentially spaced-apart.

7. The dry powder inhaler of claim 4, wherein the dose container assembly comprises gear teeth on an outer perimeter thereof, wherein the drum cylindrical wall comprises a pair of one or more teeth extending outwardly from the wall in diametric opposition that are configured to engage the dose container assembly gear teeth, and wherein rotation of the drum causes rotation of the dose container assembly.

8. The dry powder inhaler of claim 4, further comprising an actuator that is movable between first and second positions, wherein movement of the actuator from the first position to the second position causes the piercing member to pierce the sealants over and under a dose container and then move to a partially retracted position, and wherein movement of the actuator from the second position to the first position causes the piercing member to retract and the ring gear to move the predetermined amount such that the piercing member rotates from a position overlying a dose container in one row to another position overlying a dose container in the other row.

9. The dry powder inhaler of claim 8, wherein rotation of the piercing member causes the dose container assembly to rotate relative to the piercing mechanism.

10. The dry powder inhaler of claim 4, further comprising an actuator that is movable between first and second positions, wherein movement of the actuator from the first position to the second position causes the ring gear to move the predetermined amount such that the piercing member rotates from a position overlying a dose container in one row to another position overlying a dose container in the other row, to pierce the sealants over and under a dose container, and then move to a partially retracted position, and wherein movement of the actuator from the second position to the first position causes the piercing member to fully retract.

11. The dry powder inhaler of claim 10, wherein rotation of the piercing member causes the dose container assembly to rotate relative to the piercing mechanism.

12. The dry powder inhaler of claim 4, further comprising an actuator that is movable between first and second positions, wherein movement of the actuator from the first position to the second position causes the piercing member to pierce the sealants over and under a dose container, and wherein movement of the actuator from the second position to the first position causes the piercing member to retract and the ring gear to move the predetermined amount such that the piercing member rotates from a position overlying a dose container in one row to another position overlying a dose container in the other row.

13. The dry powder inhaler of claim 4, further comprising an actuator that is movable between first and second positions, wherein movement of the actuator from the first position to the second position causes the ring gear to move the predetermined amount such that the piercing member rotates from a position overlying a dose container in one row to another position overlying a dose container in the other row, and wherein movement of the actuator from the second position to the first position causes the piercing member to fully retract.

14. The dry powder inhaler of claim 8, wherein the ring gear comprises an inner perimeter having a plurality of spaced-apart steps, and wherein the actuator comprises a pawl that engages one of the plurality of spaced-apart steps to cause rotation of the ring gear when the actuator is moved from the second position to the first position.

15. The dry powder inhaler of claim 8, wherein the actuator comprises a first portion that engages the head portion of the piercing member and that causes the piercing member to move to the piercing position, and an adjacent second portion causes the piercing member to move to the partially retracted position.

16. The dry powder inhaler of claim 10, wherein the ring gear comprises an inner perimeter having a plurality of spaced-apart steps, and wherein the actuator comprises a pawl that engages one of the plurality of spaced-apart steps to cause rotation of the ring gear when the actuator is moved from the first position to the second position.

17. The dry powder inhaler of claim 10, wherein the actuator comprises a first portion that engages the head portion of the piercing member and that causes the piercing member to move to the piercing position, and an adjacent second portion causes the piercing member to move to the partially retracted position.

18. The dry powder inhaler of claim 1, wherein the first row of dose containers have centerlines that are circumferentially spaced apart from centerlines of the second row of dose containers.

19. The dry powder inhaler of claim 1, wherein the piercing member comprises a corkscrew piercer configured to pierce the sealants with a straight vertical non-rotational movement.

20. The dry powder inhaler of claim 1, wherein the piercing member comprises a fluted piercer configured to pierce the sealants.

21. The dry powder inhaler of claim 20, wherein the fluted piercer comprises three or four lobes.

22. The dry powder inhaler of claim 1, wherein each dose container comprises a dry powder having a pharmaceutically active agent, and wherein the agent comprises one or more of the following bronchodilators:

albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-.alpha.-[[[6-[2-(2-pyridinyl)ethoxy]hexyl]methyl]benzenemethanol;

wherein the bronchodilator may be used in the form of salts, esters or solvates to thereby optimize the activity and/or stability of the medicament.

23. The dry powder inhaler of claim 2, wherein the drum comprises gear teeth that extend circumferentially around the cylindrical wall, and further comprising:

a ring gear rotatably secured within the housing and comprising sets of teeth circumferentially spaced-apart; and an actuator that is movable between first and second positions, wherein movement of the actuator from the first position to the second position causes rotation of the ring gear by a predetermined amount, wherein, during a first stage of the rotation, a first set of ring gear teeth cooperates with the drum gear teeth and rotates the drum such that the piercing member overlies a dose container, wherein, during a second stage of the rotation, the piercing member is moved to the piercing position, wherein, during a third stage of the rotation, the piercing member is moved to the retracted position, and wherein, during a fourth stage of the rotation, a second set of ring gear teeth cooperates with the drum gear teeth and rotates the drum such that the piercing member does not overlie a dose container.

24. The dry powder inhaler of claim 23, wherein the dose container assembly comprises gear teeth on an outer perimeter thereof, wherein the drum cylindrical wall comprises a pair of one or more teeth extending outwardly from the wall in diametric opposition that are configured to engage the dose container assembly gear teeth, and wherein rotation of the drum causes rotation of the dose container assembly.

25. The dry powder inhaler of claim 23,
wherein the actuator comprises a ramp;
wherein the piercing mechanism comprises at least one arm extending outwardly therefrom;
wherein, during the second stage of the rotation, the at least one arm is contacted by the ramp to urge the piercing member to the piercing position; and
wherein, during the third stage of the rotation, the at least one arm disengages from the ramp and the piercing member is urged to the retracted position by a biasing member.

26. The dry powder inhaler of claim 25, wherein the ramp comprises spaced-apart first and second inclined portions, wherein the at least one arm comprises a pair of arms extending outwardly from the piercing member in opposing relationship, and wherein, during the second stage of the rotation, each arm is contacted by a respective inclined portion to urge the piercing member to the piercing position.

27. The dry powder inhaler of claim 23, wherein the drum is rotated by ninety degrees (90°) during the first stage, and wherein the drum is rotated by ninety degrees (90°) during the fourth stage.

28. The dry powder inhaler of claim 2, wherein the drum comprises gear teeth that extend circumferentially around the cylindrical wall, and further comprising:
a ring gear rotatably secured within the housing and comprising sets of teeth circumferentially spaced-apart; and
an actuator that is movable between first and second positions, wherein movement of the actuator from the first position to the second position causes rotation of the ring gear by a predetermined amount, wherein, during a first stage of the rotation, a first set of ring gear teeth cooperates with the drum gear teeth and rotates the drum such that the piercing member overlies a dose container, wherein, during a second stage of the rotation, the piercing member is moved to the piercing position, and wherein, during a third stage of the rotation, the piercing member is moved to a partially retracted position.

29. The dry powder inhaler of claim 28,
wherein the actuator comprises a pair of ramps positioned in adjacent, spaced-apart relationship;
wherein the piercing mechanism comprises a pair of arms extending outwardly therefrom in opposing relationship;
wherein, during the second stage of the rotation, each arm is contacted by a respective ramp to urge the piercing member to the piercing position; and
wherein, during the third stage of the rotation, each arm disengages from a respective ramp and the piercing member is urged to a partially retracted position by a biasing member.

30. The dry powder inhaler of claim 29, wherein each ramp comprises a first leg attached to an actuator surface and a second leg having a free end adjacent to the actuator surface, wherein, during the second stage of the rotation, an arm is contacted by a respective second leg to urge the piercing member to the piercing position, and wherein the second leg is configured to deflect such that a respective arm can pass between the free end and the actuator surface when the actuator is moved from the second position to the first position.

31. A method of operating an inhaler, comprising:
providing a dose container disk having opposing upper and lower primary surfaces, a first row of circumferentially spaced apart dose containers at a first radius and a second row of circumferentially spaced apart dose containers at a second radius so that the first and second rows are concentric with respect to a center of the disk, wherein the dose containers have dry powder therein, wherein each dose container terminates at a respective aperture in the upper surface and at a respective aperture in the lower surface, wherein a first flexible sealant resides over the apertures in the upper surface, and a second flexible sealant resides over the apertures in the lower surface; and
operating a piercing mechanism to serially rotate between the first and second rows to pierce the sealants of a dose container in one row, then pierce the sealants of a dose container in the other row.

* * * * *

UNITED STATES PATENT AND TRADEMARK OFFICE
CERTIFICATE OF CORRECTION

| | | |
|---|---|---|
| PATENT NO. | : 8,646,446 B2 | Page 1 of 1 |
| APPLICATION NO. | : 13/054809 | |
| DATED | : February 11, 2014 | |
| INVENTOR(S) | : Lewis et al. | |

It is certified that error appears in the above-identified patent and that said Letters Patent is hereby corrected as shown below:

On Title Page:
Item (75), Inventors:
    Please correct: "Scott Alexander Lewis, Cambbridge (GB);"
        to read -- Scott Alexander Lewis, Cambridge (GB); --

Signed and Sealed this
Eleventh Day of November, 2014

Michelle K. Lee
*Deputy Director of the United States Patent and Trademark Office*